(12) United States Patent
Klosin et al.

(10) Patent No.: US 8,071,701 B2
(45) Date of Patent: Dec. 6, 2011

(54) POLYDENTATE HETEROATOM LIGAND CONTAINING METAL COMPLEXES, CATALYSTS AND METHODS OF MAKING AND USING THE SAME

(75) Inventors: Jerzy Klosin, Midland, MI (US); Lily Ackerman, San Francisco, CA (US); Xiaohong Bei, Oak Park, CA (US); Gary M. Diamond, Menlo Park, CA (US); James Longmire, Santa Clara, CA (US); Vince Murphy, Santa Clara, CA (US); Victor Nava-Salgado, Santa Clara, CA (US); James A. W. Shoemaker, Santa Clara, CA (US)

(73) Assignees: Dow Global Technologies LLC, Midland, MI (US); Symyx Technologies, Inc., San Clara, CA (US)

( * ) Notice: Subject to any disclaimer, the term of this patent is extended or adjusted under 35 U.S.C. 154(b) by 392 days.

(21) Appl. No.: 12/095,996

(22) PCT Filed: Dec. 8, 2006

(86) PCT No.: PCT/US2006/046867
§ 371 (c)(1), (2), (4) Date: Dec. 10, 2008

(87) PCT Pub. No.: WO2007/075299
PCT Pub. Date: Jul. 5, 2007

(65) Prior Publication Data
US 2009/0221770 A1    Sep. 3, 2009

Related U.S. Application Data

(60) Provisional application No. 60/750,947, filed on Dec. 16, 2005.

(51) Int. Cl.
*C08F 4/76* (2006.01)
*C08F 4/64* (2006.01)
*C08F 4/52* (2006.01)

(52) U.S. Cl. ........ 526/170; 526/160; 526/348; 526/351; 526/346; 556/51

(58) Field of Classification Search .................... 556/51; 502/103; 526/172, 161, 901, 170, 160
See application file for complete search history.

(56) References Cited

FOREIGN PATENT DOCUMENTS
WO    WO 03/091262 A1 * 11/2003

OTHER PUBLICATIONS

Beckerle et al., J. Organomet. Chem., 2004, 689, 4636-4641.*
Applicaion No. PCT/US2006/046867; PCT International Preliminary Resport on Patentability dated Jun. 18, 2008 including Written Opinion. 11 pages.
Application No. 06848955.8; EPO Form 2906 01.91 TRI dated Apr. 30, 2010 2 pages.
Application No. 06848955.8-2104; EPO Form 2001 04.10CSX, dated Apr. 30, 2010. 2 pages.
Correspondence from Beck Greener to the European Patent Office dated Nov. 10, 2009; Re: Application No. 06848955.8. 6 pages.

* cited by examiner

Primary Examiner — Rip A. Lee

(57) ABSTRACT

Metal complexes comprising certain polydentate heteroatom containing ligands, catalysts, and coordination polymerization processes employing the same are suitably employed to prepare polymers having desirable physical properties.

16 Claims, No Drawings

POLYDENTATE HETEROATOM LIGAND CONTAINING METAL COMPLEXES, CATALYSTS AND METHODS OF MAKING AND USING THE SAME

CROSS REFERENCE STATEMENT

This application claims benefit of U.S. Provisional Application No. 60/750,947, filed Dec. 16, 2005.

BACKGROUND OF THE INVENTION

The present invention relates to ligands, ligand-metal compositions, complexes, and catalysts useful in the polymerization of olefins and other transformations, as well as processes for the polymerization of monomers (including vinylidene aromatic monomers) and to the novel polymers obtained thereby.

Ancillary (or spectator) ligand-metal coordination complexes (including organometallic complexes) and compositions are useful as catalysts, additives, stoichiometric reagents, solid-state precursors, therapeutic reagents and drugs. In the field of polymerization catalysis, and particularly in connection with homogeneous catalysts including single site catalysis, the ancillary ligand typically offers opportunities to modify the electronic and/or steric environment surrounding an active metal center. This allows the ancillary ligand to assist in the creation of possibly different polymers, as well as to control many of the important polymerization characteristics of a process employing such complexes. For example, the ancillary ligands may have a large effect on the catalytic efficiency, the useful operating temperature and pressure of the catalytic process, the polymerization rate and polymer yield per unit time, and the ability to control the molecular weight of the product. Group 4 based single site and other homogeneous catalysts are generally known for catalyzing a variety of coordination polymerization reactions. See, generally, "The Search for New-Generation Olefin Polymerization Catalysts: Life beyond Metallocenes", Gibson, et al., *Angew. Chem. Int. Ed.* 1999, 38, 428-447; *Organometallics* 1999, 18, 3649-3670 and "Advances in Non-Metallocene Olefin Polymerization Catalysts", Gibson, et al., *Chem. Rev.* 2003, 103, 283-315.

The polymerization of vinylidene aromatic monomers, especially styrene and substituted styrenes, to form non-stereoregular polymers has proven difficult to accomplish using non-metallocene catalysts. Recently, Okuda and other researchers have reported the results of their investigations, See, Okuda et al., *J. Organometallic Chem.,* 689 (2004) 4636-4641, Okuda et al., *Organometallics,* 224, 2971-2982 (2005), WO 2004/078765, Kim, et al., *Macromol. Rapid Commun.* 2004, 25, 1319-1323, and Proto et al., *Macromolecules* 2003, 36, 5942-5946. In general, the known processes have been limited to the use of relatively low reaction temperatures and the production of undifferentiated polymers.

Despite the efforts of many workers in the field, a need remains for commercially suitable catalyst systems for the polymerization of monomers, and in particular for the homopolymerization or copolymerization of vinylidene aromatic monomers, especially styrene or substituted styrenes, for the production of polymers having molecular weights high enough for general commercial use, and variable tacticities, at high reaction temperatures. In particular, what is needed is a catalyst or family of catalysts capable of making a range of vinylidene aromatic polymers with differing degrees of stereoregularity that can be controlled by the appropriate choice of catalyst and conditions. A range of product opportunities could then exist, including polymers uniquely suited for preparation via high temperature solution polymerization processes.

In particular, solution polymerization processes running at greater than 100° C. using coordination catalysts capable of producing vinylidene aromatic polymers with commercially useful molecular weights and molecular architecture are still desired in the art.

SUMMARY OF THE INVENTION

The invention provides polydentate, heteroatom containing ligands, metal complexes, and compositions that are useful as catalysts for a variety of transformations, including olefin oligomerization or polymerization reactions. In addition, the invention provides novel methods for oligomerizing or polymerizing vinylidene aromatic monomers into products having desirable properties. Finally, the invention provides techniques for preparing the foregoing ligands, metal complexes, compositions, and oligomeric or polymeric products as well as novel oligomers and polymers resulting from the foregoing reactions.

In general, the invention is directed toward metal complexes of the formula:

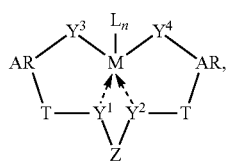

(I)

$Y^1$, $Y^2$, $Y^3$ and $Y^4$ is each independently selected from the group consisting of oxygen, phosphorus and sulfur; and optional donor bonds between $Y^1$ and M and between $Y^2$ and M are indicated by dashed arrows;

Z is a divalent group having up to 50 atoms, preferably from 2 to 50 atoms, not counting hydrogen atoms;

each AR is a divalent aromatic group of up to 50 atoms, not counting hydrogen atoms;

each T is a group having up to 30 atoms total of the general formula: $-(CR^{20}_{2-x''})_{x'}-$, wherein each $R^{20}$ substituent is independently selected from the group consisting of hydrogen, halogen, hydrocarbyl, inertly substituted hydrocarbyl, and groups of the formula: $Q(R^{21})_y$, wherein $R^{21}$ is hydrogen, halogen, hydrocarbyl, or inertly substituted hydrocarbyl, Q is O, P, S, N, Si or B, and y is an integer from 1 to 3 equal to one less than the valence of Q; x' is 1 or 2; and x" is 0 or 1; and optionally two or more $R^{20}$ substituents may be joined into a ring- or multiring-structure having from 3 to 50 atoms, provided that said ring structure is not an aromatic group;

M is a metal selected from the group consisting of Groups 36 and Lanthanides of the Periodic Table of the Elements, especially, Y, Zr, Hf, Ti, V, or Cr, more preferably Zr or Hf;

n is a number from 1 to 6, preferably 2; and each L is a neutral, monovalent or divalent ligand containing up to 50 atoms not counting hydrogen, preferably a monovalent ligand group.

Particular aspects of the invention include varying the identity of the ligands and/or metal in the complex in order to particularize the metal complex for use as a catalyst in a variety of reactions. Variations in the AR groups, T groups and Z groups will change the structure and/or identity of pendent groups, thereby affecting catalytic properties. For example, variation as to the T group will vary the metallocycle size and variation as to the Z group may be used to vary the size of the chelating group, all of which may be employed to affect the activity and stereoselectivity and regioselectivity of the catalyst.

In general, in another aspect, the invention provides catalytic methods. In the methods, one or more reagents is reacted in the presence of a catalyst comprising a composition or complex as described above, and, optionally, one or more activators, under conditions sufficient to yield one or more reaction products. In general, in another aspect, the invention provides a process for the polymerization of addition polymerizable monomers, especially $C_{2-20}$ α-olefins employing the foregoing catalyst composition.

In another aspect, the invention is directed toward a method of producing vinylidene aromatic polymers by coordination polymerization, comprising polymerizing one or more vinylidene aromatic monomers, especially one or more of styrene or a substituted styrene, under solution polymerization conditions at a reaction temperature greater than or equal to 100° C. in the presence of the foregoing catalyst composition. Desirably the resulting polymers in one embodiment of the present invention contain significant numbers of isotactic vinylidene aromatic sequences as determined by triad sequence distribution, yet they retain a high clarity and a low level of crystallinity, as measured by Differential Scanning Calorimetry (DSC). Highly desirably they possess an isotactic index (percent mm triads) between 35 and 95 percent, more desirably still, between 40 and 93 percent, between 40 and 90 percent, or even between 40 and 85 percent. In addition, the polymers may also possess a relatively low crystallinity, as measured by DSC, such that the resulting polymers are substantially amorphous.

Also in more specific embodiments, the reaction temperature is higher than 100° C., more preferably higher than 110° C., or higher even than 115° C. In yet another aspect directed to copolymerization of one or more vinylidene aromatic monomers, optionally in combination with one or more non-vinylidene aromatic monomers, especially one or more aliphatic α-olefins, the invention is directed toward a method of producing polymers having selected properties, especially substantially amorphous structure, employing the foregoing polymerization conditions. The catalyst used in these aspects comprises the foregoing metal complex according to formula I and one or more activating cocatalysts.

In an additional aspect, the invention is directed toward the polymers containing significant numbers of isotactic vinylidene aromatic sequences, while retaining a high clarity and a low level of crystallinity. Highly desirably the polymers possess an isotactic index between 35 and 95 percent, more desirably still, between 40 and 93 percent, between 40 and 90 percent, or even between 40 and 85 percent, and a relatively low crystallinity, such that the resulting polymers are substantially amorphous, preferably no crystallinity, as measured by DSC.

The invention can be implemented to provide one or more of the following advantages. The ligands, compositions, complexes and polymerization methods of the invention can be used to provide catalysts producing polymers of vinylidene aromatic monomers having controlled tacticity. Catalysts incorporating the ligands, compositions and/or complexes can be used to catalyze a variety of transformations, such as olefin oligomerization or polymerization. By selecting an appropriate ligand and metal, compositions and/or complexes can be obtained to provide for desired properties in the resulting product. Thus, polymers produced using the ligands, compositions, complexes, and methods of the invention can exhibit higher (or lower or no) melting points, higher (or lower) molecular weights, and/or higher (or lower) crystallinities, than polymers produced using prior known catalysts. In some embodiments, products having little or no stereo-regularity or possessing other desirable product properties can be obtained by selecting catalysts and process conditions that provide those products. In other embodiments, products having isotacticity or other desirable product properties can be obtained by selecting catalysts and process conditions that provide those products. Thus, the catalysts can be selected to produce a desired tacticity, from isotactic to atactic. Moreover, due to the incorporation of sufficient stereo-errors in the resulting polymer, amorphous polymers having significant numbers of isotactic triad sequences, but having performance properties similar to conventionally prepared atactic polyvinylidene aromatic polymers, can be prepared. Catalysts incorporating the present ligands, compositions and/or complexes can be used according to the polymerization methods of the invention to produce polymers under commercially desirable polymerization conditions.

DETAILED DESCRIPTION

All reference to the Periodic Table of the Elements herein shall refer to the Periodic Table of the Elements, published and copyrighted by CRC Press, Inc., 2003. Any reference to a Group or Groups shall be to the Group or Groups as reflected in this Periodic Table of the Elements using the IUPAC system for numbering groups. For purposes of United States patent practice, the contents of any patent, patent application, or publication referenced herein are hereby incorporated by reference in their entirety (or the contents of the equivalent US version thereof are so incorporated by reference) especially with respect to the disclosure of synthetic techniques, definitions and general knowledge in the art. Unless stated to the contrary, clear from the context, or conventional in the art, all parts and percents are based on weight.

The term "comprising" and derivatives thereof is not intended to exclude the presence of any additional component, step or procedure, whether or not the same is disclosed herein. In order to avoid any doubt, all compositions claimed herein through use of the term "comprising" may include any additional additive, adjuvant, or compound whether polymeric or otherwise, unless stated to the contrary. In contrast, the term, "consisting essentially of" excludes from the scope of any succeeding recitation any other component, step or procedure, excepting those that are not essential to operability or are only present de minimis. The term "consisting of" excludes any component, step or procedure not specifically delineated or listed. The term "or", unless stated otherwise, refers to the listed members individually as well as in any combination.

As used herein, the phrase "characterized by the formula" is not intended to be limiting and is used in the same way that "comprising" is commonly used. The term "independently selected" is used herein means that the indicated groups can be identical or different. Use of the singular includes use of the plural and vice versa (for example, the term "hexane solvent", includes all hexane isomers). The term "compound" refers to an organic or inorganic substance composed of the atoms or ions of two or more elements. The term "complex" refers to a compound comprising one or more metal cations and one or more anionic or neutral ligands, at least one of said ligands being bonded to the metal by means of donor electrons. For the purposes of illustration, representative groups and compounds are named herein. These enumerated groups and compounds are intended to supplement and illustrate suitable embodiments, and not to preclude other groups or compounds reasonably known to those of skill in the art.

"Optional" or "optionally" means that the subsequently described event or circumstance may or may not occur, and that the description includes instances where the event or circumstance occurs and instances where it does not occur. For example, the phrase "optionally substituted hydrocarbyl" means that a hydrocarbyl moiety may or may not be substituted and that the description includes both substituted hydrocarbyl groups and unsubstituted hydrocarbyl groups.

The term "substituted" as in "substituted hydrocarbyl," "substituted aryl," "substituted alkyl," and the like, means that in the group in question (for example, the hydrocarbyl, alkyl, aryl or other moiety that follows the term), at least one hydrogen atom bound to a carbon atom or other native atom of the group is replaced with a substituent or substituent group of up to 50 atoms excluding structures encompassed by the base named group. For example, aryl substituted aryl groups or alkyl substituted alkyl groups are simply classed as aryl or alkyl groups rather than substituted aryl or substituted alkyl groups, respectively. Examples of suitable substituents (depending on the base group to which they are attached) include: hydrocarbyl-, hydroxy-, alkoxy-, hydrocarbylthio-, dihydrocarbylphosphino-, dihydrocarbylamino-, halo-, trihydrocarbylsilyl-, and trihydrocarbylsilylmethyl-groups. When the term "substituted" introduces a list of possible substituted groups, it is intended that the term apply to every member of that group. That is, the phrase "substituted alkyl, alkenyl and alkynyl" is to be interpreted as "substituted alkyl, substituted alkenyl and substituted alkynyl." Similarly, "optionally substituted alkyl, alkenyl and alkynyl" is to be interpreted as "optionally substituted alkyl, optionally substituted alkenyl and optionally substituted alkynyl."

The term "saturated" refers to a compound or group having only single bonds between chain atoms such as ethyl, cyclohexyl, pyrrolidinyl, or acetyl. The term "unsaturated" refers compounds or groups possessing one or more double or triple bonds or a delocalized dolocalized electronic structure, such as vinyl, allyl, phenyl, acetylide, oxazolinyl, cyclohexenyl, or 1,3-butadienyl. Alkenyl and alkynyl groups, as well as groups having delocalized electrons, such as aromatic hydrocarbyl groups and heteroaryl groups, are unsaturated groups.

The terms "cyclo" and "cyclic" are used herein to refer to saturated or unsaturated groups or compounds containing three or more atoms joined in a single ring or in multiple rings, including fused ring systems wherein at least two rings are joined by means of two adjacent atoms common to both rings, bridged ring systems wherein two or more nonadjacent atoms are common to at least two rings, and spiro-rings, wherein at least two rings are joined by means of a single common atom. Suitable cyclic moieties include, for example, cyclopentyl, cyclohexyl, cyclooctenyl, bicyclooctyl, phenyl, diphenyl, napthyl, pyrrolyl, furyl, thiophenyl, and imidazolyl.

The term "hydrocarbyl" refers to radicals containing only carbon and hydrogen. Preferred groups are those containing from 1 to 50 carbon atoms, especially from 1 to 24 carbon atoms, more specifically from 1 to 16 carbon atoms. Branched or unbranched, cyclic or acyclic, saturated or unsaturated species, such as alkyl groups, cycloalkyl groups, alkenyl groups, and aryl groups are all included. The term "heterohydrocarbyl" refers to a group containing at least one atom in addition to carbon or hydrogen. Preferred heteroatoms include nitrogen, oxygen, sulfur, phosphorus, boron, chlorine, fluorine, and silicon.

The term "alkyl" as used herein refers to a branched or unbranched saturated, acyclic hydrocarbyl group bonded by means of one carbon thereof, such as methyl, ethyl, n-propyl, isopropyl, n-butyl, isobutyl, sec-butyl, t-butyl, octyl, and decyl. The term "cycloalkyl" refers to cyclic, including polycyclic, saturated hydrocarbyl groups. Examples include cyclopentyl, cyclohexyl, dicyclopentyl, norbornyl, octahydronapthyl, and spiro[3.4]octyl.

The term "alkenyl" as used herein refers to a branched or unbranched, acyclic hydrocarbyl group typically, although not necessarily, containing from 2 to 50 carbon atoms and at least one double bond. Examples include: ethenyl, 1-methylethenyl, 2-propen-1-yl, 3-buten-1-yl, 3-buten-2-yl, 7-octen-1-yl, 9-decen-1-yl, or 1,3-pentadien-1-yl. Preferred alkenyl groups herein contain from 2 to 20 carbon atoms. The term "cycloalkenyl" refers to cyclic, including polycyclic, unsaturated hydrocarbyl groups bonded by means of one carbon thereof and containing at least one double bond. Examples include 2-cyclopentene-1-yl, 2-cyclohexen-1-yl, 4-(2-cyclohexen-1-yl)-2-cyclohexen-1-yl, and 2,3-cyclopentadien-1-yl.

The term "alkynyl" as used herein refers to a branched or unbranched, acyclic hydrocarbyl group, typically although not necessarily, containing from 2 to 50 carbon atoms and at least one triple bond, such as ethynyl, 1-methylethynyl, 2-propynyl, 3-butyn-1-yl, 3-butyn-2-yl, 7-octyn-1-yl, and 9-decyn-1-yl. The term "cycloalkynyl" refers to cyclic, including polycyclic, unsaturated hydrocarbyl groups bonded by means of one carbon thereof and containing at least one triple bond. Examples include 2-cyclopentyne-1-yl, 2-cyclohexyn-1-yl, 3-cyclohexyn-1-yl, and 1,3-cyclohexadien-5-yne-2-yl.

The term "aromatic" or refers to a cyclic or polycyclic group that includes unsaturation that is delocalized across all ring atoms of at least one ring thereof. Multiple aromatic rings, if present, may be fused together or linked covalently through single atoms of each ring, optionally through a common group such as a methylene, ethylene or oxygen moiety. Examples include: phenyl, naphthalenyl, diphenyl, anthracenyl, pyridinyl, and phenanthrenyl. In particular embodiments, such groups include up to 50 atoms not counting hydrogen, typically 6 to 50 atoms not counting hydrogen, and specifically 6 to 16 atoms not counting hydrogen. Monovalent aromatic groups are referred to as aryl groups. Divalent aromatic groups are referred to as arylene groups. All isomers are included. For example, "naphthalenyl" includes 1-naphthalenyl and 2-naphthalenyl; "anthracenyl" includes 1-anthracenyl, 2-anthracenyl, and 5-anthracenyl, and "phenanthrenyl" includes 1-phenanthrenyl, 2-phenanthrenyl, 3-phenanthrenyl, 4-phenanthrenyl, and 5-phenanthrenyl.

The term "alkoxy" as used herein means an alkyl group bound through a single, terminal oxygen atom. An "alkoxy" group may be represented as —O-alkyl where alkyl is as defined above. The term "aryloxy" is used in a similar fashion, and may be represented as —O-aryl, with aryl as previously defined. The term "hydroxy" refers to —H.

Similarly, the term "alkylthio" as used herein means an alkyl group bound through a single, terminal sulfur atom. An "alkylthio" group may be represented as —S-alkyl where alkyl is as defined above. The term "arylthio" is used similarly, and may be represented as —S-aryl, with aryl as previously defined. The term "mercapto" refers to —SH.

The terms "halo", "halogen", and "halide" refer to a chloro, bromo, fluoro or iodo radicals, atoms or anions, respectively.

The terms "heterocycle" and "heterocyclic" refer to a cyclic compound or group in which one or more atoms in a ring are not carbon atoms. Fused ring compounds or radicals, including heteroaryl groups, as defined below, are included. Heterocyclic groups include saturated and unsaturated groups, including heterocycloalkyl, heterocycloalkenyl, and heteroaryl groups. Specific examples of heterocycles include pyrrolidine, pyrroline, furan, tetrahydrofuran, thiophene, imidazole, oxazole, thiazole, and indole, including all isomers. Additional heterocycles are described, for example, in Alan R. Katritzky, *Handbook of Heterocyclic Chemistry*, Pergammon Press, 1985, and in *Comprehensive Heterocyclic Chemistry*, 2d ed., A. R. Katritzky et al., eds., Elsevier, 1996. The term "metallocycle" refers to a heterocycle in which one or more of the heteroatoms in the ring or rings are metals.

The term "heteroaryl" refers to an aryl radical that includes one or more heteroatoms in at least one aromatic ring. Specific heteroaryl groups include thiopheneyl, pyridinyl, pyridazinyl, pyrimidinyl, pyrazinyl, triazinyl, pyrazolyl, pyrrolyl, furanyl, thiazolyl, oxazolyl, imidazolyl, oxadiazolyl, triazolyl, indolyl, carbazolyl, benzofuranyl, and benzothiopheneyl.

More generally, the modifiers "hetero" and "heteroatom-containing", as in "heteroaryl" or "heteroatom-containing aromatic group" refer to a molecule or molecular fragment containing one or more heteroatoms. The term "heteroalkyl" refers to an alkyl group bonded by means of a carbon atom thereof to the remainder of the compound or complex, and containing one or more heteroatom containing substituents. Examples include chloroalkyl or hydroxymethyl, but not alkoxy groups. When the term "heteroatom-containing" introduces a list of possible heteroatom-containing groups, it is intended that the term apply to every member of that group. That is, the phrase "heteroatom-containing alkyl, alkenyl and alkynyl" is to be interpreted as "heteroatom-containing alkyl, heteroatom-containing alkenyl and heteroatom-containing alkynyl." The term "heterocarbon" refers to a group consisting only of carbon and heteroatoms, for example, fluorocarbon, refers to a group containing only carbon and fluorine. Heteroaryl groups may be bonded to the remainder of the compound or complex by means of a heteroatom.

By "divalent" as in "divalent hydrocarbyl", "divalent alkyl", or "divalent aryl", is meant that the hydrocarbyl, alkyl, or aryl moiety contains two separate electronic interactions (bonds) with additional atoms or groups. The interactions may be through the same or different atoms. Examples include two covalent bonds, a double bond, a covalent bond and a π-bond, or two π-bonds. "Trivalent", "tetravalent" and similar terms refer to groups possessing three, four or more such interactions, respectively. The term "inert" as in "inertly substituted" refers to any substituent or component that does not adversely react or interfere with the synthesis or any subsequent desired reaction or use of the ligand or compound.

As used herein the term "silane" refers to $SiZ^1Z^2Z^3Z^4$, where each of $Z^1$, $Z^2$, $Z^3$, and $Z^4$ is independently hydrogen, hydrocarbyl, heteroatom-containing hydrocarbyl, heterocarbyl, or a combination thereof. Similarly, "silyl" refers to —$SiZ^1Z^2Z^3$, "borane" refers to $BZ^1Z^2Z^3$, "boryl" refers to the —$BZ^1Z^2$ group, "phosphine" refers to: $PZ^1Z^2Z^3$, "phosphino" refers to the group —$PZ^1Z^2$, "amine" refers to: $NZ^1Z^2Z^3$, and "amino" refers to the —$NZ^1Z^2$, where each of $Z^1$, $Z^2$ and $Z^3$ is as defined above. When the heteroatom is joined to a metal or metalloid, the foregoing phosphorus and nitrogen containing radicals are renamed as "phosphido" and "amido" groups, respectively.

Other abbreviations used herein include: "Pr" to refer to isopropyl; "Bu" to refer to tert-butyl; "Me" to refer to methyl; "Et" to refer to ethyl; "Ph" to refer to phenyl; "Ms" to refer to mesityl (2,4,6-trimethylphenyl); "TFA" to refer to trifluoroacetate; "THF" to refer to tetrahydrofuran; "Ts" refers to toluenesulfonyl; "Tf" refers to trifluoromethanesulfonyl; "Ac" refers to acetate; "Bz" refers to benzyl; "Ar" refers to aryl; "aralkyl" refers to arylalkyl; and "Cbz" refers to N-carbazole (specifically the N-dibenzopyrrolyl ligand).

The term "vinylidene aromatic monomer", refers to organic compounds comprising ethylenic unsaturation corresponding to the formula: $CR''_2=CR'''R^*$, wherein R" independently each occurrence is hydrogen, halogen, or optionally substituted —$C_{1-20}$ hydrocarbyl, heterohydrocarbyl, or heterocarbyl, preferably hydrogen;

R'" is hydrogen, halogen, or optionally substituted —$C_{1-20}$ hydrocarbyl, heterohydrocarbyl, or heterocarbyl, preferably hydrogen or methyl; and R* is an aromatic hydrocarbyl- or substituted hydrocarbyl group, preferably phenyl, biphenyl, p-vinylphenyl, chlorophenyl or tolyl (including all isomers individually or in any combination).

The metal complexes according to the invention are prepared by contacting a metal compound (precursor) with a source of the polydentate heteroatom containing ligand. Preferred ligand sources are neutral compounds according to the following formula:

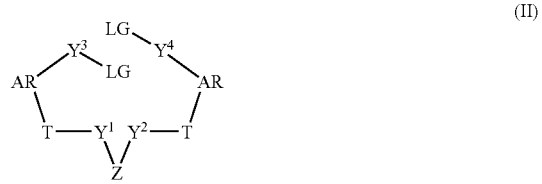

(II)

wherein LG is a leaving group having up to 10 atoms, that allows for complex formation, that is joining of the ligand to the remnant of the metal compound; and Z, $Y^1$, $Y^2$, $Y^3$, $Y^4$, Z each AR and T are as previously defined with respect to formula I. In a preferred embodiment, LG is H, lithium, butylmagnesium, or similar leaving group well understood by those of skill in the art.

In other embodiments, the ligand source of this invention are compounds characterized by the formula:

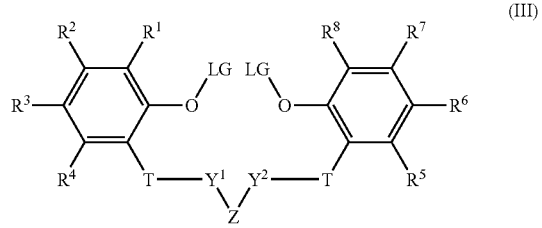

(III)

wherein $R^1$-$R^8$ are each independently selected from the group consisting of hydrogen, halogen, hydrocarbyl, substituted hydrocarbyl, heterohydrocarbyl, hydrocarbyloxy, substituted hydrocarbyloxy, silyl, siloxy, boryl, dihydrocarbylphosphino, substituted dihydrocarbylphosphino, dihydrocarbylamino, substituted dihydrocarbylamino, hydrocarbylthio, substituted hydrocarbylthio, combinations thereof, and multiple ring including fused ring derivatives of the foregoing, said substituent having up to 50 atoms in total. In addition, any two or more selected from $R^1$-$R^4$ or $R^5$-$R^8$ may be linked together to form one or more multiple ring structures or linked together with T, $Y^1$ or $Y^2$ and/or Z. It is preferred generally that $R^1$ and/or $R^8$ are not hydrogen. In some embodiments, neither $R^1$ nor $R^8$ are hydrogen. In general, z, $Y^1$, $Y^2$, T, and LG are as previously defined with respect to formula I. Highly desirably $Y^1$ and $Y^2$ are both oxygen or sulfur, most preferably sulfur.

In a preferred embodiment, $R^1$ and $R^8$ are independently selected from the group consisting of hydrocarbyl, substituted hydrocarbyl and heterohydrocarbyl. Specific $R^1$ and $R^8$ groups include: benzyl, phenyl, t-butyl, naphthyl, 2-biphenyl, 2-dimethylaminophenyl, 2-methoxyphenyl, anthracenyl, mesityl, 2-pyridyl, 3,5-dimethylphenyl, 3,5-di(t-butyl)phenyl, o-tolyl, phenanthrenyl, 2,6-di(isopropyl)phenyl, 2,4,6-tri(methyl)phenyl, 2,4,6-tri(isopropyl)phenyl, N-dibenzopyrrolyl, N-2,3,4,5-di(4-t-butylbenzo)pyrrolyl, 2-ethyl-4,5-benzofuran-3-yl, 4,5-benzothiophen-3-yl, 1,2-oxazol-5-yl, and 1-methyl-3a,7a-benzopyrrol-4-yl. Most preferably, $R^1$ and $R^8$ are both N-dibenzopyrrolyl. In some such embodiments, $R^3$ and $R^6$ are independently selected from the group consisting of alkyl, substituted alkyl, aryl and substituted aryl. Examples of suitable $R^3$ and $R^6$ groups include methyl, benzyl, phenyl, naphthyl, 2-biphenyl, 2-dimethylaminophenyl, 2-methoxyphenyl, anthracenyl, mesityl, 2-pyridyl, 3,5-dimethylphenyl, o-tolyl, phenanthrenyl, 2,6-di(isopropyl)phenyl, 2,4,6-tri(isopropyl)phenyl, and tert-butyl.

In a further preferred embodiment each T is methylene or substituted methylene, that is a moiety of the formula: —$CR^{22}_2$—, wherein each $R^{22}$ substituent is hydrogen, halogen, hydrocarbyl, or substituted hydrocarbyl of up to 20 atoms.

The ligand sources defined in formulas I, II and III can be further defined by specifying the group Z, such that Z is selected from the group consisting of optionally substituted hydrocarbylene and silanediyl groups. Preferably, Z corresponds to the formula: -$(Q'R^{30}_2)_{m'}$—, wherein, Q', independently each occurrence, is selected from the group consisting of carbon and silicon, each $R^{30}$ is selected from the group consisting of hydrogen, halogen, hydrocarbyl, and substituted hydrocarbyl, said group having from 1 to 50 atoms, and optionally two or more $R^{30}$ substituents on the same or different Q' atoms, may be joined into a ring or multiple ring structure, and m' is an integer from 1 to 10, preferably from 1-5. Highly desirably at least one $R^{30}$ substituent is not hydrogen.

Examples of suitable Z groups include: —$(CH_2)$—, —$(CH_2)_2$—, —$(CH_2)_3$—, —$(CH_2)_4$—, —$(CH(CH_3))$—, —$(CH(CH_3))_2$—, —$(C(CH_3)_2)$—, —$(C(CH_3)_2)_2$—, —$(C(CH_3)_2)_3$—, —$CH_2CH(CH_3)CH_2$—, —$CH_2C(CH_3)_2CH_2$—, —$CH_2CH(C_6H_5)CH_2$—, —$CH(CH_3)CH_2CH(CH_3)$—, —$Si(CH_3)_2$—, —$Si(C_6H_5)_2$—, —$CH(C_2H_5)CH_2CH(C_2H_5)$—, —$CH(CH_3)CH_2CH_2CH(CH_3)$—, —$CH(C_6H_5)CH_2CH(C_6H_5)$—,

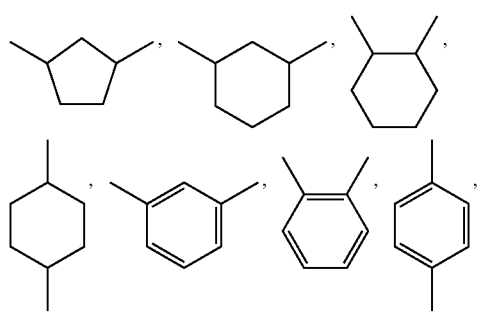

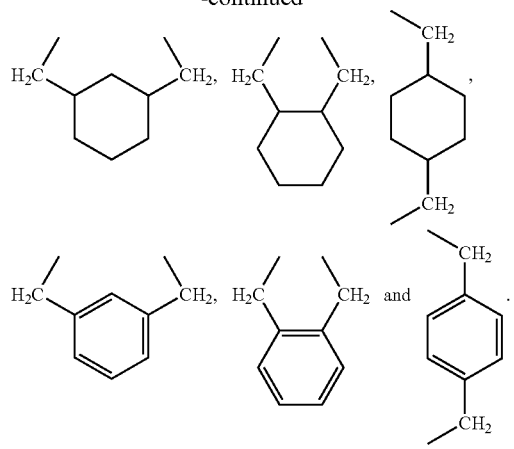

The ligand sources employed in the invention are commercially available or they may be prepared using known procedures, such as those described, for example, in March, *Advanced Organic Chemistry*, Wiley, New York 1992 (4th Ed.), and in Katritzky et al., *Comprehensive Heterocyclic Chemistry*, Elsevier, New York 1984 (1st Ed.) and 1996 (2nd Ed.). One general method is shown below in scheme 1:

Scheme 1

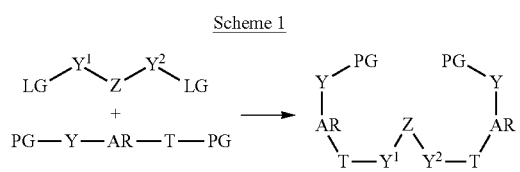

As shown in scheme 1, the ligands may be prepared by displacement of a group, LG, from an appropriate dinucleophile (LG-$Y^1$—Z—$Y^2$-LG), wherein LG, AR, T, $Y^1$, Z, and $Y^2$ are as previously defined, Y is $Y^3$ or $Y^4$, and PG is hydrogen or a protecting group, which may later by replaced by a leaving group, LG, to form the ligand source of formula (I). Examples of suitable protecting groups are disclosed in: *Protecting Groups in Organic Synthesis*, Wiley, New York 1999 (3rd Ed.). Preferably, LG is selected from the group consisting of halogen, mesylate, tosylate, triflate (trifluoromethanesulfonate), and acetate. Additionally, PG is preferably hydrogen, Li$^+$, or a Grignard remnant. A preferred PG group is H or trimethylsilyl.

Another general ligand synthesis method is shown below in scheme 2 wherein one Y' group is already present in the electrophile:

Scheme 2

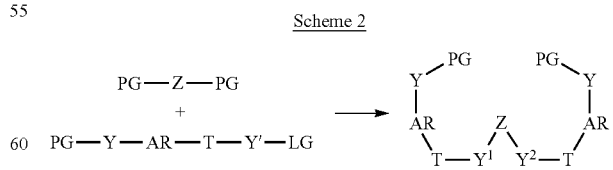

In scheme 2, Y may be $Y^3$ or $Y^4$ and Y' may be $Y^1$ or $Y^2$. Preferably all $Y^1$—$Y^4$ are oxygen or sulfur, and the remaining variables are the same as those discussed previously with respect to Scheme 1. In a preferred embodiment, the synthesis of scheme 2 is an alkylation of Y' with an appropriate divalent alkylating agent, G-Z-G, where —Z— is alkylene or arylene. Another suitable synthetic method for preparing the ligand sources for use herein involves the reaction of an o-quinone methide (o-QM), as shown in scheme 3:

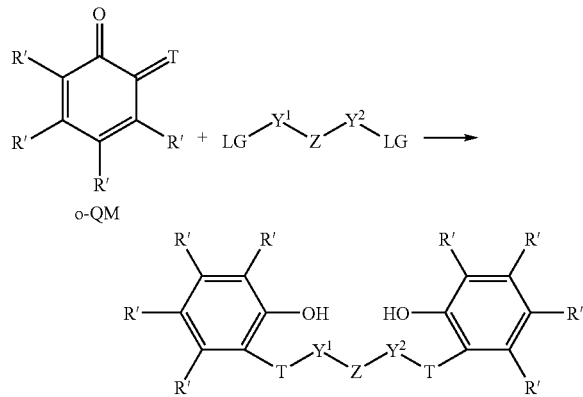

In scheme 3, each R' is $R^1$-$R^8$, T is $=CR^{22}_2$ where $R^{22}$ is a previously defined with respect to formula III, and LG, $Y^1$, $Y^2$, and Z are as previously defined. In a preferred embodiment T is $CH_2$, $Y^1$ and $Y^2$ are each oxygen, Z is alkylene, and LG is H, $Li^+$ or a Grignard remnant. Generation of quinine methide reagents is well known to the skilled artisan and described in such references as *Tetrahedron*, 2002, 58, 5367-5405.

Specific examples of suitable ligand sources are compounds A1-A20 disclosed with respect to the examples herein.

The metal complexes of the invention are prepared by combining the desired ligand source with a metal compound (metal precursor) able to form the desired reaction product under appropriate reaction conditions. Generally the procedure involves use of an inert diluent, especially a hydrocarbon liquid, and inert reaction conditions, including nitrogen, helium or argon atmosphere, high vacuum, and the absence of Lewis bases such as water. In some embodiments, the present invention encompasses compositions that include any of the above-mentioned ligand sources in combination with an appropriate metal precursor compound and an optional activator. The product resulting from combining the ligand source and metal precursor compound need not be isolated prior to combination with an activator, if desired. For example, the ligand source may be added to a reaction vessel at the same time as the metal compound along with one or more activators, scavengers, monomers, or other reaction components. Additionally, the ligand source can be modified prior to addition to or after the addition of the metal precursor, for example through a deprotonation reaction or some other modification. Desirably however, the ligand source and metal precursor are reacted to form the desired metal complex which is isolated and optionally purified prior to further use as a catalyst component.

Suitable metal precursor compounds can be characterized by the general formula $M(L)_{n'}$ (Ia) or a dimeric or higher order derivative thereof, where M is a Groups 3-6 or Lanthanide metal, L is as previously defined with respect to formula I, and n'=n+2. Thus, in particular embodiments M can be selected from scandium, yttrium, titanium, zirconium, hafnium, vanadium, niobium, tantalum, chromium, molybdenum, tungsten, lanthanum, cerium, praseodymium, neodymium, samarium, europium, gadolinium, terbium, dysprosium, holmium, erbium, thulium, ytterbium, and lutetium. Preferably M is a Group 4 metal, most preferably Zr or Hf. Each L desirably is a ligand selected from the group consisting of hydride, halide, optionally substituted hydrocarbyl, heterohydrocarbyl, hydrocarbyloxy, hydrocarbylthio, trihydrocarbylboryl, trihydrocarbylsilyl, dihydrocarbylimido, dihydrocarbylphosphido, trihydrocarbylamino, trihydrocarbylpliosphino, ether, thioether, carboxylate, 1,3-dionate, carbonate, nitrate, borate, sulphate, and combinations thereof. Optionally, two or more L groups are joined into a ring or multiple ring structure. One or more of the ligands L may be ionically bonded to the metal M and, for example, L may be a non-coordinated or loosely coordinated or weakly coordinated anion. Suitable anionic ligands include those disclosed by Marks et al., *Chem. Rev.*, 2000, 100, 1391-1434. Preferably, L each occurrence is halide or hydrocarbyl, more preferably chloride, or a $C_{1-20}$ alkyl, aryl or aralkyl group.

Specific examples of suitable metal precursors include, but are not limited to $TiCl_4$, $Ti(CH_2Ph)_4$, $Ti(CH_2CMe_3)_4$, $Ti(CH_2SiMe_3)_4$, $Ti(CH_2Ph)_3Cl$, $Ti(CH_2CMe_3)_3Cl$, $Ti(CH_2SiMe_3)_3Cl$, $Ti(CH_2Ph)_2Cl_2$, $Ti(CH_2CMe_3)_2Cl_2$, $Ti(CH_2SiMe_3)_2Cl_2$, $Ti(NMe_2)_4$, $Ti(NEt_2)_4$, $Ti(O-{}^iPr)_4$, and $Ti(N(SiMe_3)_2)_2Cl_2$; $HfCl_4$, $Hf(CH_2Ph)_4$, $Hf(CH_2CMe_3)_4$, $Hf(CH_2SiMe_3)_4$, $Hf(CH_2Ph)_3Cl$, $Hf(CH_2CMe_3)_3Cl$, $Hf(CH_2SiMe_3)_3Cl$, $Hf(CH_2Ph)_2Cl_2$, $Hf(CH_2CMe_3)_2Cl_2$, $Hf(CH_2SiMe_3)_2Cl_2$, $Hf(NMe_2)_4$, $Hf(NEt_2)_4$, and $Hf(N(SiMe_3)_2)_2Cl_2$, $Hf(N(SiMe_3)CH_2CH_2CH_2N(SiMe_3))Cl_2$, $Hf(N(Ph)CH_2CH_2CH_2N(Ph))Cl_2$, $ZrCl_4$, $Zr(CH_2Ph)_4$, $Zr(CH_2CMe_3)_4$, $Zr(CH_2SiMe_3)_4$, $Zr(CH_2Ph)_3Cl$, $Zr(CH_2CMe_3)_3Cl$, $Zr(CH_2SiMe_3)_3Cl$, $Zr(CH_2Ph)_2Cl_2$, $Zr(CH_2CMe_3)_2Cl_2$, $Zr(CH_2SiMe_3)_2Cl_2$, $Zr(NMe_2)_4$, $Zr(NEt_2)_4$, $Zr(NMe_2)_2Cl_2$, $Zr(NEt_2)_2Cl_2$, $Zr(N(SiMe_3)_2)_2Cl_2$, $Zr(N(SiMe_3)CH_2CH_2CH_2N(SiMe_3))Cl_2$, and $Zr(N(Ph)CH_2CH_2CH_2N(Ph))Cl_2$. Lewis base adducts of these examples are also suitable as metal precursors, for example, ether, amine, thioether, and phosphine adducts, may be employed. Specific examples include $HfCl_4(THF)_2$, $HfCl_4(SMe_2)_2$ and $Hf(CH_2Ph)_2Cl_2(OEt_2)$. Ionic or zwitterionic metal precursor compounds, such as $[M(CH_2Ph)_3^+][B(C_6F_5)_4^-]$ or $[M(CH_2Ph)_3^+][PhCH_2B(C_6F_5)_3^-]$ where M is Zr or Hf, may be employed as well. The formation of such metal precursor compounds has been disclosed in Pellecchia et al., *Organometallics*, 1994, 13, 298-302; Pellecchia et al., *J. Am. Chem. Soc.*, 1993, 115, 1160-1162; Pellecchia et al., *Organometallics*, 1993, 13, 3773-3775 and Bochmann et al., *Organometallics*, 1993, 12, 633-640. The molar ratio of ligand source to metal precursor compound normally employed in preparation of the present metal complexes is typically in the range of about 0.01:1 to about 100:1, more specifically in the range of about 0.1:1 to about 10:1 and even more specifically about 1:2.

Generally, the ligand source (optionally modified as previously discussed) is mixed with a suitable metal precursor (and optionally other components, such as activators, scavengers, diluents, supports, shuttling agents, chain transfer agents, or sequestrants) prior to or simultaneously with any contact with monomers or other reagents involved in any subsequent use of the metal complexes. When the ligand source is mixed with the metal precursor compound, a metal-ligand complex may be formed, which may itself be an active catalyst or may be transformed into a catalyst upon contact with an activator. The complexation can be carried out using known methods, such as those described in U.S. Pat. No. 6,750,354 and other references. Recovery and optional purification of the metal complex, such as by recrystallization, may be employed if desired and is preferred for use herein.

Preferred metal complexes according to the invention are those wherein the ligand source is as defined with respect to formulas II or III, including all of the preferred embodiments of substituents previously identified. Accordingly, suitable metal complexes are those characterized by the following general formulas:

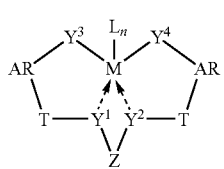
(IV)

wherein $Y^1$, $Y^2$, $Y^3$, $Y^4$, Z, T, M, L, and n are as previously defined with respect to formula I and Ia respectively, and AR is as previously defined with respect to formula III; and more preferably according to the following general formula

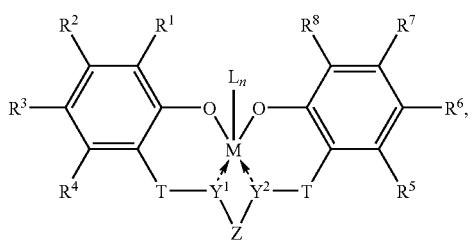
(V)

wherein M, L and n are as previously defined with respect to formula Ia, including preferred and most preferred embodiments thereof, and $R^1$-$R^8$ are each independently selected from the group consisting of hydrogen, halogen, hydrocarbyl, substituted hydrocarbyl, heterohydrocarbyl, hydrocarbyloxy, substituted hydrocarbyloxy, silyl, siloxy, boryl, dihydrocarbylphosphino, substituted dihydrocarbylphosphino, dihydrocarbylamino, substituted dihydrocarbylamino, hydrocarbylthio, substituted hydrocarbylthio, combinations thereof, and multiple ring including fused ring derivatives of the foregoing, said substituent having up to 50 atoms in total. In addition, any two or more selected from $R^1$-$R^4$ or $R^5$-$R^8$ may be linked together to form one or more multiple ring structures. It is preferred generally that $R^1$ and/or $R^8$ are not hydrogen. In some embodiments, neither $R^1$ nor $R^8$ are hydrogen. In general, z, $Y^1$, $Y^2$, and T are as previously defined with respect to formula I, and in particular the preferred embodiments thereof. Highly desirably $Y^1$ and $Y^2$ are both oxygen or sulfur, most preferably sulfur.

For the avoidance of doubt, preferably with respect to the metal complexes, $R^1$ and $R^8$ are independently selected from the group consisting of hydrocarbyl, substituted hydrocarbyl and heterohydrocarbyl. Specific $R^1$ and $R^8$ groups include: benzyl, phenyl, t-butyl, naphthyl, 2-biphenyl, 2-dimethylaminophenyl, 2-methoxyphenyl, anthracenyl, mesityl, 2-pyridyl, 3,5-dimethylphenyl, 3,5-di(t-butyl)phenyl, o-tolyl, phenanthrenyl, 2,6-di(isopropyl)phenyl, 2,4,6-tri(methyl)phenyl, 2,4,6-tri(isopropyl)phenyl, N-dibenzopyrrolyl, N-2,3,4,5-di(4-t-butylbenzo)pyrrolyl, 2-ethyl-4,5-benzofuran-3-yl, 4,5-benzothiophen-3-yl, 1,2-oxazol-5-yl, and J-methyl-3a,7a-benzopyrrol-4-yl. Most preferably, $R^1$ and $R^8$ are both N-dibenzopyrrolyl. In some such embodiments, $R^3$ and $R^6$ are independently selected from the group consisting of alkyl, substituted alkyl, aryl and substituted aryl. Examples of suitable $R^3$ and $R^6$ groups include: methyl, benzyl, phenyl, naphthyl, 2-biphenyl, 2-dimethylaminophenyl, 2-methoxyphenyl, anthracenyl, mesityl, 2-pyridyl, 3,5-dimethylphenyl, o-tolyl, phenanthrenyl, 2,6-di(isopropyl)phenyl, 2,4,6-tri(isopropyl)phenyl, and tert-butyl.

Also preferably, each T is methylene or substituted methylene, that is a moiety of the formula: $—CR^{22}_2—$, wherein each $R^{22}$ substituent is hydrogen, halogen, hydrocarbyl, or substituted hydrocarbyl of up to 20 atoms.

Additionally, Z is preferably selected from the group consisting of optionally substituted hydrocarbylene and silanediyl groups. More preferably, Z corresponds to the formula: $-(Q'R^{30}_2)_{m'}—$, wherein, Q', independently each occurrence, is selected from the group consisting of carbon and silicon, each $R^{30}$ is selected from the group consisting of hydrogen, halogen, hydrocarbyl, and substituted hydrocarbyl, said group having from 1 to 50 atoms, and optionally two or more $R^{30}$ substituents on the same or different Q' atoms, may be joined into a ring or multiple ring structure, and m' is an integer from 1 to 10, preferably from 1-5. Highly desirably at least one $R^{30}$ substituent is not hydrogen.

Examples of suitable Z groups in the complexes are: $—(CH_2)—$, $—(CH_2)_2—$, $—(CH_2)_3—$, $—(CH_2)_4—$, $—(CH(CH_3))—$, $—CH(CH_3))_2$, $—(C(CH_3)_2)—$, $—(C(CH_3)_2)_2—$, $—(C(CH_3)_2)_3—$, $—CH_2CH(CH_3)CH_2—$, $—CH_2C(CH_3)_2CH_2—$, $—CH_2CH(C_6H_5)CH_2—$, $—CH(CH_3)CH_2CH(CH_3)—$, $—Si(CH_3)_2—$, $—Si(C_6H_5)_2—$, $—CH(C_2H_5)CH_2CH(C_2H_5)—$, $—CH(CH_3)CH_2CH_2CH(CH_3)—$, $—CH(C_6H_5)CH_2CH(C_6H_5)—$, Highly preferred metal complexes are those of formula IV or V wherein $Y^1$, $Y^2$, $Y^3$ and $Y^4$ are each sulfur, wherein the dashed bonds between $Y^1$ and $Y^2$ and M are optional dative bonds; Z is a group having from 2 to 50 atoms, not counting hydrogen atoms; each AR is independently selected from the group consisting of optionally substituted aryl and heteroaryl; each T is group of the general formula: —(CR$^{20}_{2-x''}$)$_{x'}$—, wherein each R$^{20}$ substituent is independently selected from the group consisting of hydrogen and optionally substituted hydrocarbyl and heteroatom containing hydrocarbyl, x' is 1 or 2; and x" is 0 or 1; and wherein two or more R$^{20}$ substituents are optionally joined into a ring structure having from 3 to 50 atoms in the ring structure not counting hydrogen atoms, provided that when two or more R$^{20}$ substituents are joined into a ring structure, said ring structure is not an optionally substituted aryl or heteroaryl; M is a metal selected from the group consisting of groups 3-6 and lanthanides of the periodic table of elements; n is 1, 2, 3, 4, 5, or 6; and each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof.

In as much as the dashed arrows in formulas I, IV and V are optional bonds, it is to be understood by the skilled artisan that in some embodiments, these formulas can be written without either or both arrows. Proof of the different electronic interactions and/or isomers in a given metal complex may be obtained by proton NMR, $^{13}$C NMR, X-ray diffraction (for example, single crystal XRD), variable temperature spectroscopy, and combinations of such analytical techniques. Catalyst compositions according to the invention comprise one or more of the foregoing metal complexes (or the reaction product formed by combination of one or more ligand sources with one or more metal precursor compounds) along with one or more optional activators, and one or more additional optional components including scavengers, modifiers, chain transfer agents, supports, or diluents.

Suitable supports include silicas, aluminas, clays, zeolites, magnesium chloride, polymers, and organic particulated materials. Polymeric supports may be cross-linked or not. Suitable support materials include those disclosed in Hlatky, Chem. Rev., 2000, 100, 1347-1376 and Fink et al., Chem. Rev., 2000, 100, 1377-1390, and other sources. The metal complex or a composition comprising the same may be contacted with an activator (described below) before or after contact with the support; alternatively, the support may be contacted with the activator prior to contact with the metal complex or composition. In addition, the catalysts or metal complexes of this invention may be combined with other catalysts or metal complexes in a single reactor or in more than one reactor (parallel or serial) in order to form blends of polymer products.

The metal complexes and compositions typically are activated for use as polymerization catalysts by combination with a suitable activator or mixture of activators, although some of the ligand-metal complexes may be catalytically active (especially for oligomerization reactions) without use of an activator or activating technique. Broadly, the activator(s) may comprise alumoxanes, Lewis acids, Bronsted acids, compatible non-interfering activators, and combinations of the foregoing. These types of activators have been taught for use with different compositions or metal complexes in U.S. Pat. Nos. 5,599,761, 5,616,664, 5,453,410, 5,153,157, 5,064,802, EP-A-277,004, Marks et al., Chem. Rev., 2000, 100, 1391-1434, and elsewhere. In some embodiments, ionic or ion forming activators are preferred. In other embodiments, alumoxane activators are preferred.

Suitable activators may be represented by the following general formula:

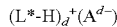

wherein L* is a neutral Lewis base; (L*-H)$^+$ is a Bronsted acid; A$^{d-}$ is a non-interfering, compatible anion having a charge of d–, and d is an integer from 1 to 3. More specifically A$^{d-}$ corresponds to the formula: (M$^{3+}$Q$_h$)$^{d-}$ wherein h is an integer from 4 to 6; h–3=d; M' is an element selected from group 13 of the periodic table; and Q is independently selected from the group consisting of hydrogen, dialkylamido, halogen, alkoxy, aryloxy, hydrocarbyl, and substituted-hydrocarbyl radicals (including halogen substituted hydrocarbyl, such as perhalogenated hydrocarbyl radicals), said Q having up to 20 carbons. In a more specific embodiment, d is one, i.e., the counter ion has a single negative charge and corresponds to the formula A$^-$.

Activators comprising boron or aluminum can be represented by the following general formula: (L*-H)$^+$(M"Q$_4$)$^-$, wherein:
L* is as previously defined; M" is boron or aluminum; and Q is a fluorinated C$_{1-20}$ hydrocarbyl group. Most specifically, Q is independently selected from the group consisting of fluorinated aryl group, such as a pentafluorophenyl group (i.e., a C$_6$F$_5$ group) or a 3,5-bis(CF$_3$)$_2$C$_6$H$_3$ group. Illustrative, but not limiting, examples of boron compounds which may be used as an activating cocatalyst in the preparation of the improved catalysts of this invention are tri-substituted ammonium salts such as: trimethylammonium tetraphenylborate, triethylammonium tetraphenylborate, tripropylammonium tetraphenylborate, tri(n-butyl)ammonium tetraphenylborate, tri(t-butyl)ammonium tetraphenylborate, N,N-dimethylanilinium tetraphenylborate, N,N-diethylanilinium tetraphenylborate, N,N-dimethylanilinium tetra-(3,5-bis(trifluoromethyl)phenyl)borate, N,N-dimethyl-(2,4,6-trimethylanilinium) tetraphenylborate, trimethylammonium tetrakis(pentafluorophenyl) borate, triethylammonium tetrakis(pentafluorophenyl)borate, tripropylammonium tetrakis(pentafluorophenyl)borate, tri(n-butyl)ammonium tetrakis(pentafluorophenyl) borate, tri(secbutyl)ammonium tetrakis(pentafluorophenyl) borate, N,N-dimethylanilinium tetrakis(pentafluorophenyl) borate, N,N-diethylanilinium tetrakis(pentafluorophenyl) borate, N,N-dimethyl-(2,4,6-trimethylanilinium) tetrakis(pentafluorophenyl) borate, trimethylammonium tetrakis-2,3,4,6-tetrafluorophenylborate and N,N-dimethylanilinium tetrakis-(2,3,4,6-tetrafluorophenyl) borate; dialkyl ammonium salts such as: di-(i-propyl)ammonium tetrakis(pentafluorophenyl) borate, and dicyclohexylammonium tetrakis(pentafluorophenyl) borate; and tri-substituted phosphonium salts such as: triphenylphosphonium tetrakis(pentafluorophenyl) borate, tri(o-tolyl)phosphonium tetrakis(pentafluorophenyl) borate, and tri(2,6-dimethylphenyl)phosphonium tetrakis(pentafluorophenyl) borate; N,N-dimethylanilinium tetrakis(3,5-bis(trifluoromethyl)phenyl)-borate; HNMe(C$_{18}$H$_{37}$)$_2^+$B(C$_6$F$_5$)$_4^-$; HNPh(C$_{18}$H$_{37}$)$_2^+$B(C$_6$F$_5$)$_4^-$: ((4-nBu-Ph)NH(n-hexyl)$_2$)$^+$B(C$_6$F$_5$)$_4^-$ and ((4-nBu-Ph)NH(n-decyl)$_2$)$^+$B(C$_6$F$_5$)$_4^-$. Specific (L*-H)$^+$ cations are N,N-dialkylanilinium cations, such as HNMe$_2$Ph$^+$, substituted N,N-dialkylanilinium cations, such as (4-nBu-C$_6$H$_4$)NH(n-C$_6$H$_{13}$)$_2^+$; (4-nBu-C$_6$H$_4$)NH(n-C$_{10}$H$_{21}$)$_2^+$ and HNMe(C$_{18}$H$_{37}$)$_2^+$. Specific examples of anions are tetrakis(3,5-bis(trifluoromethyl)phenyl)borate and tetrakis(pentafluorophenyl)borate. In some embodiments, the specific activator is PhNMe$_2$H$^+$B(C$_6$F$_5$)$_4^-$, HNMe(C$_{14-18}$H$_{29-37}$)$_2^+$B(C$_6$F$_5$)$_4^-$, HNMe$_2$(C$_{14-18}$H$_{29-37}$)$^+$B(C$_6$F$_5$)$_4^-$, or mixtures thereof.

Activators may comprise a salt of a cationic oxidizing agent and a non-interfering, compatible anion represented by the formula: $(Ox^{e+})_d(A^{d-})_e$, wherein:

$Ox^{e+}$ is a cationic oxidizing agent having a charge of e+; e is an integer from 1 to 3; and $A^{d-}$ and d are as previously defined. Examples of cationic oxidizing agents include: ferrocenium, hydrocarbyl-substituted ferrocenium, $Ag^+$, or $Pb^{+2}$. Specific embodiments of $A^{d-}$ are those anions previously defined with respect to the Bronsted acid containing activating cocatalysts, especially tetrakis(pentafluorophenyl)borate.

Another activator comprises a compound that is a salt of a carbenium ion or silyl cation and a non-interfering, compatible anion represented by the formula: $©^+A^-$, wherein: $©^+$ is a $C_{1-100}$ carbenium ion or silyl cation; and $A^-$ is as previously defined. A preferred carbenium ion is the trityl cation, i.e. triphenylcarbenium. The silyl cation may be characterized by the formula $Z^4Z^5Z^6Si^+$ cation, where each of $Z^4$, $Z^5$, and $Z^6$ is independently selected from the group consisting of hydrogen, halogen, and optionally substituted alkyl, alkenyl, alkynyl, heteroalkyl, heteroalkenyl, heteroalkynyl, aryl, heteroaryl, alkoxyl, aryloxyl, silyl, boryl, phosphino, amino, mercapto, alkylthio, arylthio, and combinations thereof. In some embodiments, a specified activator is $Ph_3C^+B(C_6F_5)_4^-$.

Activator may also comprise a compound that is a salt, which is represented by the formula $(A^{*+a})_b(Z^*J^*_j)^{-c}_d$ wherein A* is a cation of charge +a; Z* is an anion group of from 1 to 50, specifically 1 to 30 atoms, not counting hydrogen atoms, further containing two or more Lewis base sites; J* independently each occurrence is a Lewis acid coordinated to at least one Lewis base site of Z*, and optionally two or more such J* groups may be joined together in a moiety having multiple Lewis acidic functionality; j is a number form 2 to 12; and a, b, c, and d are integers from 1 to 3, with the proviso that a×b is equal to c×d. The foregoing compounds are disclosed in WO 99/42467. In other embodiments, the anion portion of these activators may be characterized by the formula $((C_6F_5)_3M''''\text{-LN-}M''''(C_6F_5)_3)^-$ where M'''' is boron or aluminum and LN is a linking group, which is specifically selected from the group consisting of cyanide, azide, dicyanamide and imidazolide. The cation portion is specifically a quaternary amine. See, e.g., LaPointe, et al., *J. Am. Chem. Soc.*, 2000, 122, 9560-9561.

Activators may include Lewis acids, such as those selected from the group consisting of tris(aryl)boranes, tris(substituted aryl)boranes, tris(aryl)alanes, tris(substituted aryl) alanes, including activators such as tris(pentafluorophenyl) borane. Other useful ion forming Lewis acids include those having two or more Lewis acidic sites, such as those described in WO 99/06413 or Piers, et al., *J. Am. Chem. Soc.*, 1999, 121, 3244-3245. Other useful Lewis acids will be evident to those of skill in the art. In general, the group of Lewis acid activators is within the group of ion forming activators (although exceptions to this general rule can be found) and the group tends to exclude the group 13 reagents listed below. Combinations of ion forming activators may be used.

Other general activators or compounds useful in a polymerization reaction may be used. These compounds may be activators in some contexts, but may also serve other functions in the polymerization system, such as alkylating a metal center or scavenging impurities. These compounds are within the general definition of "activator," but are not considered herein to be ion-forming activators. These compounds include a group 13 reagent that may be characterized by the formula $G^{13}R^{50}_{3-p}D_p$ where $G^{13}$ is selected from the group consisting of B, Al, Ga, In and combinations thereof, p is 0, 1 or 2, each $R^{50}$ is independently selected from the group consisting of hydrogen, halogen, and optionally substituted alkyl, alkenyl, alkynyl, heteroalkyl, heteroalkenyl, heteroalkynyl, aryl, heteroaryl, and combinations thereof, and each D is independently selected from the group consisting of halogen, hydrogen, alkoxy, aryloxy, amino, mercapto, alkylthio, arylthio, phosphino and combinations thereof. In other embodiments, the group 13 activator is an oligomeric or polymeric alumoxane compound, such as methylalumoxane and the known modifications thereof. Preferred examples include MMAO, MMAO—3A, MMAO—7 and PMAO—IP (all available from Akzo Nobel). Other examples are disclosed in, Barron, "*Alkylalumoxanes, Synthesis, Structure and Reactivity*", pp. 33-67 in *Metallocene-Based Polyolefins: Preparation, Properties and Technology*, J. Schiers and W. Kaminsky (eds.), Wiley Series in Polymer Science, John Wiley & Sons Ltd., Chichester, England, 2000, and references cited therein. In other embodiments, a divalent metal reagent may be used that is defined by the general formula $M'R^{50}_{2-p'}D_{p'}$ and p' is 0 or 1 in this embodiment and $R^{50}$ and D are as defined above. M' is the metal and is selected from the group consisting of Mg, Ca, Sr, Ba, Zn, Cd and combinations thereof. In still other embodiments, an alkali metal reagent may be used that is defined by the general formula $M^{iv}R^{50}$ and in this embodiment $R^{50}$ is as defined above. $M^{iv}$ is the alkali metal and is selected from the group consisting of Li, Na, K, Rb, Cs and combinations thereof. Additionally, hydrogen and/or silanes may be used in the catalytic composition or added to the polymerization system. Silanes may be characterized by the formula $SiR^{50}_{4-q}D_q$ where $R^{50}$ is defined as above, q is 1,2, 3 or 4 and D is as defined above, with the proviso that there is at least one D that is hydrogen.

A class of cocatalysts comprising non-coordinating anions generically referred to as expanded anions, further disclosed in U.S. Pat. No. 6,395,671, may be suitably employed to activate the metal complexes of the present invention for olefin polymerization. Generally, these cocatalysts (illustrated by those having imidazolide, substituted imidazolide, imidazolinide, substituted imidazolinide, benzimidazolide, or substituted benzimidazolide anions) may be depicted as follows:

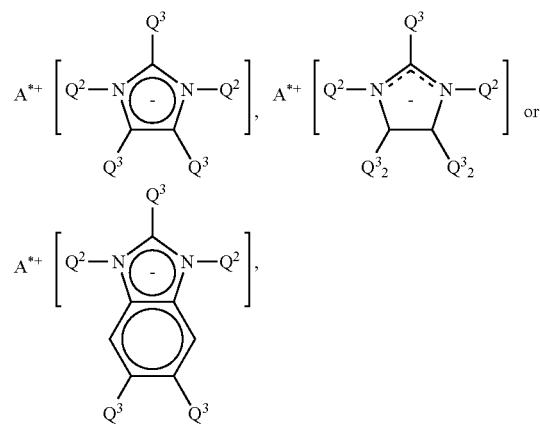

wherein:

A*+ is a cation, especially a proton containing cation, and preferably is a trihydrocarbyl ammonium cation containing one or two $C_{10-40}$ alkyl groups, especially a methyldi($C_{14-20}$ alkyl)ammonium cation, $Q^3$ independently each occurrence, is hydrogen or a halo, hydrocarbyl, halocarbyl, halohydrocarbyl, silylhydrocarbyl, or silyl, (including mono-, di- and tri(hydro-carbyl)silyl) group of up to 30 atoms not counting hydrogen, preferably $C_{1-20}$ alkyl, and $Q^2$ is tris(pentafluorophenyl)borane or tris(pentafluorophenyl)alumane).

Examples of these catalyst activators include trihydrocarbylammonium-salts, especially, methyldi(C14-20 alkyl)ammonium-salts of:

bis(tris(pentafluorophenyl)borane)imidazolide, bis(tris(pentafluorophenyl)borane)-2-undecylimidazolide, bis(tris(pentafluorophenyl)borane)-2-heptadecylimidazolide, bis(tris(pentafluorophenyl)borane)-4,5-bis(undecyl)imidazolide, bis(tris(pentafluorophenyl)borane)-4,5-bis(heptadecyl)imidazolide, bis(tris(pentafluorophenyl)borane)imidazolinide, bis(tris(pentafluorophenyl)borane)-2-undecylimidazolinide, bis(tris(pentafluorophenyl)borane)-2-heptadecylimidazolinide, bis(tris(pentafluorophenyl)borane)-4,5-bis(undecyl)imidazolinide, bis(tris(pentafluorophenyl)borane)-4,5-bis(heptadecyl)imidazolinide, bis(tris(pentafluorophenyl)borane)-5,6-dimethylbenzimidazolide, bis(tris(pentafluorophenyl)borane)-5,6-bis(undecyl)benzimidazolide, bis(tris(pentafluorophenyl)alumane)imidazolide, bis(tris(pentafluorophenyl)alumane)-2-undecylimidazolide, bis(tris(pentafluorophenyl)alumane)-2-heptadecylimidazolide, bis(tris(pentafluorophenyl)alumane)-4,5-bis(undecyl)imidazolide, bis(tris(pentafluorophenyl)alumane)-4,5-bis(heptadecyl)imidazolide, bis(tris(pentafluorophenyl)alumane)imidazolinide, bis(tris(pentafluorophenyl)alumane)-2-undecylimidazolinide, bis(tris(pentafluorophenyl)alumane)-2-heptadecylimidazolinide, bis(tris(pentafluorophenyl)alumane)-4,5-bis(undecyl)imidazolinide, bis(tris(pentafluorophenyl)alumane)-4,5-bis(heptadecyl)imidazolinide, bis(tris(pentafluorophenyl)alumane)-5,6-dimethylbenzimidazolide, and bis(tris(pentafluorophenyl)alumane)-5,6-bis(undecyl)benzimidazolide.

Other activators include those described in PCT publication WO 98/07515 such as tris(2,2',2"-nonafluorobiphenyl)fluoroaluminate. Combinations of activators are also contemplated by the invention, for example, alumoxanes and ionizing activators in combinations, see for example, EP-A-0 573120, PCT publications WO 94/07928 and WO 95/14044 and U.S. Pat. Nos. 5,153,157 and 5,453,410. WO 98/09996 describes activating catalyst compounds with perchlorates, periodates and iodates, including their hydrates. WO 99/18135 describes the use of organoboroaluminum activators. WO 03/10171 discloses catalyst activators that are adducts of Bronsted acids with Lewis acids. Other activators or methods for activating a catalyst compound are described in for example, U.S. Pat. Nos. 5,849,852, 5,859,653, 5,869,723, EP-A-61 5981, and PCT publication WO 98/32775. All of the foregoing catalyst activators as well as any other know activator for transition metal complex catalysts may be employed alone or in combination according to the present invention.

The molar ratio of metal:activator (whether a composition or complex is employed as a catalyst) employed specifically ranges from 1:10,000 to 100:1, more specifically from 1:5000 to 10:1, most specifically from 1:10 to 1:1. In one embodiment of the invention mixtures of the above compounds are used, particularly a combination of a group 13 reagent (scavenger) and an ion-forming activator. The molar ratio of group 13 reagent to ion-forming activator is specifically from 1:10,000 to 1000:1, more specifically from 1:5000 to 100:1, most specifically from 1:100 to 100:1. In another embodiment, the ion forming activators are combined with a group 13 reagent.

Another embodiment is a combination of the above compounds having about 1 equivalent of an optionally substituted N,N-dialkylanilinium tetrakis(pentafluorophenyl) borate, and 5-30 equivalents of a group 13 reagent. In some embodiments from about 30 to 2000 equivalents of an oligomeric or polymeric alumoxane activator, such as a modified alumoxane, for example, triisobutylaluminum modified methalumoxane, can be used.

The ligand sources, metal complexes and/or catalyst compositions of the invention can be used to catalyze a variety of transformations, including, for example, oxidation, reduction, hydrogenation, hydrosilylation, hydrocyanation, hydroformylation, polymerization, trimerization, oligomerization, carbonylation, isomerization, metathesis, carbon-hydrogen activation, carbon-halogen activation, cross-coupling, Friedel-Crafts acylation and alkylation, hydration, Diels-Alder reactions, Baeyer-Villiger reactions, and other transformations. Some compositions, complexes and/or catalysts according to the invention are particularly effective at polymerizing addition polymerizable monomers, especially ethylenically unsaturated monomers having up to 20 atoms not counting hydrogen, such as α-olefins (particularly ethylene, propylene, 1-butene, 1-pentene, 1-hexene, 1-heptene, 1-octene, styrene, mixtures thereof and mixtures of one or more of the preceding with a conjugated or nonconjugated diene monomer, especially butadiene or isoprene. Additional suitable monomers for use in homopolymerizations or copolymerizations include those having polar functionalities such as vinyl chloride, acrylic acid, methyl methacrylate, acrylonitrile, and ethyl acrylate as well as cyclic olefins or diolefins, 1,1-disubstituted olefins, and/or acetylenically unsaturated monomers.

In a preferred embodiment of the invention there is provide a method for producing polymers comprising in polymerized form one or more vinylidene aromatic monomers having selected properties in a coordination polymerization reaction, wherein one or more vinylidene aromatic monomers, especially styrene or a substituted styrene, are reacted either alone or with one or more other addition polymerizable monomers in the presence of a catalyst in a solution process. The catalysts used in this process are those discussed herein. The polymerization preferably occurs in a solution reactor at a reaction temperature greater than or equal to 100° C., more specifically greater than or equal to 110° C., even more specifically greater than or equal to 120° C., and still even more specifically greater than or equal to 130° C.

In accord with the knowledge of those of skill in the art, for purposes of this application, it will be understood that a coordination polymerization reaction will have occurred if one or more of the following tests are satisfied. The first test is whether the vinylidene aromatic polymer product shows isotacticity as determined by triad analysis using $^{13}C$ NMR spectroscopy. Another test is whether an interpolymer of an aliphatic α-olefin, especially ethylene, and one or more vinylidene aromatic monomers is formed having a measurable amount of said aliphatic α-olefin in the polymer. A final test indicating that coordination polymerization has occurred is if variations in catalyst structure can substantially vary the composition or molecular architecture of the resulting product. If one or more of these tests is met, it will be understood that a coordination polymerization reaction has occurred, despite the fact that products formed by other polymerization mechanisms (such as free radical, anionic or cationic mechanisms) may also form at the same time.

The polymer product is either a homopolymer or interpolymer including a measurable quantity of polymerized vinylidene aromatic monomer. Preferred polymers comprise at least 50 mole percent, more preferably at least 55 mole percent, even more preferably at least 60 mole percent polymerized vinylidene aromatic monomer. A particularly preferred product is a homopolymer of styrene.

Tacticity is determined using methods known to those of skill in the art, including measurement of the crystalline melting point or percent crystallinity, as well as triad content measurement. Generally, triad measurement is performed using $^{13}$C NMR, as described in *NMR and Macromolecules*, Randall Ed., Harwood et al., (1983). According to this technique, the integrated areas of mm triads representing an isotactic sequence in the spectrum, rr triads representing a syndiotactic sequence, and mr triads representing an atactic sequence are measured. The quantity of mm triads, represented as a percent of total mm, mr and rr triads indicates the isotacticity of the polymer while the quantity of rr triads, represented as a percent of total mm, mr and rr triads indicates the syndiotacticity of the polymer.

For ethylene copolymers the mr peak area is corrected by subtracting the integrated peak area for polymer formed from ethylene sequences. For copolymers with other monomers that produce peaks in the regions of the mm, mw, or rr triads, the integrals are similarly corrected by subtracting the intensity due to the interfering peak, or by other standard technique known in the art. For this purpose, these peaks may be identified by analysis of a series of interpolymers having various levels of comonomer incorporation, by literature assignments, by isotopic labeling, or by other means which are known in the art.

Stereo-errors and regio errors are similarly calculated by measuring the integrated area of a representative peak in the $^{13}$C NMR spectrum, or by averaging the areas of several peaks attributable to the presence of the error, optionally after correction due to overlapping peaks.

Preferred vinylidene aromatic polymer products in one embodiment of this invention possess a syndiotacticity (percent rr) less than 20 percent, preferably less than 10 percent, more preferably less than 5 percent. In some embodiments, isotacticity will be as high as 50 percent, more specifically as high as 80 percent, even more specifically as high as 90 percent, and even up to 100 percent. Generally, mr content (corrected if necessary due to comonomer content) fills the balance to 100 percent, and in some embodiments will be less than 50 percent, less than 25 percent and/or less than 10 percent. In certain polymers herein, the isotactic content (percent mm) is between 20 and 100; the percent syndiotactic content (percent rr) is between 0 and 30 and is less than the isotactic content; and the mr content is the balance to total 100 percent. In other embodiments, the isotactic content is between 20 and 80 percent; the syndiotactic content is between 0 and 30 percent and is less than the isotactic content; and the mr content constitutes the balance. In another specific embodiment, the isotacticity is less than or equal to 25 percent, the syndiotacticity is less than the isotacticity, and the percent mr is equal to the balance. In another specific embodiment, the isotacticity is at least 10 percent, the syndiotacticity is O, and the percent mr makes up the remainder up to 100 percent. As is known to the skilled artisan, the foregoing measurements of tacticity generally have an accuracy of plus or minus 5 percent.

The tacticity, stereo-error content and/or regio-error content of the resulting polymers can be altered by varying the ligand sources and/or metal complexes employed in this invention and also by varying the process conditions. In some embodiments, $R^1$ and $R^8$ are varied and in some embodiments, Z is varied. Generally, $R^1$ and $R^8$ are optionally substituted aryl, more specifically optionally substituted phenyl or N-dibenzopyrrolyl. In connection with varying the process conditions, it has been observed that a change in the reaction temperature of about 20° C. can change the stereo-error content, with a lower reaction temperature providing a polymer having less stereo-errors, and a higher reaction temperature providing a polymer having a greater stereo-error content.

Additionally, the selected properties can include a melting point, or lack of any appreciable melting point. Melting points are determined by differential scanning calorimetry, using methods known to those of skill in the art. Also, the selected properties can include a certain crystallinity, or lack of any appreciable crystallinity. Crystallinity is determined using X-ray diffraction methods known to those of skill in the art. Melting points and/or crystallinity measurements can be used to determine if the polymer product is amorphous. In some aspects, the tacticity is used in combination with the melting point and/or crystallinity to define the selected properties of the polymers of this invention. One desirable product is essentially amorphous, due to the presence of stereo-errors. Such polymers may lack a crystalline melting point in the DSC curve and/or evidence little or no crystallinity in the X-ray diffraction pattern, despite possessing a significant mm triad content of from 5 to 100 percent, and preferably little or no syndiotacticity, more preferably less than 5 percent syndiotacticity. In one embodiment of the present invention, a polystyrene homopolymer is produced having:

1. an isotactic structure (percent mm triads) between 35 and 95 percent, desirably, between 40 and 93 percent, more desirably between 40 and 90 percent, or most desirably between 40 and 85 percent;
2. a crystallinity as measured by DSC of 26 percent or less, preferably 13 percent or less, more preferably 5 percent or less;
3. a Mw/Mn in the range of 1.0-3.5, preferably 1.8-2.7, and most preferably 1.8-2.5; and
4. a Mw between 100,000 and 1,000,000, more preferably between 150,000 and 500,000, and most preferably between 250,000 and 500,000;

where DSC samples are scanned from room temperature to 250° C. with a heating rate of 1 deg/minute (first scan), then cooled from 250° C. to 30° C. at 1 deg/min (2nd scan) using air, and finally heated again to 250° C. at 1 deg/minute (3rd scan). Crystallization, if present, is determined by the existence of an endotherm in the heating scans or an exotherm in the cooling scan. The endothermic peaks in the temperature range of 150-250° C. are integrated using the software package supplied by the manufacturer to give the heat of fusion ($\Delta$Hf) in the units of J/g. Crystallinity is then calculated as: Percent Crystallinity=($\Delta$Hf/96)×100.

Desirable products according to the invention have a molecular weight from 100,000 to 1,000,000, and more specifically from 100,000 to 400,000. Other properties may include low specific gravity, high transparency and brilliance, high melt flow, and rapid crystal formation or no crystal formation.

Impact-modified vinylidene aromatic polymers may be prepared in one embodiment of the invention by copolymerization of a rubber forming monomer, such as a diene, in combination with one or more vinylidene aromatic monomers and optionally an aliphatic olefin. The polymerization may be performed in multiple reactors wherein in a first reactor a copolymer of the rubber forming monomer and one or more vinylidene aromatic monomers is prepared which product in the form of a slurry, solution or fluidized particles is then charged to a subsequent reactor operating in the substantial absence of a rubber forming monomer to prepare the desired polymer as a matrix of vinylidene aromatic polymer containing occlusions of the rubbery polymer. Highly desirably a copolymer of styrene and butadiene may be prepared and subsequently charged to a polymerization reactor for further polymerization of styrene or a mixture of styrene and ethylene or styrene and acrylonitrile.

Generally, polymerization is carried out under coordination polymerization conditions, including temperatures of from −100° C. to 300° C., preferably 30 to 200° C. and pressures from atmospheric to 1000 psi (7 MPa). Suspension, solution, slurry, powder bed, gas phase or high-pressure polymerization processes may be employed with the catalysts and compounds of this invention. Such processes can be run in a batch, semi-batch or continuous mode. Examples of such processes are well known in the art. A support, especially silica, alumina, or a polymer (especially polytetrafluoroethylene or a polyolefin) may be included in the catalyst composition as previously disclosed, and desirably is employed when the catalysts are used in a gas phase or slurry polymerization process. Preferably, the support is passivated before the addition of the catalyst. Passivation techniques are known in the art, and include treatment of the support with an organometallic compound such as organoaluminum compounds, especially trialkylaluminum compounds such as triethylaluminum. The support is preferably employed in an amount to provide a weight ratio of catalyst (based on metal):support from about 1:100,000 to about 1:10, more preferably from about 1:50,000 to about 1:20, and most preferably from about 1:10,000 to about 1:30. In most polymerization reactions, the molar ratio of catalyst:polymerizable compounds employed preferably is from about $10^{-12}$:1 to about $10^{-1}$:1, more preferably from about $10^{-9}$:1 to about $10^{-5}$:1.

Other additives that are useful in a polymerization reaction may be employed, such as scavengers, promoters, modifiers, shuttling and/or chain transfer agents, such as hydrogen, aluminum alkyls and/or silanes. The use of shuttling agents to prepare polymers having pseudo-block architecture or a mixture of properties has been previously disclosed in PCT application US/0508917, filed Mar. 17, 2005.

The molar ratio of catalyst/cocatalyst employed preferably ranges from 1:10,000 to 100:1, more preferably from 1:5000 to 10:1, most preferably from 1:1000 to 1:1. Alumoxane, when used by itself as an activating cocatalyst, is generally employed in large quantity, generally at least 100 times the quantity of metal complex on a molar basis. Tris(pentafluorophenyl)borane and tris(pentafluorophenyl)aluminum, where used as activating cocatalysts are preferably employed in a molar ratio to the metal complex of from 0.5:1 to 10:1, more preferably from 1:1 to 6:1 most preferably from 1:1 to 5:1. The remaining activating cocatalysts are generally employed in approximately equimolar quantity with the metal complex.

Suitable solvents for solution polymerization are inert liquids. Examples include, but are not limited to, straight and branched-chain hydrocarbons such as isobutane, butane, pentane, hexane, heptane, octane, and mixtures thereof; mixed aliphatic hydrocarbon solvents such as kerosene and ISOPAR™ (aliphatic hydrocarbon solvents available from ExxonMobil Chemicals, Inc.), cyclic and alicyclic hydrocarbons such as cyclohexane, cycloheptane, methylcyclohexane, methylcycloheptane, and mixtures thereof; perfluorinated hydrocarbons such as perfluorinated $C_{4-10}$ alkanes, and the like, and aromatic and alkyl-substituted aromatic compounds such as benzene, toluene, xylene, ethylbenzene and the like. Mixtures of the foregoing are also suitable.

The catalysts may be utilized in combination with at least one additional homogeneous or heterogeneous polymerization catalyst in separate reactors connected in series or in parallel to prepare polymer blends having desirable properties. Examples of such a process are disclosed in WO 94/00500, WO 94/17112 and U.S. Pat. No. 5,844,045.

The catalyst system may be prepared as a homogeneous catalyst by addition of the requisite components to a solvent in which polymerization will be carried out by solution polymerization procedures. The catalyst system may also be prepared and employed as a heterogeneous catalyst by adsorbing the requisite components on a catalyst support material such as silica gel, alumina or other suitable inorganic support material. When prepared in heterogeneous or supported form, it is preferred to use silica as the support material. The heterogeneous form of the catalyst system may be employed in a slurry polymerization. As a practical limitation, slurry polymerization takes place in liquid diluents in which the polymer product is substantially insoluble. Preferably, the diluent for slurry polymerization is one or more hydrocarbons with less than 5 carbon atoms. If desired, saturated hydrocarbons such as ethane, propane or butane may be used in whole or part as the diluent. Likewise the vinylidene aromatic monomer or a mixture of different vinylidene aromatic monomers may be used in whole or part as the diluent. Most preferably, the major part of the diluent comprises at least the vinylidene aromatic monomer or monomers to be polymerized.

At all times, the individual ingredients, as well as the resulting catalyst components, should be protected from oxygen and moisture. Therefore, the catalyst components and catalysts should be prepared and recovered in an oxygen and moisture free atmosphere. Preferably, therefore, the reactions are performed in the presence of a dry, inert gas such as, for example, nitrogen or argon.

The polymerization may be carried out as a batch or a continuous polymerization process. A continuous process is preferred, in which event catalysts, solvent or diluent (if employed), and comonomers (or monomer) are continuously supplied to the reaction zone and polymer product continuously removed therefrom. The polymerization conditions for manufacturing the polymers are generally those useful in the solution polymerization process, although the invention is not limited thereto.

In some embodiments, the polymerization is conducted in a continuous solution polymerization system comprising two reactors connected in series or parallel. One or both reactors contain at least two catalysts which have a substantially similar comonomer incorporation capability but different molecular weight capability. In one reactor, a relatively high molecular weight product ($M_w$ from 100,000 to over 1,000,000, more preferably 200,000 to 500,000) is formed while in the second reactor a product of a relatively lower molecular weight ($M_w$ 2,000 to 300,000) is formed. The final product is a mixture of the two reactor effluents which are combined prior to devolatilization to result in a uniform mixing of the two polymer products. Such a dual reactor/dual catalyst process allows for the preparation of products with tailored properties. In one embodiment, the reactors are connected in series, that is the effluent from the first reactor is charged to the second reactor and fresh monomer, solvent and hydrogen or other molecular weight regulator (if desired) is added to the second reactor. Reactor conditions are adjusted such that the weight ratio of polymer produced in the first reactor to that produced in the second reactor is from 20:80 to 80:20. In addition, the temperature of the second reactor is controlled to produce the lower molecular weight product.

In one embodiment of the invention, a process for producing a styrene homopolymer or copolymer comprises one or more of the following steps: 1) providing controlled addition of a catalyst suited for preparing low molecular weight polymer (low molecular weight catalyst) to a reactor, optionally including a cocatalyst and a scavenger component; 2) providing controlled addition of a catalyst suited for preparing a high molecular weight polymer (high molecular weight catalyst) to the same reactor, optionally including a cocatalyst and a scavenger component; 3) continuously feeding styrene, optionally containing one or more comonomers into the reactor, optionally with a solvent or diluent, and optionally with a controlled amount of a molecular weight regulator, preferably hydrogen; 4) continuously feeding the low molecular weight catalyst into the reactor at a fixed rate; 5) continuously feeding the high molecular weight catalyst into the same reactor at a rate sufficient to produce the desired $M_w$ of the polymer product wherein the ratio of the molecular weight of the polymer produced by the high molecular weight catalyst to the molecular weight of the polymer produced by the low molecular weight catalyst ($M_{wH}/M_{wL}$) is in the range from about 1.5 to about 15; and 6) recovering the polymer product. Preferably, the process is a continuous solution process. The optional cocatalysts and scavenger components in the novel process can be independently mixed with each catalyst component before the catalyst components are introduced into the reactor, or they may each independently be fed into the reactor using separate streams, resulting in "in reactor" activation. Scavenger components are compounds that are capable of reaction with polar contaminants in the reactants of solvents. Suitable examples are known in the alt and include, but are not limited to, alkyl aluminum compounds, including alumoxanes. Preferred scavengers include trimethylaluminum, triethylaluminum, triisobutylaluminum, trioctylaluminum, and alumoxanes.

For the novel processes described herein, the polymer properties can be adjusted by control of process conditions. For a solution polymerization process, especially a continuous solution polymerization, preferred ranges of monomer concentration at steady state are from 0.25 to 20 percent of the total reactor contents, and the preferred range of polymer concentration is from 10 to 45 percent of the reactor contents.

In general, catalyst efficiency (expressed in terms of gram of polymer produced per gram of transition metal) decreases with increasing temperature and decreasing ethylene concentration. In addition, the molecular weight of the polymer product generally decreases with increasing reactor temperature. The molecular weight of the polymer can also be controlled with the addition of chain transfer compounds, especially through the addition of hydrogen.

The ligands, metal-ligand complexes and compositions of this invention can be prepared and tested for catalytic activity in one or more of the above reactions in a combinatorial fashion. Combinatorial chemistry generally involves the parallel or rapid serial synthesis and/or screening or characterization of compounds and compositions of matter. U.S. Pat. Nos. 5,985,356, 6,030,917 and WO 98/03521, generally disclose combinatorial methods suitable for use herein. In this regard, the ligand sources, metal precursor compounds, metal complexes and/or compositions according to the invention may be prepared and/or tested in rapid serial and/or parallel fashion, for example, in an array format. When prepared in an array format, ligand sources, metal complexes or compositions may take the form of an array comprising a plurality of compounds wherein each compound can be characterized by any of the above general formulas I, II, III, IV or V). An array of ligand sources may be synthesized using the procedures outlined previously. The array may also be of metal precursor compounds, the metal-ligand complexes or compositions characterized by the previously described formulae and/or descriptions. Typically, each member of the array will have at least one difference so that each member of the array may be distinguished from the other members of the array. Alternatively, one or more process variables may differ from region to region in the array.

In such a combinatorial array, typically each of the plurality of compositions or complexes has a different composition or stoichiometry, and typically each composition or complex is at a selected region on a substrate such that each compound is isolated from the effect of all other compositions or complexes. This isolation can take many forms, typically depending on the substrate used. If a flat substrate is used, there may simply be sufficient space between regions so that the compositions or complexes cannot interact. As another example, the substrate can be a microtiter or similar plate having wells so that each composition or complex is in a region separated from other compounds in other regions by a physical barrier. The array may also comprise a parallel reactor or testing chamber.

The array typically comprises at least 8 compounds, complexes or compositions each having a different chemical formula, meaning that there must be at least one different atom or bond differentiating the members in the array or different ratios of the components forming the array member. In other embodiments, there are at least 20 compounds, complexes or compositions on or in the substrate each having a different chemical formula or composition. In still other embodiments, there are at least 40 or 90 or 124 compounds, complexes or compositions on or in the substrate each having a different chemical formula or composition. Because of the manner of forming combinatorial arrays, it may be that each compound, complex or composition may not be worked-up, purified or isolated, and for example, may contain reaction by-products or impurities or unreacted starting materials.

The catalytic performance of the compounds, complexes or compositions of this invention can be tested in a combinatorial or high throughput fashion. In particular, polymerizations can also be performed using the technique disclosed in U.S. Pat. Nos. 6,306,658 and 6,508,984 or in WO 01/98371. As used herein, "catalytic performance" may be measured by the yield of polymer obtained, by the efficiency of polymer production, by tacticity, stereo-error and/or regio-error content of the polymer, by the crystallinity or lack thereof, by the molecular weight of molecular weight distribution (Mw/Mn) of the polymer, by the comonomer content of the resulting polymer, or by the elasticity or any other desired property of factor of the resulting polymer.

Desirably, the ligand sources, metal complexes and/or catalyst compositions of the invention meet one or more desirable criteria for coordination polymerization of vinylidene aromatic monomers (alone or with other monomers), especially styrene or mixtures of styrene and ethylene. Highly desirably, the coordination polymerization of vinylidene aromatic monomers using the ligand sources, metal complexes and/or catalyst compositions of this invention is a solution polymerization operating at temperatures from 60 to 250° C., preferably 100 to 170° C.

The following specific embodiments of the invention and combinations thereof are especially desirable and hereby delineated in order to provide detailed disclosure for the appended claims.

1. A metal complex characterized by the formula:

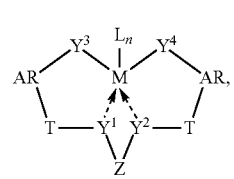

(I)

$Y^1$, $Y^2$, $Y^3$ and $Y^4$ is each independently selected from the group consisting of oxygen, phosphorus and sulfur, and optional donor bonds between $Y^1$ and M and between $Y^2$ and M are indicated by dashed arrows;

Z is a divalent group having up to 50 atoms, not counting hydrogen atoms;

each AR is a divalent aromatic group of up to 50 atoms, not counting hydrogen atoms;

each T is a group having up to 30 atoms total of the general formula: $-(CR^{20}_{2-x''})_{x'}-$, wherein each $R^{20}$ substituent is independently selected from the group consisting of hydrogen, halogen, hydrocarbyl, inertly substituted hydrocarbyl, and groups of the formula: $Q(R^{21})_y$, wherein $R^{21}$ is hydrogen, halogen, hydrocarbyl, or inertly substituted hydrocarbyl, Q is O, P, S, N, Si or B, and y is an integer from 1 to 3 equal to one less than the valence of Q; x' is 1 or 2; and x'' is 0 or 1; and optionally two or more $R^{20}$ substituents may be joined into a ring- or multiring-structure having from 3 to 50 atoms, provided that said ring structure is not an aromatic group;

M is a metal selected from the group consisting of Groups 3-6 and Lanthanides of the Periodic Table of the Elements;

n is a number from 1 to 6; and each L is a neutral, monovalent or divalent ligand containing up to 50 atoms not counting hydrogen.

2. The metal complex of embodiment 1 wherein M is a Group 4 metal and L, independently each occurrence, is hydrocarbyl or halide.

3. The metal complex of embodiment 1, characterized by the formula:

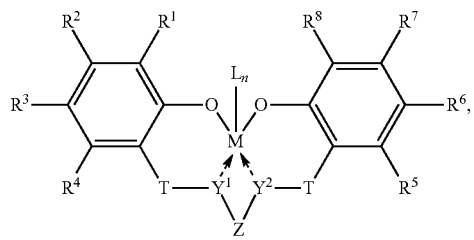

$R^1$-$R^8$ are each independently selected from the group consisting of hydrogen, halogen, hydrocarbyl, substituted hydrocarbyl, heterohydrocarbyl, hydrocarbyloxy, substituted hydrocarbyloxy, silyl, siloxy, boryl, dihydrocarbylphosphino, substituted dihydrocarbylphosphino, dihydrocarbylamino, substituted dihydrocarbylamino, hydrocarbylthio, substituted hydrocarbylthio, combinations thereof, and multiple ring including fused ring derivatives of the foregoing, said substituent having up to 50 atoms in total, and, any two or more selected from $R^1$-$R^4$ or $R^5$-$R^8$ may be linked together to form one or more multiple ring structures; and M, L, n, T, $Y^1$, $Y^2$ and Z are as previously defined in embodiment 1.

4. A metal complex according to embodiment 1 wherein each T is a moiety of the formula: $-CR^{22}_{2'}-$, wherein each $R^{22}$ substituent is hydrogen, halogen, hydrocarbyl, or substituted hydrocarbyl of up to 20 atoms.

5. A metal complex according to embodiment 1 wherein Z corresponds to the formula: $-(Q'R^{30}_2)_{m'}-$, wherein, Q', independently each occurrence, is selected from the group consisting of carbon and silicon, each $R^{30}$ is selected from the group consisting of hydrogen, halogen, hydrocarbyl, and substituted hydrocarbyl, said group having from 1 to 50 atoms, and optionally two or more $R^{30}$ substituents on the same or different Q' atoms, may be joined into a ring or multiple ring structure, and m' is an integer from 1 to 10.

6. A metal complex according to embodiment 5 wherein Z is selected from the group consisting of: $-(CH_2)-$, $-(CH_2)_2-$, $-(CH_2)_3-$, $-(CH_2)_4-$, $-(CH(CH_3))-$, $-(CH(CH_3))_2-$, $-(C(CH_3)_2)-$, $-(C(CH_3)_2)_2-$, $-(C(CH_3)_2)_3-$, $-CH_2CH(CH_3)CH_2-$, $-CH_2C(CH_3)_2CH_2-$, $-CH_2CH(C_6H_5)CH_2-$, $-CH(CH_3)CH_2CH(CH_3)-$, $-Si(CH_3)_2-$, $-Si(C_6H_5)_2-$, $-CH(C_2H_5)CH_2CH(C_2H_5)-$, $-CH(CH_3)CH_2CH_2CH(CH_3)-$, $-CH(C_6H_5)CH_2CH(C_6H_5)-$,

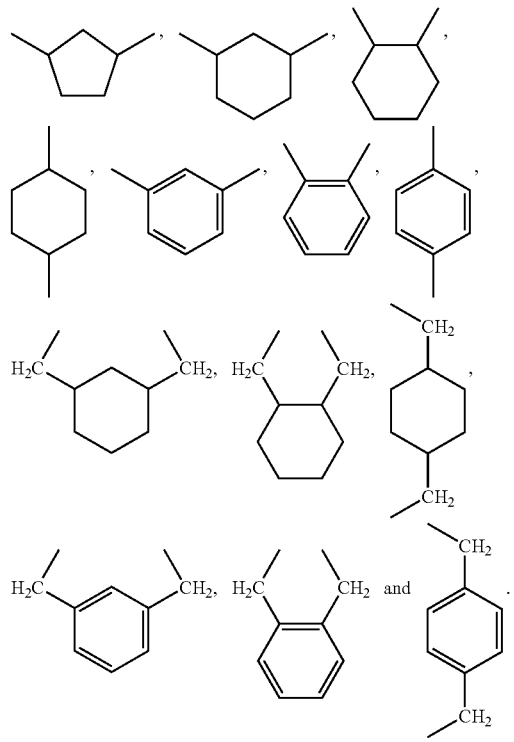

7. A metal complex according to embodiment 1 wherein each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof.

8. A composition comprising the reaction product or mixture resulting from contacting a ligand source characterized by the formula:

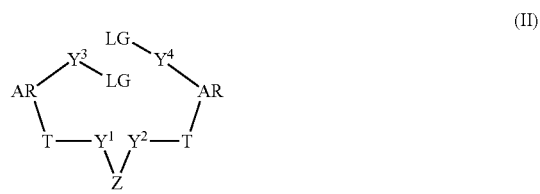

(II)

wherein LG is a leaving group having up to 10 atoms;

$Y^1$, $Y^2$, $Y^3$ and $Y^4$ is each independently selected from the group consisting of oxygen, phosphorus and sulfur;

Z is a divalent group having up to 50 atoms, not counting hydrogen atoms;

each AR is a divalent aromatic group of up to 50 atoms, not counting hydrogen atoms;

each T is a group having up to 30 atoms total of the general formula: $-(CR^{20}_{2-x''})_{x'}-$, wherein each $R^{20}$ substituent is independently selected from the group consisting of hydrogen, halogen, hydrocarbyl, inertly substituted hydrocarbyl, and groups of the formula: $Q(R^{21})_y$, wherein $R^{21}$ is hydrogen, halogen, hydrocarbyl, or inertly substituted hydrocarbyl, Q is O, P, S, N, Si or B, and y is an integer from 1 to 3 equal to one less than the valence of Q; x' is 1 or 2; and x" is 0 or 1; and optionally two or more $R^{20}$ substituents may be joined into a ring- or multiring-structure having from 3 to 50 atoms, provided that said ring structure is not an aromatic group; with a metal compound corresponding to the formula: $M(L)_{n'}$, or a dimeric or higher order derivative thereof, where M is a Group 3-6 or Lanthanide metal;

each L is a neutral, monovalent or divalent ligand containing up to 50 atoms not counting hydrogen; and n' is a number from 3 to 8.

9. A method for forming an oligomeric or polymeric product, comprising contacting one or more addition polymerizable monomers with a catalyst comprising a metal complex or composition according to any of embodiments 1 to 8 and, optionally, an activator.

10. The method of embodiment 9, wherein the monomer is an ethylenically unsaturated compound containing from 2 to 20 atoms not counting hydrogen.

11. The method of embodiment 10, wherein the product is a polymer and the monomer is propylene or a vinylidene aromatic monomer.

12. The method of embodiment 11 wherein the vinylidene aromatic monomer is styrene.

13. The method of embodiment 11 which is a solution polymerization reactor conducted at a temperature greater than or equal to 100° C., and wherein the resulting polymer has a rr triad content of less than 30 percent and a mm triad content from 25 to 100 percent.

14. The method of embodiment 11 wherein the polymer has no appreciable melting point as determined by DSC.

15. The method of any one of embodiments 12 or 13, wherein the polymer is substantially amorphous due to the presence of stereo- and/or regio-errors in the polymer structure.

16. The method of embodiment 12, conducted at a temperature from 10 to 170° C.

17. A method for forming an oligomeric or polymeric product comprising in polymerized form one or more vinylidene aromatic monomers, said process comprising contacting a monomer mixture comprising one or more vinylidene aromatic monomers with a catalyst composition comprising a metal complex and optionally, an activator, under solution polymerization conditions in a reactor at a temperature greater than or equal to 100° C., and wherein the resulting polymer has a rr triad content of less than 30 percent and a mm triad content from 25 to 100 percent.

18. The method of embodiment 17 wherein a polymer having no appreciable melting point as determined by DSC is formed.

19. The method of embodiment 18, wherein the polymer is substantially amorphous due to the presence of stereo- and/or regio-errors in the polymer structure.

20. The method of embodiment 17, conducted at a temperature from 110 to 170° C.

21. The method of embodiment 17, wherein the polymer comprises at least 50 mole percent of polymerized vinylidene aromatic monomer.

22. The method of embodiment 21, wherein the polymer consists essentially of polymerized vinylidene aromatic monomer.

23. The method of embodiment 21 or 22, wherein the vinylidene aromatic monomer is styrene.

24. A polymer comprising in polymerized form one or more vinylidene aromatic monomers having a rr triad content of less than 30 percent and a mm triad content from 25 to 100 percent.

25. A polymer according to embodiment 24 having no appreciable melting point as determined by DSC.

26. A polymer according to embodiment 24 wherein the vinylidene aromatic monomer is styrene.

27. A polymer according to embodiment 24 which is substantially amorphous due to the presence of stereo- and/or regio-errors in the polymer structure.

28. A polymer according to embodiment 24 consisting essentially of styrene in polymerized form.

It is understood that the present invention is operable in the absence of any component which has not been specifically disclosed and may be combined with any other suitable reaction or process in a multi-step polymerization system design. The following examples are provided in order to further illustrate the invention and are not to be construed as limiting. Unless stated to the contrary, all parts and percentages are expressed on a weight basis.

EXAMPLES

General: All air sensitive procedures are performed under a purified argon or nitrogen atmosphere in a Vacuum Atmospheres or MBraun glove box. All solvents are anhydrous, deoxygenated and purified according to known techniques. All ligand sources and metal precursors are prepared according to procedures known to those of skill in the art, for example, under inert atmosphere conditions, or purchased. All monomers used are anhydrous, deoxygenated and/or purified according to known techniques. Propylene polymerizations are carried out in a parallel pressure reactor, substantially as described in U.S. Pat. Nos. 6,306,658, 6,455,316, 6,489,168, 6,864,092, 6,787,112, 6,727,096, and 6,548,026. All glassware and disposable paddles are dried in a vacuum oven at 200° C. for at least 24 hours.

High temperature and room temperature size exclusion chromatography are performed using an automated "Rapid GPC" system as described in U.S. Pat. Nos. 6,491,816, 6,491,823, 6,475,391, 6,461,515, 6,436,292, 6,406,632, 6,175,409, 6,454,947, 6,260,407, and 6,294,388. A series of two 30 cm×7.5 mm linear columns are used, with both columns containing PL™ gel 10 µm, MixB (available from Polymer Labs). The GPC system is calibrated using narrow polystyrene standards. For high temperature testing, the system is operated at an eluent flow rate of 1.5 mL/min and an oven temperature of 160° C.; o-dichlorobenzene is used as the eluent. The polymer samples are dissolved 1,2,4-trichlorobenzene at a concentration of about 2.5 mg/mL and 200 µL of polymer solution are injected into the system. For room temperature testing, the system is operated at an eluent flow rate of 4.0 mL/min: toluene is used as the eluent; the polymer samples are dissolved toluene at 0.2-10 mg/mL concentration; and 50 µL of polymer solution are injected. The concentration of the polymer in the eluent is monitored using an evaporative light scattering detector. All of the molecular weight results obtained are relative to linear polystyrene standards.

Differential Scanning Calorimetry (DSC) measurements are performed on a DSC 2920 model instrument available from TA Instruments. A 10-30 mg polymer sample is deposited as a 200 mg/mL solution in 1,2,4-trichlorobenzene onto an aluminum substrate and dried under vacuum for 4 hours at 185° C. and allowed to cool to room temperature ("RT") overnight while under vacuum. The sample is then heated to 300° C. at a rate of 10° C./min while collecting heat flow data. Reported are the peak maxima of the melting transition.

High temperature NMR spectra are recorded on a Bruker 300 MHz spectrometer. $^{13}$C chemical shifts (75.47 MHz) are referenced relative to tetrachloro-ethane-$d_2$ solvent peaks. Polymer sample concentrations are 100-200 mg/ml. Acquisition parameters are 8196 scans; 30° pulse width; acquisition time=1.4 seconds; dl=4 seconds; 70-80° C. probe temperature. Tacticity of styrene polymers is determined using the 144-147 ppm region of the $^{13}$C NMR spectrum (phenyl C(1)), see, Randall, Ed., *NMR and Macromolecules*, Ch. 13: "Polystyrene and Epimerized Isotactic Polystyrenes" (1983). $^1$H NMR are also recorded on the Bruker 300 MHz spectrometer, with $^1$H chemical shifts referenced relative to residual protio solvent peaks. Due to the large number of aromatic substituents and the complexity of the spectra in the 6.5-8.5 ppm region, the peaks corresponding to the hydrogens on the aromatic rings are generally not assigned and are denoted as "ArH" in the lists of NMR data.

Ligand Source Synthesis

Reagents used for the synthesis of ligand sources A1-A20 are as follows.

BB1—2-hydroxy-3,5-di(t-butyl)benzaldehyde
BB2—2-hydroxy-3,5-chlorobenzaldehyde
BB3—2-hydroxy-3-phenyl-5-t-butylbenzaldehyde
BB4—2-hydroxy-3-(1-naphthyl)-5-methylbenzaldehyde
BB5—2-hydroxy-3-(1-naphthyl)-5-t-butylbenzaldehyde
BB6—2-hydroxy-3-(N-dibenzopyrrolyl)-5-t-butylbenzaldehyde
BB7—2-hydroxy-3-(N-dibenzopyrrolyl)-5-methylbenzaldehyde
BB8—2-hydroxy-3-(2,4,6-trimethylphenyl)-5-methylbenzaldehyde
BB9—2-hydroxy-3-(3,5-di(t-butyl)phenyl)-5-(t-butyl) benzaldehyde.

The aldehydes are converted to the corresponding benzyl alcohol (BA) by reaction with sodium borohydride. As an example, to a suspension of BB6 (500 mg, 1.46 mmol) in 6.0 mL MeOH, sodium borohydride (222 mg, 5.87 mmol) is added at 0° C. The reaction is warmed slowly to 25° C. and stirred for 3 h before being quenched with saturated aqueous NH$_4$Cl. MeOH is removed by rotary evaporation and the crude product mixture taken up in Et$_2$O. The Et$_2$O solution was washed with aqueous NH$_4$CL and then dried over Na$_2$SO$_4$. The product is purified by silica gel chromatography using hexanes/EtOAc=2:1 as eluent. The desired product, 2-hydroxy-3-(N-dibenzopyrrolyl)-5-t-butyl)benzyl alcohol, is isolated 415 mg, 83 percent yield, as a white solid.

Benzyl alcohols BA1-BA5 and BA7-BA9 were prepared according to the procedure described above for BB6. A total of 9 alcohols are prepared:

BA1—2-hydroxy-3,5-di(t-butyl)benzyl alcohol
BA2—2-hydroxy-3,5-chlorobenzyl alcohol
BA3—2-hydroxy-3-phenyl-5-t-butylbenzyl alcohol
BA4—2-hydroxy-3-(1-naphthyl)-5-methylbenzyl alcohol
BA5—2-hydroxy-3-(1-naphthyl)-5-t-butylbenzyl alcohol
BA6—2-hydroxy-3-(N-dibenzopyrrolyl)-5-t-butylbenzyl alcohol
BA7—2-hydroxy-3-(N-dibenzopyrrolyl)-5-methylbenzyl alcohol
BA8—2-hydroxy-3-(2,4,6-trimethylphenyl)-5-methylbenzyl alcohol
BA9—2-hydroxy-3-(3,5-di(t-butyl)phenyl)-5-(t-butyl) benzyl alcohol.

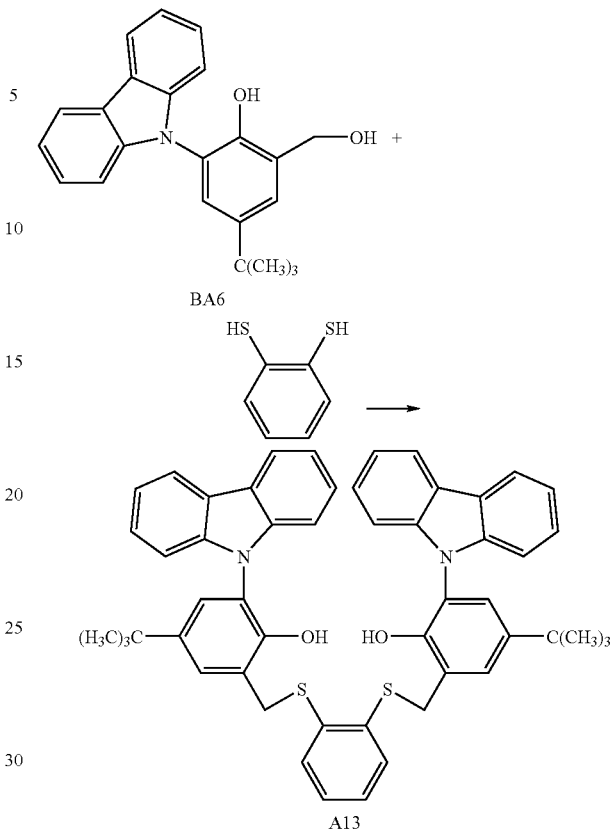

Synthesis of ligand Sources. The respective benzyl alcohols are contacted with dithiols (1,2-dimercaptobenzene, 1,2-ethylenedithiol, 1,3-propylenedithiol) or dialcohols (1,2-dihydroxybenzene, ethylene glycol, 1,3-propylene glycol) in a 2:1 molar ratio in the presence of ZnI$_2$ to form the polydentate ligand source. As an example, ZnI$_2$ (37 mg, 0.12 mmol) was added, under N$_2$, to a solution of BA6 (121 mg, 0.35 mmol) and 1,2-benzenedithiol (16 mg, 0.11 mmol) in toluene (3.0 mL). The reaction is stirred at room temperature overnight. The reaction is diluted with Et$_2$O then washed with saturated aqueous NaHCO$_3$ and dried over Na$_2$SO$_4$. Isolated yield is 55 mg, 61 percent, of A13 as a white solid after silica gel chromatography (Hexanes/EtOAc=20/1). $^1$H NMR (C$_6$D$_6$) δ 1.05 (s, 18H), 4.17 (s, 4H), 5.08 (s, 2H), 6.88 (m, 2H), 7.12-7.28 (m, 18H), 8.03 (m, 4H).

In the foregoing manner the following ligand sources A1-A50 may be prepared:

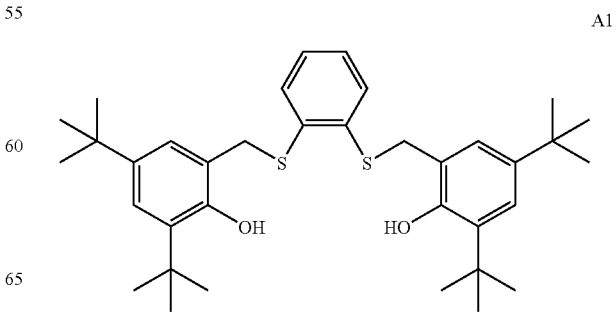

A2 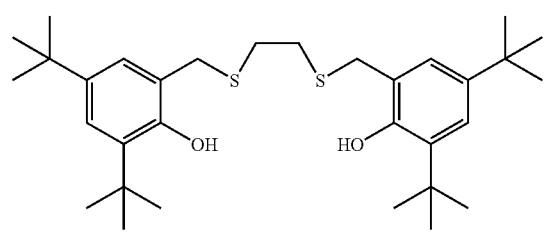
A3 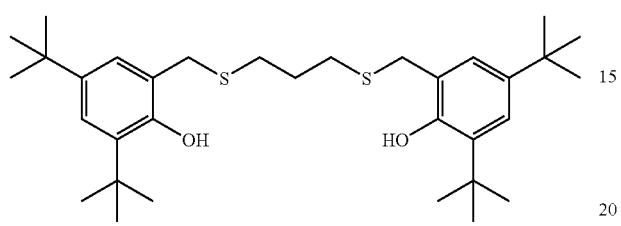
A4 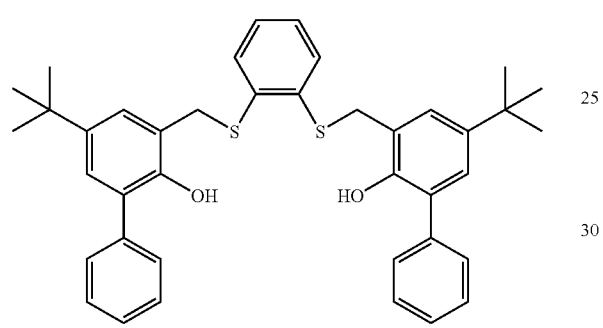
A5 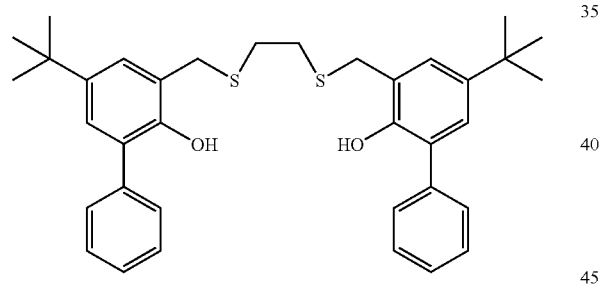
A6 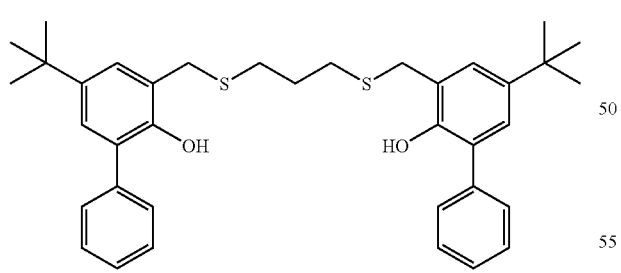
A7 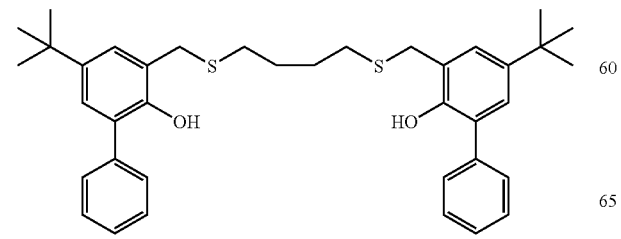
A8 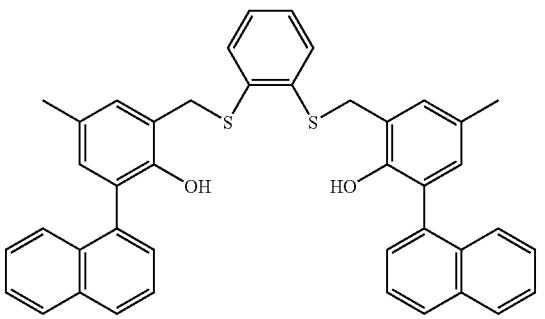
A9 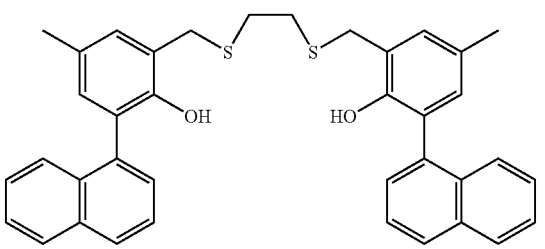
A10 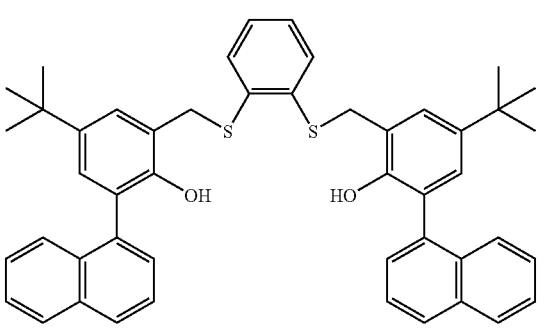
A11 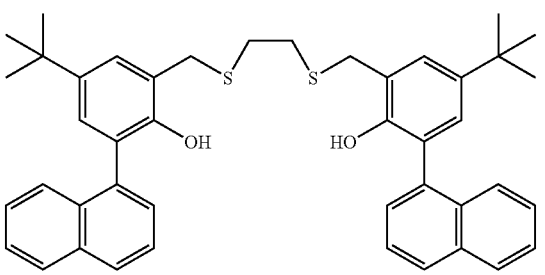
A12 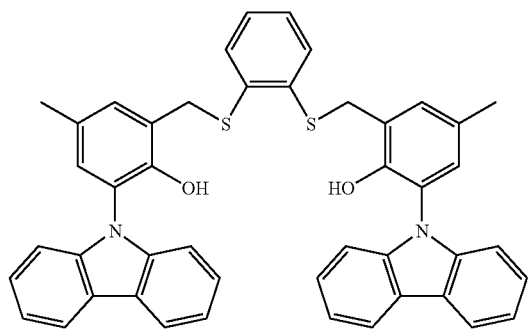

-continued
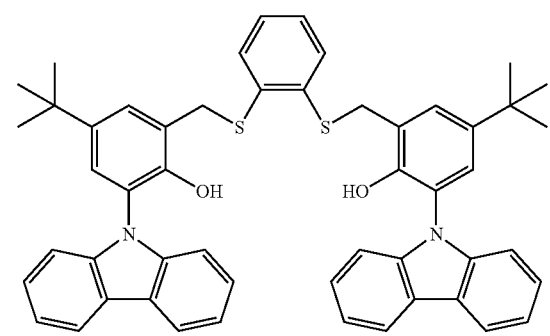
A13
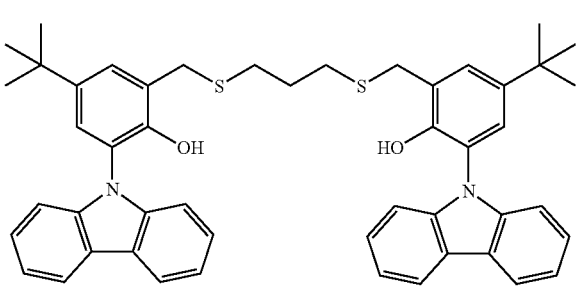
A14
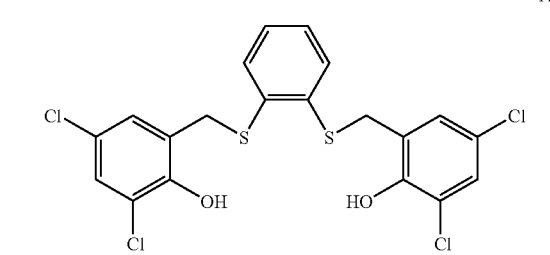
A15
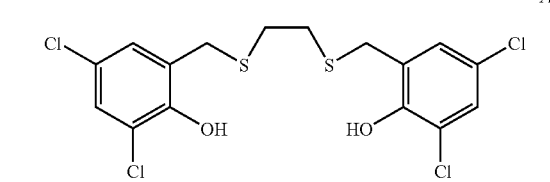
A16
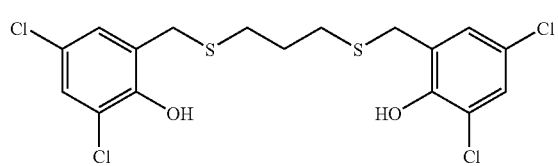
A17
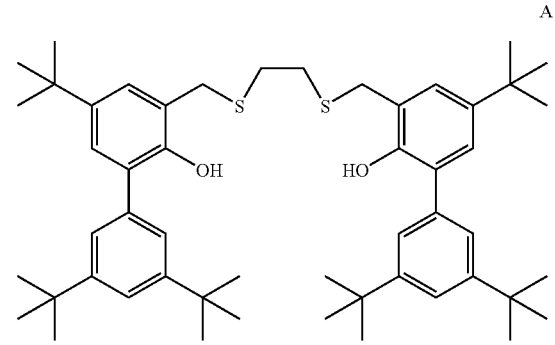
A18
-continued
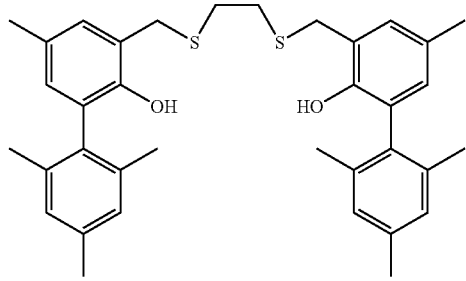
A19
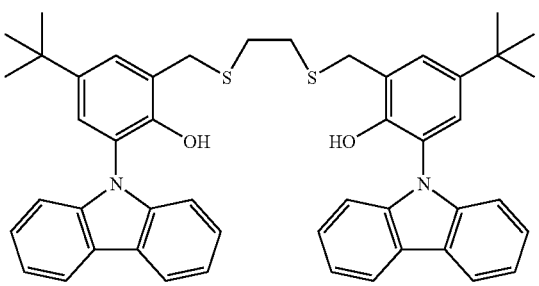
A20
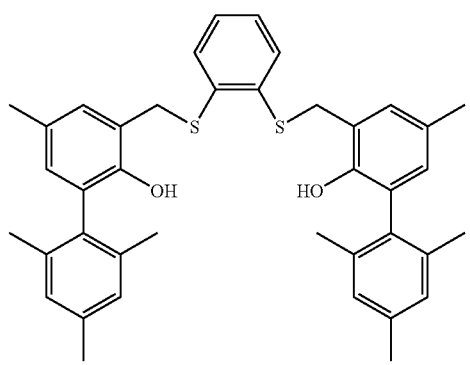
A21
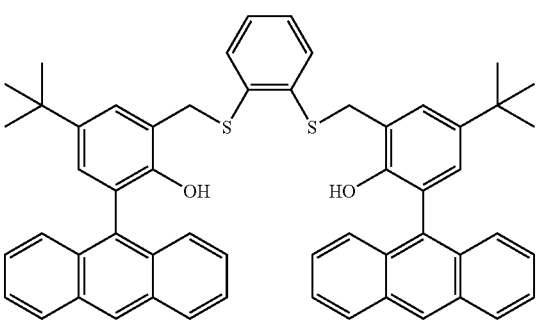
A22
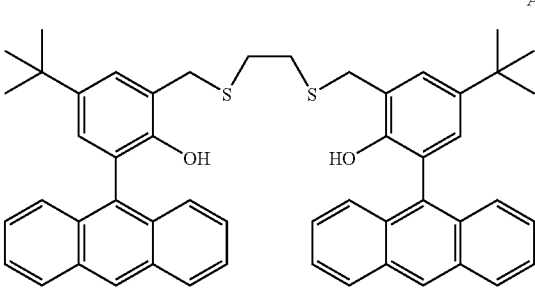
A23

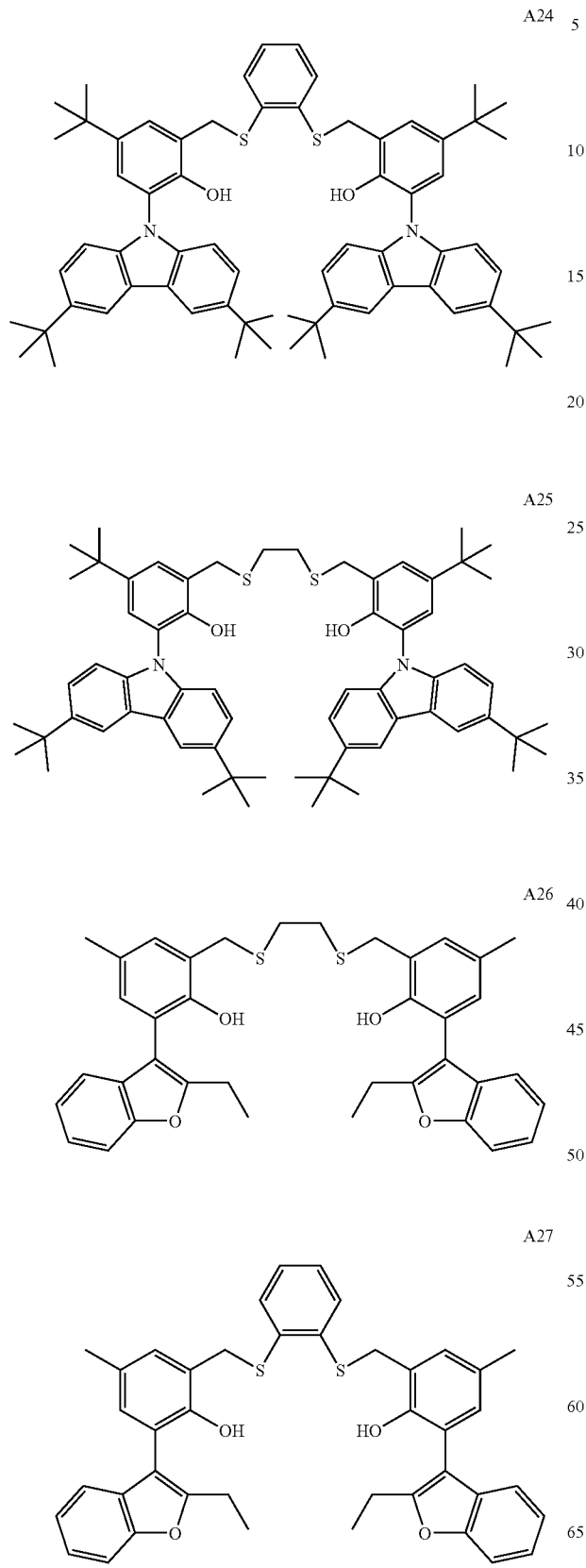
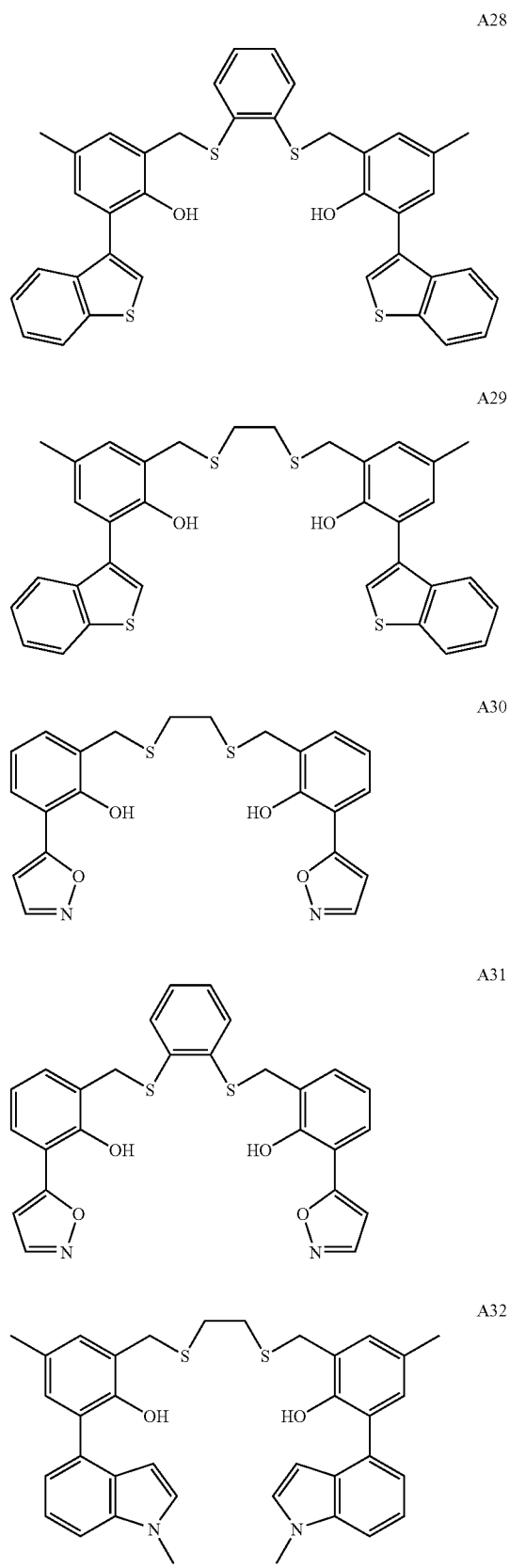

A33 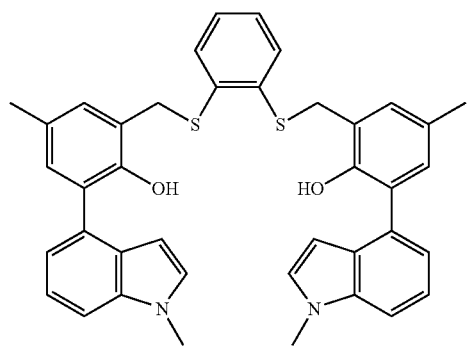
A34 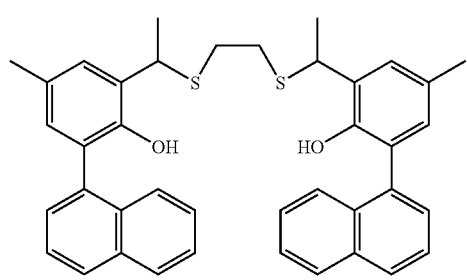
A35 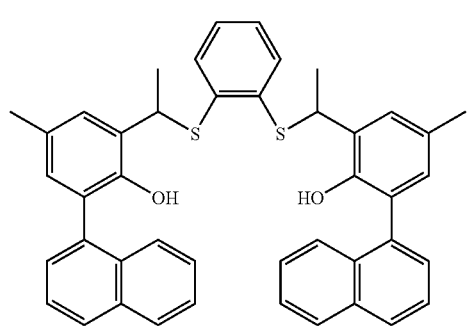
A36 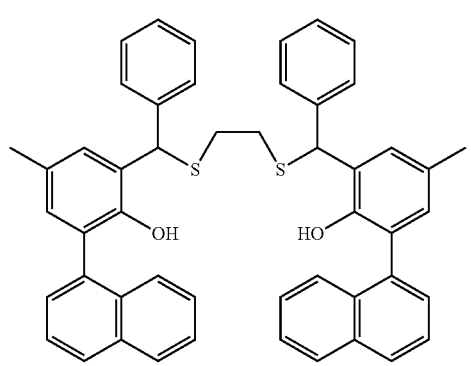
A37 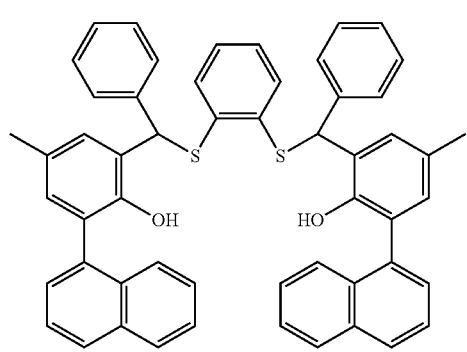
A38 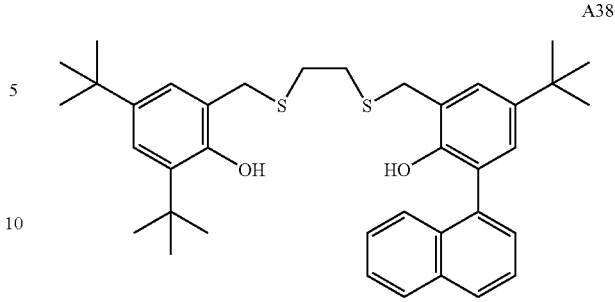
A39 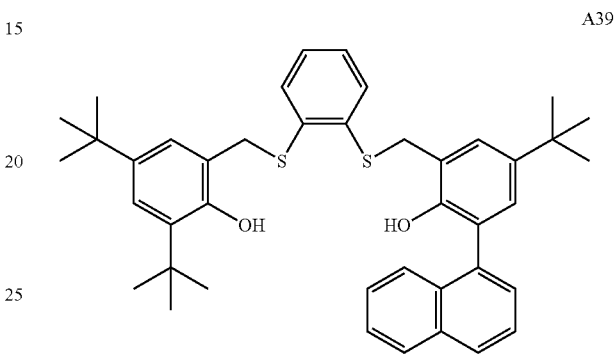
A40 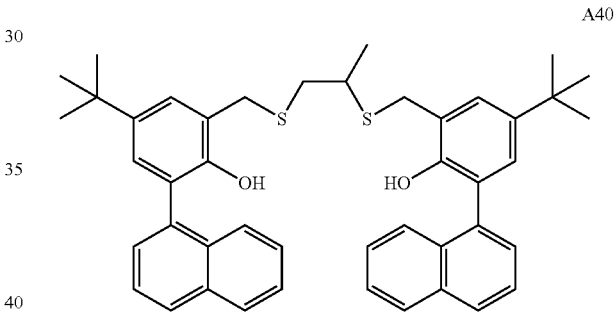
A41 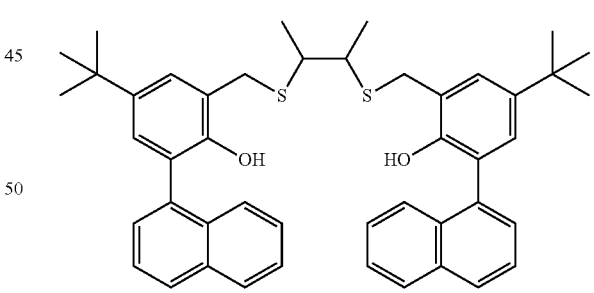
A42 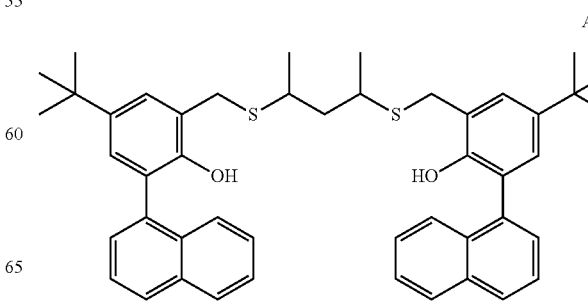

A43
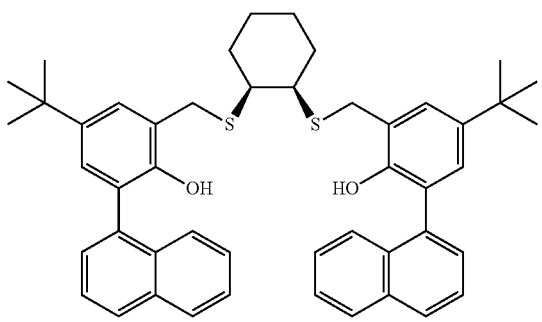
A44
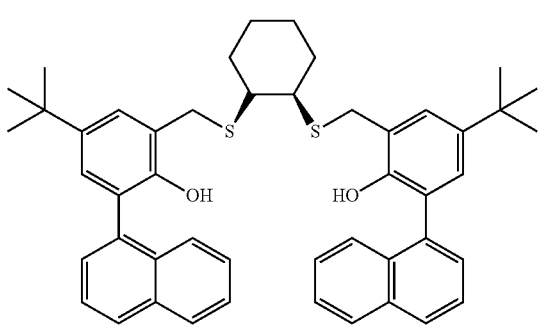
A45
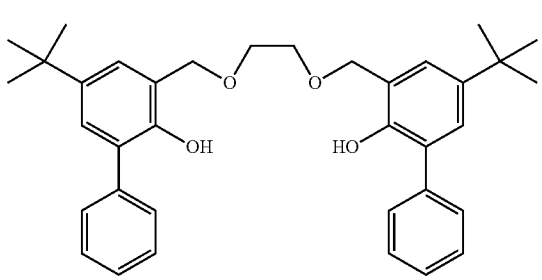
A46
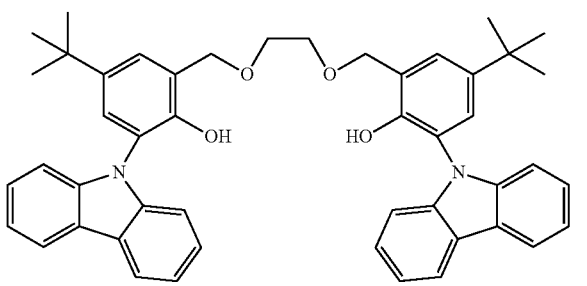
A47
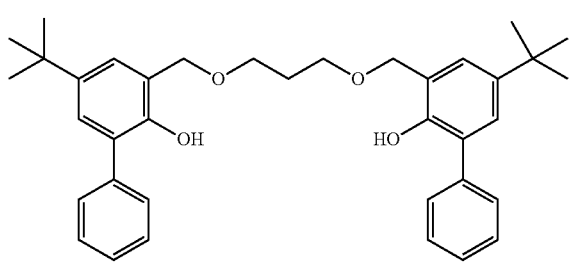
A48
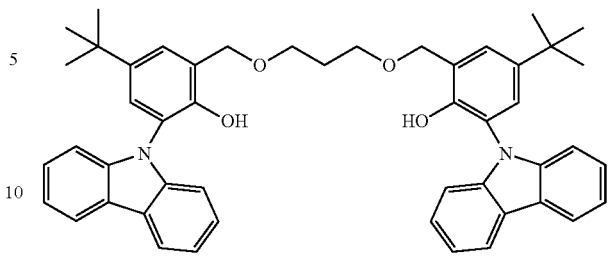
A49
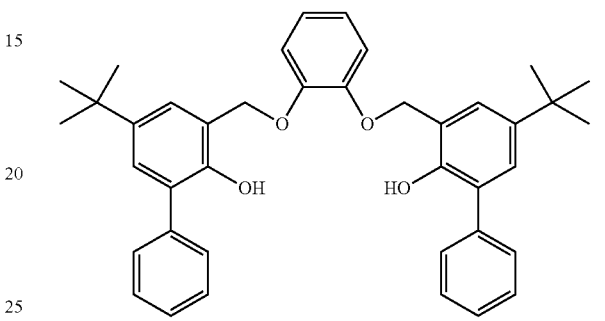
A50
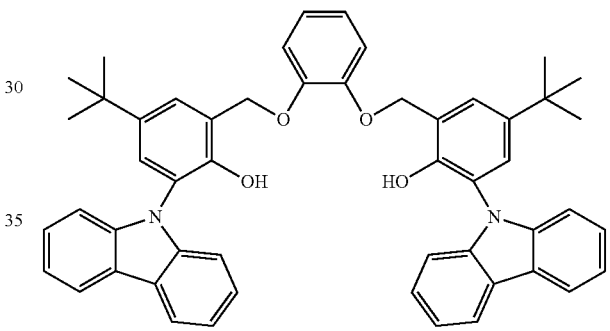
Synthesis of metal complexes. Metal complexes M1-M8 are prepared by standard metallation and organometal preparation techniques using the foregoing ligand sources and the corresponding metal-tetrabenzyl or dibenzyldichloride organometal complexes. The identities of the metal complexes prepared are:
M1
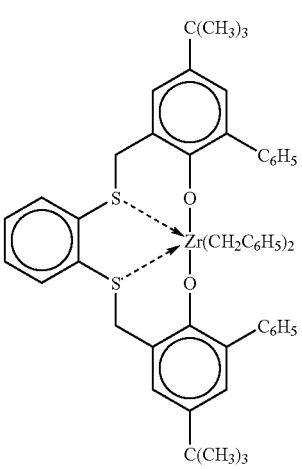

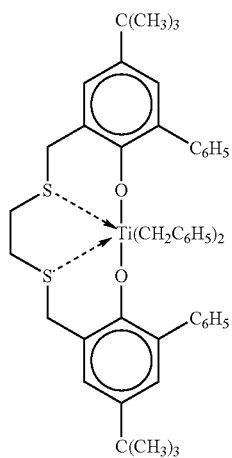
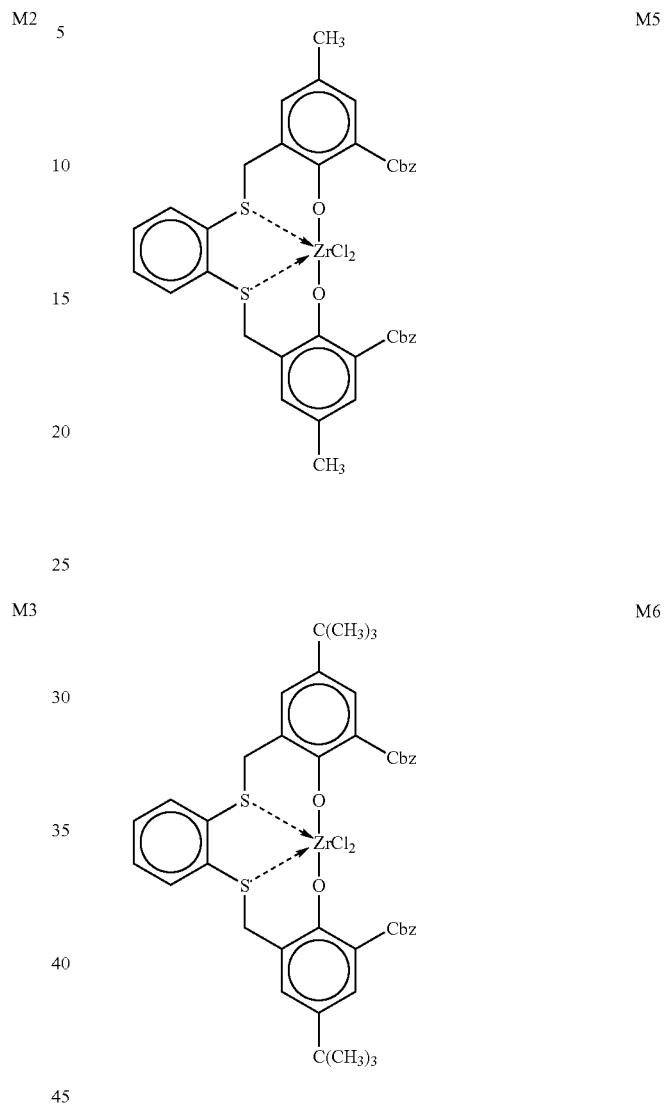
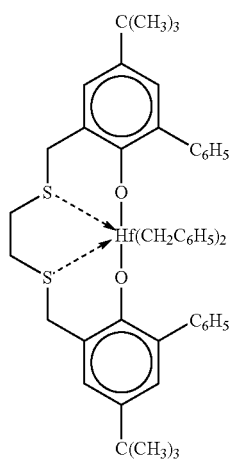
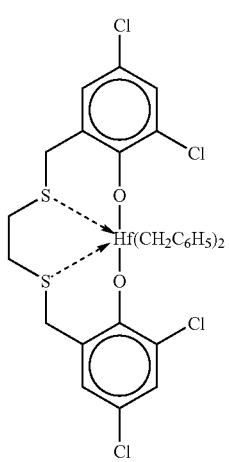

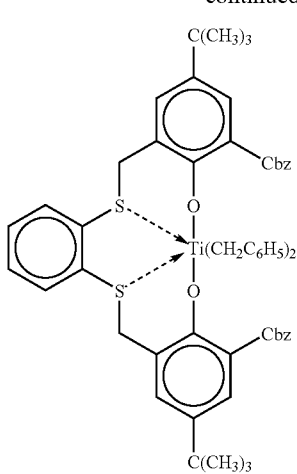

M8

Example 1

Synthesis of phenylene-1,2-bis(2-oxoyl-3-phenyl-5-(t-butyl)phenylmethylthio)zirconium (IV) dibenzyl (M1): 53.8 mg of a solution containing ligand A4 solution (in 0.8 mL of benzene-$d_6$) is added to a ZrBz$_4$ solution (39.6 mg in 0.2 mL benzene-$d_6$), and after 5 minutes the reaction solution is blown down to dryness under a stream of Ar. The resulting residue is collected, washed with 0.6 mL pentane and dried under vacuum. M1 is a pale yellow solid (73 mg, 78 percent yield). $^1$H NMR (C$_6$D$_6$, RT) δ 7.84 (d, 4H, ArH), 7.50 (t, 4H, ArH), 7.4-7.0 (m, overlap w/ solvent peak, ArH), 6.94 (d/d, 2H, ArH), 6.80 (d, 4H, ArH), 6.68 (d/d, 2H, ArH), 5.90 (d, 2H, ArH), 3.34 (d, 2H, SCH$_2$), 2.99 (d, 2H, SCH$_2$), 1.90 (d, 2H, ZrCH$_2$), 1.08 (s, 18H, $^t$Bu), 0.95 (d, 2H, ZrCH$_2$) partially overlapped with $^t$Bu group signal.

Example 2

Synthesis of ethylene-1,2-bis(2-oxoyl-3-phenyl-5-(t-butyl)phenylmethylthio)titanium (IV) dibenzyl (M2): TiBz$_4$ (18.7 mg) and A5 (25.9 mg) are added as solids into a vial followed by 2.0 mL of toluene. The reaction mixture is shaken by hand until all solids are in solution. After 15 minutes, the dark red-brown reaction solution is blown down to dryness under a stream of Ar. The resulting residue (M2) is a deep red-purple solid. $^1$H NMR (C$_6$D$_6$, RT) δ 8.10 (d, 4H, ArH), 7.44 (m, 4H, ArH), 7.2-6.7 (m, overlap w/ solvent peak, ArH), 6.51 (d, 2H, ArH), 2.54 (s, 4H, CH$_2$), 1.23 (s, 8H, CH$_2$) partially overlapped with $^t$Bu group signal at 1.19 (s, 18H, $^t$Bu).

Example 3

Synthesis of ethylene-1,2-bis(2-oxoyl-3-phenyl-5-(t-butyl)phenylmethylthio)zirconium (IV) dibenzyl (M3): 68.7 mg of ZrBz$_4$ (in 3 mL of toluene) is added to an A5 solution (86.0 mg in 3 mL toluene) and the resultant yellow solution is briefly shaken. After 5 minutes, the reaction solution is blown down to near dryness under a stream of Ar. 3 ml of pentane are added, and the layer solution is placed in a −35° C. freezer overnight. The resulting precipitate is collected, washed with pentane and dried under vacuum. M3 is recovered as a yellow solid (106 mg, 83 percent yield). $^1$H NMR (C$_6$D$_6$, RT) δ 7.69 (d, 4H, ArH), 7.3-6.8 (m, overlap w/ solvent peak, ArH), 6.67 (d, 4H, ArH), 6.51 (d, 2H, ArH), 2.93 (d, 2H, SCH$_2$), 2.75 (d, 2H, SCH$_2$), 1.98 (d, 2H, CH$_2$), 1.72 (d, 2H, ZrCH$_2$), 1.19 (s, 18H, $^t$Bu), 1.13 (d, 2H, CH$_2$) partially overlapped with $^t$Bu group signal, 0.81 (d, 2H, ZrCH$_2$).

Example 4

Synthesis of ethylene-1,2-bis(2-oxoyl-3-phenyl-5-(t-butyl)phenylmethylthio)hafnium (IV) dibenzyl (M4): HfBz$_4$ (24.3 mg) and A5 (25.5 mg) are added as solids into a vial followed by 2.0 mL of toluene. The reaction mixture is shaken by hand until all solids are in solution. After 2 hours, the pale yellow reaction solution is blown down to dryness under a stream of Ar. The resulting residue (M4) is recovered as an off-white solid. $^1$H NMR (C$_6$D$_6$, RT) δ 7.87 (d, 4H, ArH), 7.42 (m, 4H, ArH), 7.3-6.8 (m, overlap w/ solvent peak, ArH), 6.71 (d, 4H, ArH), 6.48 (d, 2H, ArH), 2.73 (did, 4H, SCH$_2$), 2.02 (d, 2H, CH$_2$), 1.80 (d, 2H, HfCH$_2$), 1.46 (d, 2H, CH$_2$), 1.18 (s, 18H, $^t$Bu), 1.05 (d, 2H, HfCH$_2$) partially overlapped with $^t$Bu group signal.

Example 5

Synthesis of phenylene-1,2-bis(2-oxoyl-3-(N-dibenzopyrrolyl)-5-(methyl)phenylmethylthio)zirconium (IV) dichloride (M5): ZrBz$_2$Cl$_2$.OEt$_2$ (21.6 mg) and A12 (36.9 mg) are each dissolved in 1 mL of benzene-$d_6$. The ZrBz$_2$Cl$_2$.OEt$_2$ solution is added dropwise to the A12 solution, and after briefly mixing, the reaction solution is dried under a stream of Ar, followed by vacuum. The resultant solid is washed multiple times with pentane, followed by vacuum. 42 mg of an off-white solid (M5) are obtained (90 percent yield). $^1$H NMR (C$_6$D$_6$, RT) δ 8.15 (did, 4H, ArH), 7.6-6.5 (m, overlap w/ solvent peak, ArH), 5.72 (s, 2H, ArH), 3.69 (d, 2H, SCH$_2$), 2.83 (d, 2H, SCH$_2$), 1.62 (s, 6H, ArCH$_3$).

Example 6

Synthesis of phenylene-1,2-bis(2-oxoyl-3-(N-dibenzopyrrolyl)-5-(t-butyl)phenylmethylthio)zirconium (IV) dichloride (M6): ZrBz$_2$Cl$_2$.OEt$_2$ (31.5 mg) and A13 (59.9 mg) are added as solids into a vial followed by 1.5 mL of toluene. The solution is stirred for 30 minutes at RT. The volatiles were removed under a stream of Ar. The product is an off-white solid (76 mg, 83 percent yield). $^1$H NMR (CD$_2$Cl$_2$, RT) δ 8.15 (d/d, 4H, ArH), 7.5-7.1 (m, 18H, ArH), 6.40 (d, 2H, ArH), 4.10 (d, 2H, SCH$_2$), 3.71 (d, 2H, SCH$_2$), 1.01 (s, 18H, $^t$Bu).

Example 7

Synthesis of ethylene-1,2-bis(2-oxoyl-3,5-dichlorophenylmethylthio)hafnium (IV) dibenzyl (M7): HfBz$_4$ (29.4 mg) and A16 (37.7 mg) are added as solids into a vial followed by 2.0 mL of toluene. The reaction mixture is shaken by hand until all solids are in solution. After 3.5 hours, the reaction solution is blown down to dryness under a stream of Ar. The resulting residue (M7) is recovered as a pale yellow solid. $^1$H NMR (C$_6$D$_6$, RT) δ 7.6-6.9 (m, overlap w/ solvent peak, ArH), 6.13 (d, 2H, ArH), 2.45 (m, 6H, CH$_2$), 1.78 (d, 2H, CH$_2$), 1.64 (d, 2H, CH$_2$), 0.89 (d, 2H, CH$_2$).

Example 8

Synthesis of phenylene-1,2-bis(2-oxoyl-3-(N-dibenzopyrrolyl)-5-(t-butyl)phenylmethylthio)titanium (IV) dibenzyl (M8): 20.2 mg of A13 solution (in 1 mL of toluene) is added dropwise to a TiBz$_4$ solution (13.7 mg in 1 mL toluene). The reaction solution is blown down to dryness under a stream of Ar. The resulting residue (M8) is collected, washed with pentane and dried under Ar (21 mg, 62 percent yield). $^1$H NMR (toluene-d$_8$, RT) δ 8.13 (d, 4H, ArH), 7.48 (t, 4H, ArH), 7.36 (s, 2H, ArH), 7.28 (d/d, 2H, ArH), 7.2-6.9 (m, overlap w/ solvent peak, ArH), 6.76 (d/d, 2H, ArH), 6.71 (m, 6H, ArH), 6.58 (d/d, 2H, ArH), 5.81 (d, 2H, ArH), 2.71 (bs, 8H, CH$_2$), 0.95 (s, 18H, $^t$Bu).

Examples 9-16

The preparation techniques used in Examples 1-8 are repeated using ligand sources A45, A46, A49, and A50 to prepare metal complexes: phenylene-1,2-bis(2-oxoyl-3-phenyl-5-(t-butyl)phenyl methoxy)zirconium (IV) dibenzyl (M9), ethylene-1,2-bis(2-oxoyl-3-phenyl-5-(t-butyl)phenylmethoxy)titanium (IV) dibenzyl (M10), ethylene-1,2-bis(2-oxoyl-3-phenyl-5-t-butyl)phenylmethoxy)zirconium (IV) dibenzyl (M11), ethylene-1,2-bis(2-oxoyl-3-phenyl-5-(t-butyl)phenylmethoxy)hafnium (IV) dibenzyl (M12), phenylene, 1,2-bis(2-oxoyl-3-(N-dibenzopyrrolyl)-5-(methyl)phenylmethoxy)zirconium (IV) dichloride (M13), phenylene-1,2-bis(2-oxoyl-3-(N-dibenzopyrrolyl)-5-(t-butyl)phenylmethoxy)zirconium (IV) dichloride (M14), ethylene-1,2-bis(2-oxoyl-3,5-dichlorophenylmethoxy)hafnium (IV) dibenzyl (M15), and phenylene-1,2-bis(2-oxoyl-3-(N-dibenzopyrrolyl)-5-(t-butyl)phenylmethoxy)titanium (IV) dibenzyl (M16).

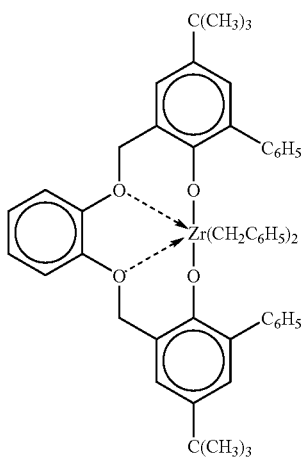

M9

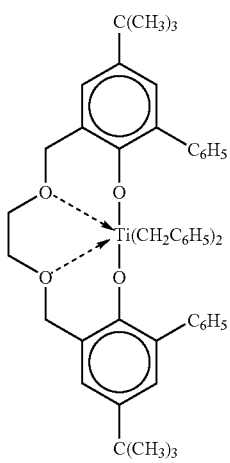

M10

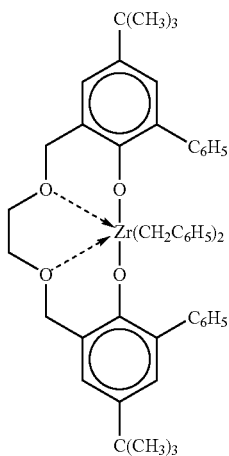

M11

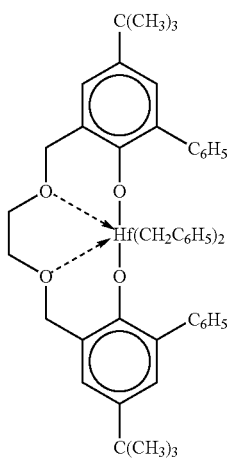

M12

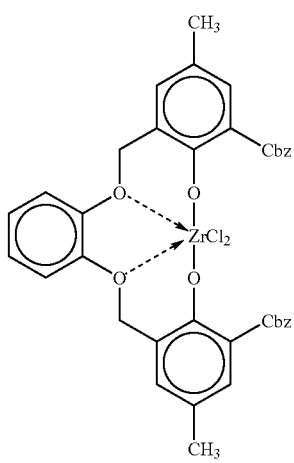

M13

M14

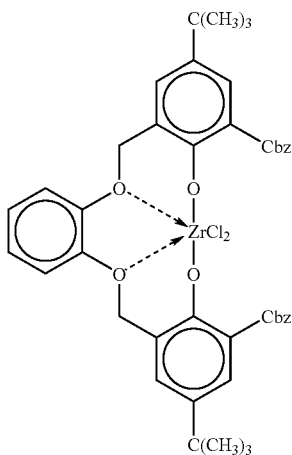

M15

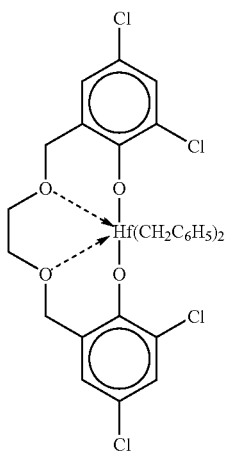

M16

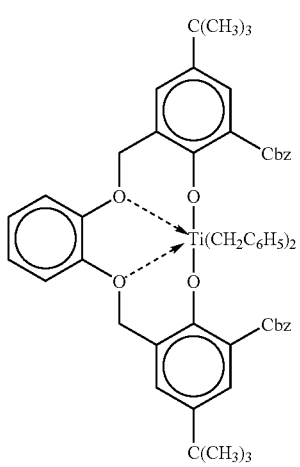

Example 17

Synthesis of ethylene-1,2-bis((2-oxoyl-3-(N-dibenzopyrrolyl)-5-(t-butyl)phenylmethylthio)zirconium (IV) dibenzyl (M17)

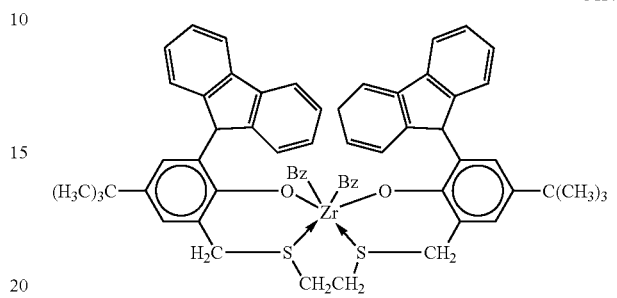

In a vial, 208.7 mg (0.28 mmol) of A20, 127 mg (0.28 mmol) of Zr(CH$_2$Ph)$_4$ and 8 mL of toluene are added and mixed. After stirring for 5 hours at room temperature, solvent is removed under reduced pressure. The material is redissolved in 2 mL toluene followed by addition of 8 mL of hexane which causes precipitation of a yellow solid. The solid is filtered on the frit, washed twice with 4 mL of hexane and dried under reduced pressure to give 200 mg of product. Yield 70.4 percent.

$^1$H NMR (toluene-d8, RT) δ 8.06 (dm, $J_{H-H}$=7.8 Hz, 2H), 8.00 (dm, $J_{H-H}$=9.0 Hz, 2H), 7.54 (m, 4H), 7.32 (m, 4H), 7.23 (m, 4H), 6.99 (dm, $J_{H-H}$=7.2 Hz, 2H), 6.68 (m, 6H), 6.61 (d, $J_{H-H}$=2.4 Hz, 2H), 5.42 (dm, $J_{H-H}$=8.4 Hz, 4H), 2.67 (d, $J_{H-H}$=14.0 Hz, 2H), 2.53 (d, $J_{H-H}$=14.0 Hz, 2H), 2.14 (d, $J_{H-H}$=9.0 Hz, 2H), 1.35 (d, $J_{H-H}$=9.0 Hz, 2H), 1.14 (s, 18H), 0.81 (d, $J_{H-H}$=8.1 Hz, 2H), −0.19 (d, $J_{H-H}$=9.0 Hz, 2H).

Styrene Homopolymerization in 96-Well Combinatorial Array

Metal complexes are prepared in situ and used to polymerize styrene monomer under combinatorial reaction conditions. Solutions of metal precursors are prepared in toluene typically at 1-20 mM concentrations. The solutions of Ti(CH$_2$C$_6$H$_5$)$_4$; Zr(CH$_2$C$_6$H$_5$)$_4$; Hf(CH$_2$C$_6$H$_5$)$_4$; Ti(N(CH$_3$)$_2$)$_4$; Zr(N(CH$_3$)$_2$)$_4$; Hf(N(CH$_3$)$_2$)$_4$; and TiCl$_2$(N(CH$_3$)$_2$)$_2$ (0.3 mmol) may also be combined with 0.3 μmol of B(C$_6$F$_5$)$_3$ to form various cationic metal complexes according to the invention, including: [Ti(CH$_2$C$_6$H$_5$)$_3$$^+$][C$_6$H$_5$CH$_2$B(C$_6$F$_5$)$_3$$^-$]; [Zr(CH$_2$C$_6$H$_5$)$_3$$^+$][C$_6$H$_5$CH$_2$B(C$_6$F$_5$)$_3$$^-$] and [Hf(CH$_2$C$_6$H$_5$)$_3$$^+$][C$_6$H$_5$CH$_2$B(C$_6$F$_5$)$_3$$^-$]. Solutions of Group 13 reagents (scavengers) are prepared in toluene typically at 50-250 mmol/l. The scavengers used include: Al(Me)$_3$, (TMA); Al(Et)$_3$, (TEA); Al($^i$Bu)$_3$, (TIBA); modified methylaluminoxane (MMAO); and nonhydrolytic polymethylaluminoxane (PMAO—IP). MMAO and PMAO—IP are obtained commercially from Azko Chemical. Inc., Chicago, Ill. Solutions of activators are prepared in toluene typically at 4-10 mM, except MAO (0.5-1M). The activators employed are: B(C$_6$F$_5$)$_3$; [C(C$_6$H$_5$)$_3$]$^+$[B(C$_6$F$_5$)$_4$]$^-$, (TBF20); [HN(CH$_3$)$_2$Ph]$^+$[B(C$_6$F$_5$)$_4$]$^-$, (ABF20); [HN(C$_6$H$_{13}$)$_2$(-para-C$_4$H$_9$-Ph)]$^+$[B(C$_6$F$_5$)$_4$]$^-$. (SJBF20); [HN(C$_{10}$H$_{21}$)$_2$(-para-C$_4$H$_9$-Ph)]$^+$[B(C$_6$F$_5$)$_4$]$^-$, (SJ2BF20); PMAO and MMAO. Combinations of the foregoing reagents are prepared in situ thereby forming various catalyst compositions within a 96 well array.

Styrene homopolymerization reactions are performed in a 96-well format using 8×30 mm tarred glass vials arranged in an 8×12 array within an aluminum block. Reagents are added from the stock solutions to the vials using a Cavro liquid handling robot driven by Symyx software (described for example in EP 1080435, U.S. Pat. No. 6,507,645, and EP 1175645). The vials contain polytetrafluoroethylene coated stir-bars and are weighed prior to their use. Solutions of a parent ligand array of desired ligand sources are transferred to arrays of glass vials to provide 0.3-0.6 μmol of each ligand source and the solvent is then removed from the ligand array using a nitrogen or argon stream. The resultant ligand array is contacted with toluene, a suitable metal precursor, a group 13 reagent or an activator (or combination of group 13 reagents and an activator), and 100-300 μL of styrene monomer. A polytetrafluoroethylene membrane and rubber gasket are then placed over the top of the array followed by an aluminum cover screwed in place to seal the array. The array is placed within a parallel batch reactor which heats and stirs the contents of the array for the desired reaction time. The foregoing array and polymerization process are further disclosed in U.S. Pat. No. 6,507,645, WO 04/060550 and US-A-2004/0121448. Polymerization is conducted under a variety of temperature, pressure and other process conditions.

Method 1: 75° C. Complexation, 75° C. Screening; 300 μL total well volume: The ligand array (0.3-0.6 μmol of each ligand) is first contacted with toluene (100 μL per well) and then toluene solutions of the desired metal precursor compound (15-30 μL per well, 0.3 μmol). The resultant mixtures are stirred for a period of 45-120 minutes at 75° C. The array (while still on a heater/stirrer) is then treated with a stock solution of the appropriate group 13 reagent (30 μL per well, contact time of 10 min, 75° C.), followed by an activator (or activator mixture), 30-75 μL per well, contact time of 5 min, 75° C.). 100 μl of styrene is added to each well; the array is sealed; and polymerization is conducted with stirring at 75° C. for 1 hour.

Method 2: 75° C. Complexation, 105° C. Screening; 500 μL total well volume: The ligand array (0.3-0.6 μmol of each ligand) is first contacted with toluene (100 μL per well) and then toluene solutions of the desired metal precursor compound (15-30 μL per well, 0.3 μmol). The resultant mixtures are stirred for a period of 45-20 minutes at 75° C. The array (while still on a heater/stirrer) is then treated with a stock solution of the appropriate group 13 reagent (30 μL per well, contact time of 10 min, 75° C.). The array is moved to a heater/stirrer set at 105° C. and an activator (or activator mixture) 30-75 μL per well is added, followed by a contact time of min, 105° C.). Styrene monomer (300 μL, pre-heated to 105° C.) is added to each well; the array is sealed and polymerization is conducted with stirring at 105° C. for 1 hour.

After polymerization each vial in the array is filled with toluene in order to generate a total volume of 800 μL. The resulting toluene solutions are mechanically agitated and sampled (40-0 μL) for automated GPC analysis. Conversions are determined by weight of polymer produced and are approximate (often greater than 100%) due to entrained solvent. Selected results are contained in Table 1

TABLE 1

| run | T (° C.) | μmol styrene | scavenger (mole eq.)* | activator (mole eq.)* | ligand source | metal precursor | conv. % | Mw × $10^{-3}$ |
|---|---|---|---|---|---|---|---|---|
| ps1 | 105 | 8700 | TMA (5) | ABF20 (1) | A1 | $ZrBz_4$ | 33 | 13 |
| ps2 | 75 | 2900 | MMAO (5) | ABF20 (1) | A2 | $ZrBz_4$ | 3 | 164 |
| ps3 | 75 | 2900 | TIBA (5) | SJ2BF20 (1) | A2 | $ZrBz_4$ | 3 | 78 |
| ps4 | 75 | 2900 | PMAO (5) | PMAO (200) | A4 | $HfBz_4$ | 13 | 10 |
| ps5 | 75 | 2900 | TEA (5) | MMAO (200) | A4 | $HfBz_4$ | 20 | 7 |
| ps6 | 75 | 2900 | MMAO (50) | MMAO (200) | A4 | $Zr(NMe_2)_4$ | 9 | 107 |
| ps7 | 75 | 2900 | TIBA (25) | TBF20 (1) | A4 | $Zr(NMe_2)_4$ | 18 | 136 |
| ps8 | 75 | 2900 | TIBA (5) | SJ2BF20 (1) | A4 | $ZrBz_3^+$ | 11 | 283 |
| ps9 | 75 | 2900 | TMA (5) | ABF20 (1) | A4 | $ZrBz_3^+$ | 50 | 123 |
| ps10 | 75 | 2900 | MMAO (5) | MMAO (200) | A4 | $ZrBz_4$ | 60 | 78 |
| ps11 | 75 | 2900 | PMAO (5) | SJBF20 (1) | A4 | $ZrBz_4$ | 88 | 175 |
| ps12 | 75 | 2900 | TEA (5) | ABF20 (1) | A4 | $ZrBz_4$ | 21 | 71 |
| ps13 | 75 | 2900 | TEA (5) | SJBF20 (1) | A4 | $ZrBz_4$ | 22 | 59 |
| ps14 | 75 | 2900 | TIBA (5) | ABF20 (1) | A4 | $ZrBz_4$ | 47 | 237 |
| ps15 | 75 | 2900 | TMA (5) | ABF20 (1) | A4 | $ZrBz_4$ | 80 | 119 |
| ps16 | 105 | 8700 | PMAO (5) | SJBF20 (1) | A4 | $ZrBz_4$ | 88 | 165 |
| ps17 | 105 | 8700 | TIBA (5) | ABF20 (1) | A4 | $ZrBz_4$ | 27 | 150 |
| ps18 | 105 | 8700 | TMA (5) | ABF20 (1) | A4 | $ZrBz_4$ | 31 | 96 |
| ps19 | 75 | 2900 | MMAO (5) | MMAO (200) | A5 | $HfBz_4$ | 44 | 10 |
| ps20 | 75 | 2900 | TIB (5) | SJ2BF20 (1) | A5 | $HfBz_4$ | 26 | 32 |
| ps21 | 105 | 8700 | MMAO (5) | MMAO (200) | A5 | $HfBz_4$ | 13 | 6 |
| ps22 | 105 | 8700 | TIBA (5) | SJ2BF20 (1) | A5 | $HfBz_4$ | 15 | 22 |
| ps23 | 75 | 2900 | MMAO (5) | MMAO (200) | A5 | $ZrBz_4$ | 78 | 64 |
| ps24 | 75 | 2900 | PMAO (5) | SJ2BF20 (1) | A5 | $ZrBz_4$ | 119 | 299 |
| ps25 | 75 | 2900 | TIBA (5) | ABF20 (1) | A5 | $ZrBz_4$ | 98 | 302 |
| ps26 | 105 | 8700 | MMAO (5) | MMAO (200) | A5 | $ZrBz_4$ | 18 | 48 |
| ps27 | 105 | 8700 | PMAO (5) | PMAO (200) | A5 | $ZrBz_4$ | 43 | 68 |
| ps28 | 105 | 8700 | PMAO (5) | SJ2BF20 (1) | A5 | $ZrBz_4$ | 100 | 148 |
| ps29 | 105 | 8700 | TIBA (5) | ABF20 (1) | A5 | $ZrBz_4$ | 104 | 170 |
| ps30 | 105 | 8700 | TMA (5) | ABF20 (1) | A6 | $ZrBz_4$ | 22 | 18 |
| ps31 | 75 | 2900 | PMAO (5) | PMAO (200) | A8 | $HfBz_4$ | 18 | 12 |
| ps32 | 75 | 2900 | MMAO (5) | MMAO (200) | A8 | $ZrBz_4$ | 70 | 142 |
| ps33 | 75 | 2900 | PMAO (5) | SJ2BF20 (1) | A8 | $ZrBz_4$ | 84 | 249 |
| ps34 | 75 | 2900 | TMA (5) | ABF20 (1) | A8 | $ZrBz_4$ | 64 | 147 |
| ps35 | 105 | 8700 | MMAO (5) | MMAO (200) | A8 | $ZrBz_4$ | 26 | 109 |
| ps36 | 105 | 8700 | PMAO (5) | SJ2BF20 (1) | A8 | $ZrBz_4$ | 107 | 172 |
| ps37 | 105 | 8700 | TMA (5) | ABF20 (1) | A8 | $ZrBz_4$ | 32 | 180 |
| ps38 | 75 | 2900 | PMAO (5) | PMAO (200) | A12 | HfBzv | 56 | 53 |
| ps39 | 75 | 2900 | TEA (5) | ABF20 (1) | A12 | $HfBz_4$ | 17 | 103 |

TABLE 1-continued

| run | T (° C.) | µmol styrene | scavenger (mole eq.)* | activator (mole eq.)* | ligand source | metal precursor | conv. % | Mw × $10^{-3}$ |
|---|---|---|---|---|---|---|---|---|
| ps40 | 75 | 2900 | TIBA (5) | SJ2BF20 (1) | A12 | HfBzv | 34 | 127 |
| ps41 | 105 | 8700 | PMAO (5) | PMAO (200) | A12 | $HfBz_4$ | 51 | 38 |
| ps42 | 105 | 8700 | TEA (5) | ABF20 (1) | A12 | $HfBz_4$ | 10 | 60 |
| ps43 | 105 | 8700 | TIBA (5) | SJ2BF20 (1) | A12 | $HfBz_4$ | 35 | 73 |
| ps44 | 75 | 2900 | MMAO (5) | MMAO (200) | A12 | $ZrBz_4$ | 94 | 360 |
| ps45 | 75 | 2900 | PMAO (5) | SJ2BF20 (1) | A12 | $ZrBz_4$ | 106 | 378 |
| ps46 | 75 | 2900 | TIBA (5) | ABF20 (1) | A12 | $ZrBz_4$ | 133 | 413 |
| ps47 | 75 | 2900 | TMA (5) | ABF20 (1) | A12 | $ZrBz_4$ | 131 | 353 |
| ps48 | 105 | 8700 | MMAO (5) | MMAO (200) | A12 | $ZrBz_4$ | 71 | 197 |
| ps49 | 105 | 8700 | PMAO (5) | SJ2BF20 (1) | A12 | $ZrBz_4$ | 127 | 203 |
| ps50 | 105 | 8700 | TIBA (5) | ABF20 (1) | A12 | $ZrBz_4$ | 129 | 246 |
| ps51 | 105 | 8700 | TMA (5) | ABF20 (1) | A12 | $ZrBz_4$ | 91 | 210 |
| ps52 | 75 | 2900 | PMAO (50) | SJBF20 (1) | A15 | $Ti(NMe_2)_4$ | 5 | 71 |
| ps53 | 75 | 2900 | TIBA (5) | SJBF20 (1) | A15 | $TiBz_4$ | 2 | 86 |

*molar equivalents based on metal complex (catalyst)

Bulk Styrene Homopolymerization in 8-Well Combinatorial Array

Toluene solutions (10-20 mM) of $Ti(CH_2C_6H_5)_4$; $Zr(CH_2C_6H_5)_4$; $Hf(CH_2C_6H_5)_4$; $Ti(N(CH_3)_2)_4$; $Zr(N(CH_3)_2)_4$; $Hf(N(CH_3)_2)_4$; $TiCl_2(N(CH_3)_2)_2$; are prepared. In addition, solutions of $[Ti(CH_2C_6H_5)_3^+]$; $[C_6H_5CH_2B(C_6F_5)_3^-]$; $[Zr(CH_2C_6H_5)_3^+][C_6H_5CH_2B(C_6F_5)_3^-]$ and $[Hf(CH_2C_6H_5)_3^+][C_6H_5CH_2B(C_6F_5)_3^-]$ are generated in situ within 8 well combinatorial arrays by reaction of equal molar quantities of the tetrabenzyl metal derivative with $B(C_6F_5)_3$. Toluene solutions (50-250 mM) of the following Group 13 reagents are also prepared: $Al(Me)_3$, (TMA); $Al(Et)_3$, (TEA); $Al(^iBu)_3$, (TIBA); PMAO and MMAO. Toluene solutions (4-10 mM) of the following activators are also prepared: $B(C_6F_5)_3$; $[C(C_6H_5)_3]^+[B(C_6F_5)_4]^-$, (TBF20); $[HN(CH_3)_2Ph]^+[B(C_6F_5)_4]^-$, (ABF20); $[HN(C_6H_{13})_2(para-C_4H_9-Ph)]^+[B(C_6F_5)_4]^-$, (SJBF20); $[HN(C_{10}H_{21})_2(para-C_4H_9-Ph)]^+[B(C_6F_5)_4]^-$, (SJ2BF20). Toluene solution (0.5-1 M) of PMAO and MMAO are prepared as well.

Polymerizations are conducted in 8 well arrays substantially similar to the conditions employed using the 96 well array. Two different processing conditions, Method 3 and Method 4, differing only as to polymerization temperature are employed.

Method 3 and 4—in situ complex formation, 2.5 mL total volume per well: The ligand array (0.3-1.2 µmol of each ligand source) is charged with toluene (100 µL per well) and then toluene solutions of zirconium tetrabenzyl metal precursor (15-60 µL per well, 0.3-1.2 µmol) are added. The resultant mixtures are stirred for 45 minutes at 75° C. within an aluminum block (pre-mix array). The pre-mix array is allowed to cool to 25° C. with stirring. Individual vials are then treated with a stock solution of the appropriate scavenger (30-60 µL per well, 5:1 equivalent ratio based on metal complex, contact time 10 min, 25° C.), followed by an activator (or activator mixture), 30-75 µL per well, 1:1 equivalent ratio based on metal complex, contact time 2 min. 25° C.). Individual aliquots of the resulting solutions are transferred to 15 mL tarred glass vials containing polytetrafluoroethylene coated stir bars; along with 2.5 mL of styrene and additional Group 13 reagent (10 µmol). The vials are mounted in a temperature controlled 4×3 polymerization array and heated to 105° C. (Method 3) or 125° C. (Method 4). After times from 1-25 minutes following addition of the catalyst solutions, the vials are removed and 3 mL of toluene are added. The 15 mL vials are then removed from the glove box; transferred to a fume hood; and quenched with 5 mL of methanol. Selected results are contained in Table 2.

TABLE 2

| Run | T (° C.) | scavenger | activator | µmol cat. | ligand source | time (min) | yield (mg) | conv. (%) | activity* | Mw ($\times 10^{-3}$) | Mw/Mn |
|---|---|---|---|---|---|---|---|---|---|---|---|
| ps54 | 105 | PMAO | SJBF20 | 0.499 | A4 | 5 | 259 | 11 | 104 | 124 | 2.4 |
| ps55 | 105 | PMAO | SJBF20 | 0.499 | A4 | 15 | 536 | 24 | 72 | 95 | 2.4 |
| ps56 | 105 | PMAO | SJBF20 | 0.500 | A5 | 5 | 1316 | 58 | 526 | 126 | 3.2 |
| ps57 | 105 | TIBA | ABF20 | 0.500 | A5 | 5 | 556 | 25 | 222 | 137 | 2.6 |
| ps58 | 125 | PMAO) | SJBF20 | 0.500 | A5 | 5 | 1011 | 45 | 404 | 111 | 2.7 |
| ps59 | 125 | PMAO | SJBF20 | 0.250 | A5 | 10 | 748 | 33 | 299 | 97 | 3.0 |
| ps61 | 105 | PMAO | SJBF20 | 0.500 | A12 | 3 | 1747 | 77 | 1165 | 84 | 3.0 |
| ps62 | 105 | TIBA | ABF20 | 0.500 | A12 | 3 | 1780 | 79 | 1187 | 95 | 3.3 |
| ps63 | 125 | PMAO | SJBF20 | 0.250 | A12 | 5 | 1053 | 47 | 843 | 130 | 2.7 |
| ps64 | 125 | TIBA | ABF20 | 0.125 | A12 | 5 | 421 | 19 | 674 | 152 | 3.1 |

*mg polymer/(µmol Zr × min)

Solution Styrene Homopolymerization in 8-well Combinatorial Array Methods 5 and 6—isolated complex formation, 4.0 mL total volume per well: The polymerization conditions of Methods 3 and 4 are substantially repeated accepting that previously prepared and isolated metal complexes M1-M8 (15-60 μL per well, 0.3-1.2 μmol) are used. In addition, the polymerizations are conducted using 2 ml styrene and 2 ml of toluene at 105° C. (Method 5) or 2 ml styrene and 2 ml ethylbenzene at 125° C. (Method 6). Selected results are contained in Table 3.

Propylene Solution Polymerization
Polymerization Reactor Preparation:
Method A: A pre-weighed glass vial insert and disposable stirring paddle are fitted to each reaction vessel of a multi-well, computer controlled parallel reactor. The reactor is then sealed and 0.100 mL of a 0.02 M toluene solution of PMAO scavenger (5:1 molar ratio based on metal complex) and 3.9 mL of toluene are injected into each pressure reaction vessel through a valve. The temperature is adjusted to the preselected value, the stirring speed is set to 800 rpm, and each cell

TABLE 3

| Run | T (° C.) | scavenger (eq.)* | activator (eq.)* | catalyst | μmol catalyst | time (min.) | yield (mg) | conversion (percent) | activity** | Mw | Mw/Mn | Tm (° C.) | % mm | % rr |
|---|---|---|---|---|---|---|---|---|---|---|---|---|---|---|
| ps65 | 105 | — | — | — | | 5 | 8 | 0 | | | | | | |
| ps66 | 105 | PMAO (5) | SJ2BF20 (—) | | 0.500*** | 5 | 45 | 3 | | 26 | 4.8 | | | |
| ps67 | 105 | TMA (5) | SJ2BF20 (1) | M1 | 0.500 | 5 | 139 | 8 | 56 | 50 | 2.5 | | | |
| ps68 | 105 | TEA (5) | SJ2BF20 (1) | M1 | 0.500 | 5 | 91 | 5 | 36 | 45 | 2.3 | | | |
| ps69 | 105 | PMAO (5) | SJ2BF20 (1) | M1 | 0.500 | 5 | 180 | 10 | 72 | 85 | 3.0 | | | |
| ps70 | 105 | TIBA (5) | SJ2BF20 (1) | M1 | 0.500 | 5 | 158 | 9 | 63 | 78 | 2.5 | | | |
| ps71 | 105 | MMAO (5) | SJ2BF20 (1) | M1 | 0.500 | 5 | 174 | 10 | 70 | 81 | 2.8 | | | |
| ps72 | 125 | PMAO (5) | SJ2BF20 (1) | M1 | 1.000 | 2 | 283 | 16 | 142 | 59 | 2.6 | | | |
| ps73 | 125 | PMAO (5) | SJ2BF20 (1) | M1 | 1.000 | 5 | 429 | 24 | 86 | 51 | 2.2 | | | |
| ps74 | 125 | PMAO (5) | SJ2BF20 (1) | M1 | 1.000 | 10 | 544 | 30 | 54 | 54 | 2.3 | no melt | 62.7 | 11.1 |
| ps75 | 125 | PMAO (5) | SJ2BF20 (1) | M1 | 1.000 | 15 | 587 | 32 | 39 | 55 | 1.9 | | | |
| ps76 | 125 | PMAO (5) | SJ2BF20 (1) | M1 | 1.000 | 20 | 650 | 36 | 33 | 56 | 2.1 | | | |
| ps77 | 125 | PMAO (5) | SJ2BF20 (1) | M1 | 1.000 | 25 | 667 | 37 | 27 | 55 | 2.2 | | | |
| ps78 | 105 | TIBA (15) | BF15 (1) | M5 | 0.500 | 5 | 875 | 48 | 350 | 151 | 1.5 | | | |
| ps79 | 105 | TIBA (15) | BF15 (1) | M5 | 0.250 | 5 | 392 | 22 | 314 | 184 | 1.5 | 205.9 | | |
| ps80 | 105 | TIBA (15) | BF15 (1) | M5 | 0.125 | 5 | 193 | 11 | 308 | 181 | 1.4 | | | |
| ps81 | 105 | TIBA (15) | SJ2BF20 (1) | M5 | 0.125 | 5 | 124 | 7 | 198 | 197 | 1.5 | | | |
| ps82 | 105 | PMAO (50) | SJ2BF20 (1) | M5 | 0.250 | 5 | 460 | 25 | 368 | 180 | 1.4 | 206.9 | 90.1 | 1.2 |
| ps83 | 105 | PMAO (50) | SJ2BF20 (1) | M5 | 0.125 | 5 | 160 | 9 | 256 | 189 | 1.5 | | | |
| ps84 | 105 | PMAO (50) | PMAO (200) | M5 | 0.125 | 5 | 184 | 10 | 294 | 184 | 1.5 | | | |
| ps85 | 125 | PMAO (50) | SJ2BF20 (1) | M5 | 0.125 | 2 | 129 | 7 | 516 | 129 | 1.8 | | | |
| ps86 | 125 | TIBA (15) | BF15 (1) | M5 | 0.125 | 2 | 169 | 9 | 674 | 122 | 1.8 | | | |
| ps87 | 125 | PMAO (50) | SJ2BF20 (1) | M5 | 0.250 | 5 | 627 | 35 | 502 | 107 | 1.6 | | | |
| ps88 | 125 | PMAO (50) | SJ2BF20 (1) | M5 | 0.125 | 5 | 319 | 18 | 510 | 111 | 1.6 | | | |
| ps89 | 125 | PMAO (50) | SJ2BF20 (1) | M5 | 0.063 | 5 | 159 | 9 | 510 | 113 | 1.7 | | | |
| ps90 | 125 | TIBA (15) | BF15 (1) | M5 | 0.125 | 5 | 447 | 25 | 716 | 102 | 1.7 | | | |
| ps91 | 125 | PMAO (50) | SJ2BF20 (1) | M5 | 0.125 | 10 | 518 | 29 | 414 | 109 | 1.7 | | | |
| ps92 | 125 | TIBA (15) | BF15 (1) | M5 | 0.125 | 10 | 868 | 48 | 694 | 102 | 1.7 | no melt | | |
| ps93 | 125 | PMAO (50) | SJ2BF20 (1) | M5 | 0.125 | 15 | 785 | 43 | 419 | 110 | 1.6 | | | |
| ps94 | 125 | TIBA (15) | BF15 (1) | M5 | 0.125 | 15 | 1063 | 59 | 567 | 96 | 1.8 | | | |
| ps95 | 125 | TIBA (15) | BF15 (1) | M5 | 0.125 | 20 | 1266 | 70 | 506 | 95 | 1.8 | | | |
| ps96 | 125 | TIBA (15) | BF15 (1) | M5 | 0.125 | 25 | 1369 | 76 | 438 | 84 | 1.8 | no melt | 83.0 | 4.6 |
| ps97 | 125 | TIBA (15) | BF15 (1) | M6 | 0.125 | 2 | 163 | 9 | 653 | 115 | 1.8 | | | |
| ps98 | 125 | TIBA (15) | BF15 (1) | M6 | 0.125 | 5 | 425 | 23 | 679 | 112 | 1.7 | | | |
| ps99 | 125 | TIBA (15) | BF15 (1) | M6 | 0.125 | 10 | 803 | 44 | 642 | 117 | 1.6 | 192.9 | | |
| Ps100 | 125 | TIBA (15) | BF15 (1) | M6 | 0.125 | 15 | 1110 | 61 | 592 | 106 | 1.7 | | | |
| Ps101 | 125 | TIBA (15) | BF15 (1) | M6 | 0.125 | 20 | 1261 | 70 | 504 | 103 | 1.7 | | | |
| Ps102 | 125 | TIBA (15) | BF15 (1) | M6 | 0.125 | 25 | 1315 | 73 | 421 | 96 | 1.8 | no melt | | |
| Ps103 | 105 | TIBA (5) | BF15 (1) | M3 | 0.500 | 5 | 611 | 34 | 245 | 103 | 1.6 | | | |
| Ps104 | 105 | TIBA (5) | BF15 (1) | M3 | 0.250 | 5 | 293 | 16 | 234 | 111 | 1.5 | | | |
| Ps105 | 105 | TIBA (5) | BF15 (1) | M3 | 0.125 | 5 | 144 | 8 | 230 | 106 | 1.6 | | | |
| Ps106 | 105 | TIBA (5) | SJ2BF20 (1) | M3 | 0.125 | 5 | 101 | 6 | 161 | 83 | 2.0 | | | |
| Ps107 | 105 | PMAO (5) | SJ2BF20 (1) | M3 | 0.500 | 5 | 623 | 34 | 249 | 105 | 1.6 | no melt | 77.9 | 4.1 |
| Ps108 | 105 | PMAO (5) | SJ2BF20 (1) | M3 | 0.125 | 5 | 112 | 6 | 179 | 78 | 2.1 | | | |
| Ps109 | 105 | PMAO (5) | PMAO (200) | M3 | 0.125 | 5 | 221 | 12 | 354 | 76 | 1.6 | | | |
| Ps110 | 125 | TIBA (5) | BF15 (1) | M3 | 0.250 | 2 | 188 | 13 | 376 | 94 | 2.4 | | | |
| Ps111 | 125 | TIBA (5) | BF15 (1) | M3 | 0.250 | 5 | 283 | 16 | 226 | 69 | 2.0 | no melt | 71.8 | 8.4 |
| Ps112 | 125 | PMAO (5) | PMAO (200) | M3 | 0.250 | 5 | 304 | 17 | 243 | 42 | 1.9 | | | |
| Ps113 | 125 | TIBA (5) | BF15 (1) | M3 | 0.250 | 5 | 287 | 19 | 230 | 67 | 1.8 | | | |
| Ps114 | 125 | TIBA (5) | BF15 (1) | M3 | 0.250 | 10 | 382 | 26 | 153 | 68 | 1.7 | no melt | | |
| Ps115 | 125 | TIBA (5) | BF15 (1) | M3 | 0.250 | 15 | 413 | 28 | 110 | 64 | 1.7 | | | |
| Ps116 | 125 | TIBA (5) | BF15 (1) | M3 | 0.250 | 20 | 471 | 32 | 94 | 66 | 1.7 | | | |
| Ps117 | 125 | TIBA (5) | BF15 (1) | M3 | 0.250 | 25 | 475 | 32 | 76 | 64 | 1.7 | | | |

*based on metal complex
**mg polymer/(μmol metal complex × min)
***umol of activator used is exposed to propylene at 100 psi (700 kPa) pressure. Propylene is supplied to the cell on demand and the temperature setting is maintained until the end of the polymerization experiment.

Method B: Method B is substantially the same as method A, excepting that trimethylaluminium ("TMA") is used as the scavenger (5:1 molar ratio based on metal complex).

In situ preparation of metal complexes:

Method AA: 30 μl of toluene is added to a 1 mL glass vial containing 1.2 μmol of previously prepared ligand source (A1-A47). An equimolar amount of metal precursor solution (120 μl of 10 mM solution in toluene). The reaction mixture is heated to 75° C. for 30 minutes and the vials are transferred to a room temperature microtiter plate for use.

Method BB: 40 μl of toluene is added to a 1 mL glass vial containing 1.1 μmol of the ligand source. An equimolar amount of metal precursor solution (110 μl of 10 mM solution in toluene) is added and the mixture is heated to 75° C. for 30 minutes. The vials are transferred to a room temperature microtiter plate for use.

Preparation of Scavenger and Activator Stock Solutions: the Activator Solution is trityltetrakis (pentafluorophenyl) borate ("TBF20") prepared as a 5 mM solution in toluene. The scavenger solutions are 50 mM toluene solutions of TMA or PMAO.

Catalyst Activation Method

Method AAA: To the reactor cells containing the metal complex solution the appropriate amount of scavenger solution is added. After about 10 minutes, 1.1 mol equivalents (based on metal precursor) of the activator is added and the reaction mixture mixed. After another 30 seconds, an aliquot of activated catalyst solution is withdrawn and injected into the prepressurized reactor followed immediately by injection of toluene to bring the total volume (activator solution+toluene) injected to 0.800 mL.

Method BBB: The conditions of Method AAA are repeated, excepting that the quantity of toluene injected after addition of activator is increased to raise the total volume injected into the prepressurized reaction vessel to 1.00 mL.

Method CCC: The conditions of Method AAA are repeated, excepting that the quantity of toluene injected after addition of activator is increased to raise the total volume injected into the prepressurized reaction vessel to 0.500 mL.

Polymerization conditions: Polymerization is conducted for 1-30 minutes, at a reactor temperature of 75° C. The reaction is quenched by addition of an overpressure of carbon dioxide after either the maximum allowable polymerization time has elapsed or consumption of a predetermined quantity of propylene occurs.

Product work up: The glass vial insert containing the polymer product and solvent is removed from the pressure cell and from the inert atmosphere dry box. In those cases where significant propylene uptake is measured but solid polymer or a viscous solution is not observed, the vial is sampled for GC analysis of any volatile products (indicated by "oligomers" in Table 4). The volatile components are removed from polymerized samples using a centrifuge vacuum evaporator, followed by drying at elevated temperature under reduced pressure in a vacuum oven. The vial is then weighed to determine the yield of non-oligomeric product. Molecular weights of the polymer produced are determined by rapid GPC analysis Selected results are contained in Table 4.

TABLE 4

| Run | ligand | precursor | reactor prep. | complex prep. | catalyst activation | scavenger | activator | μmol complex | time (min.) | yield (mg) | activity* | Mw (×10$^{-3}$) | Mw/Mn |
|---|---|---|---|---|---|---|---|---|---|---|---|---|---|
| PP1 | A1 | TiBz4 | A | AA | AAA | PMAO | TBF20 | 0.60 | 30.0 | 8 | 0.5 | | |
| PP2 | A4 | TiBz4 | A | AA | AAA | PMAO | TBF20 | 0.60 | 1.2 | 350 | 486 | 6 | 1.4 |
| PP3 | A2 | TiBz4 | A | AA | AAA | PMAO | TBF20 | 0.60 | 30.0 | 8 | 0.4 | | |
| PP4 | A3 | TiBz4 | A | AA | AAA | PMAO | TBF20 | 0.60 | 30.0 | 4 | 0.2 | | |
| PP5 | A1 | ZrBz4 | B | AA | AAA | TMA | TBF20 | 0.60 | 2.4 | 172 | 120 | 4 | 1.2 |
| PP6 | A4 | ZrBz4 | B | AA | AAA | TMA | TBF20 | 0.60 | 30.0 | 2 | 0.1 | | |
| PP7 | A2 | ZrBz4 | B | AA | AAA | TMA | TBF20 | 0.60 | 4.7 | 89 | 32 | 3 | 1.3 |
| PP8 | A3 | ZrBz4 | B | AA | AAA | TMA | TBF20 | 0.60 | 30.0 | 17 | 1 | | |
| PP9 | A1 | HfBz4 | A | AA | BBB | PMAO | TBF20 | 1.0 | 8.4 | 87 | 10 | 14 | 1.6 |
| PP10 | A4 | HfBz4 | A | AA | BBB | PMAO | TBF20 | 1.0 | 1.0 | 33 | 32 | oligomers | |
| PP11 | A2 | HfBz4 | A | AA | BBB | PMAO | TBF20 | 1.0 | 20.0 | 80 | 4 | 13 | 1.6 |
| PP12 | A3 | HfBz4 | A | AA | BBB | PMAO | TBF20 | 1.0 | 30.0 | 31 | 1 | | |
| PP13 | A5 | TiBz4 | A | BB | CCC | PMAO | TBF20 | 0.25 | 4.5 | 359 | 321 | 12 | 1.7 |
| PP14 | A16 | TiBz4 | A | BB | CCC | PMAO | TBF20 | 0.25 | 1.4 | 194 | 546 | 3 | 1.2 |
| PP15 | A15 | TiBz4 | A | BB | CCC | PMAO | TBF20 | 0.25 | 30.0 | 40 | 5 | 3 | 1.2 |
| PP16 | A17 | TiBz4 | A | BB | CCC | PMAO | TBF20 | 0.25 | 30.0 | 5 | 1 | | |
| PP17 | A12 | TiBz4 | A | BB | CCC | PMAO | TBF20 | 0.25 | 1.3 | 238 | 752 | 3 | 1.2 |
| PP18 | A5 | ZrBz4 | A | BB | AAA | PMAO | TBF20 | 0.50 | 1.1 | 14 | 27 | oligomers | |
| PP19 | A16 | ZrBz4 | A | BB | AAA | PMAO | TBF20 | 0.50 | 1.0 | 22 | 43 | oligomers | |
| PP20 | A15 | ZrBz4 | A | BB | AAA | PMAO | TBF20 | 0.50 | 1.7 | 1 | 1 | oligomers | |
| PP21 | A17 | ZrBz4 | A | BB | AAA | PMAO | TBF20 | 0.50 | 1.7 | 34 | 39 | oligomers | |
| PP22 | A12 | ZrBz4 | A | BB | AAA | PMAO | TBF20 | 0.50 | 3.9 | 5 | 3 | oligomers | |
| PP23 | A5 | HfBz4 | A | BB | CCC | PMAO | TBF20 | 0.25 | 1.9 | 16 | 32 | oligomers | |
| PP24 | A16 | HfBz4 | A | BB | CCC | PMAO | TBF20 | 0.25 | 1.0 | 10 | 40 | oligomers | |
| PP25 | A15 | HfBz4 | A | BB | CCC | PMAO | TBF20 | 0.25 | 30.0 | 1 | 0.2 | | |
| PP26 | A17 | HfBz4 | A | BB | CCC | PMAO | TBF20 | 0.25 | 18.4 | 65 | 14 | 20 | 2.6 |
| PP27 | A12 | HfBz4 | A | BB | CCC | PMAO | TBF20 | 0.25 | 8.5 | 4 | 2 | oligomers | |

*mg polymer/(μmol metal complex × minute)

Propylene Polymerization Using Isolated Complexes.

Polymerization Reactor Preparation: The reactor preparation method is Method A.

Preparation of Scavenger and Activator Stock Solutions: PMAO is Prepared as a 50 mM solution in toluene. Activators are N,N'-dimethylanilinium-tetrakis(pentafluorophenyl)borate ("ABF20") 5 mM in toluene or trityltetrakis (pentafluorophenyl)borate ("TBF20") 5 mM in toluene.

Catalyst Activation method: 50 μL of PMAO solution (2.5 μmol) is dispensed into a 1 mL vial. 100 μL of the complex solution (5 mM in toluene) containing 0.5 μmol metal complex is added. After 1 minute, 110 μL of the activator solution (0.55 μmol) is added and the contents of the 1 mL vial are mixed. Approximately 1 minute later a sufficient quantity of solution to provide 0.08 μmol of activated catalyst is withdrawn from the cell and injected into the pre-pressurized reaction vessel, followed immediately by injection of toluene to bring the total volume of injected liquid to 0.500 mL.

Polymerization: The polymerization is conducted at 75° C. at a propylene pressure of 60 psig (500 kPa) for time periods from 1-30 minutes. Polymerization is continued until a predetermined quantity of monomer is consumed or 30 minutes is reached. The reaction is then quenched by addition of an overpressure of carbon dioxide.

Product work up: After quenching, the glass vial insert containing the polymer product and solvent is removed from the pressure cell and from the inert atmosphere dry box, and in the cases where significant propylene uptake is measured but solid polymer or a viscous solution is not observed, the vial is sampled for GC analysis of any volatile products (indicated by "oligomers" in Table 5). The volatile components are then removed using a centrifuge vacuum evaporator, followed by drying at elevated temperature under reduced pressure in a vacuum oven. The vial is then weighed to determine the yield of (non-volatile) polymer product. The polymer product is then analyzed by rapid GPC to determine the molecular weight of the polymer produced. Results are contained in Table 5.

TABLE 5

| Run | metal complex | time (min.) | yield (g) | activity* | activity** | Mw (×10$^{-3}$) | Mw/Mn | product appearance |
|---|---|---|---|---|---|---|---|---|
| PP29 | M2 | 10.0 | 121 | 151 | 74 | 21 | 2.2 | viscous liquid |
| PP30 | M2 | 9.9 | 110 | 139 | 77 | 21 | 2.3 | viscous liquid |
| PP31 | M3 | 1.8 | 1 | 5 | 412 | oligomers | | |
| PP32 | M3 | 1.7 | 0 | 0 | 453 | oligomers | | |
| PP33 | M4 | 5.1 | 9 | 22 | 146 | oligomers | | liquid |
| PP34 | M4 | 8.0 | 7 | 11 | 94 | oligomers | | liquid |
| PP35 | M7 | 1.3 | 1 | 12 | 597 | oligomers | | liquid |
| PP36 | M7 | 2.0 | 0 | 0 | 382 | oligomers | | |

*mg polymer/(min × μmol catalyst)
**kPa/(min × μmol catalyst)

High Temperature Solution Styrene Homopolymerization

An 8 well combinatorial reactor is employed to polymerize styrene. Each cell is charged with 1 mL of styrene, 3 mL of p-xylene diluent and 0.25 μmol of catalyst. Triisobutyl aluminum (1.25 μmol in toluene) and activator (SJBF20, 0.25 μmol, toluene solution) are added to each cell. Polymerization conditions are maintained for times up to 30 minutes. Conversions are based on undevolatilized polymer (including trapped solvent) and may exceed 100 percent. Results are contained in Table 6.

TABLE 6

| Run | temp (° C.) | metal complex | conversion (percent) | Mw (×10$^{-3}$) | Mw/Mn | mm (%) | mr (%) |
|---|---|---|---|---|---|---|---|
| Ps118 | 135 | M3 | 79 | 77 | 2.6 | | |
| Ps119 | 170 | M3 | 33 | 74 | 2.5 | | |
| Ps120 | 135 | M6 | 126 | 143 | 3.2 | 72 | 25 |
| Ps121 | 170 | M6 | 110 | 60 | 2.2 | 65 | 32 |

Batch Reactor Styrene Homopolymerization

The styrene polymerizations are conducted in a 2 L Parr batch reactor. The reactor is heated by an electrical heating mantle, and cooled by an internal serpentine cooling coil containing a glycol/water mixture. Both the reactor and the heating/cooling system are controlled and monitored by a process computer. The bottom of the reactor is fitted with a discharge valve, which empties the reactor contents into a 2 L stainless steel container, which contains a small amount of 1-butanol as a catalyst kill. The container is vented to a 113 L blow down tank, with both the container and the tank purged with nitrogen. Solvents and styrene monomer used for polymerization are passed through purification columns, to remove any impurities that may effect polymerization. The toluene is passed through 2 columns, the first containing A-2 alumna (available from LaRoche Inc.), the second containing Q5 reactant (available from Englehard Chemicals Inc.). The styrene was passed through an A-2 alumina column. The nitrogen, used for transfers, is passed through a single column containing A-204 alumna (available from LaRoche Inc.), 4A° (0.4 nm) molecular sieves and Q5 reactant.

The styrene was loaded from a shot tank that is filled and nitrogen purged daily. The reactor is loaded from the liquid shot tank that contains styrene and toluene. The shot tank is filled to the load setpoints by use of a scale upon which the tank is mounted. After solvent and monomer addition, the reactor is heated to the polymerization temperature setpoint.

The catalyst (M17) and activator (SJBF20) are mixed with the appropriate amount of toluene to achieve a desired solution concentration. The catalyst and activator(s) are handled in an inert glovebox. The catalyst is first mixed with 5 equivalents of triisobutylaluminum for 5 minutes followed by addition of 1 equivalent of SJBF20 metal complex. The catalyst solution is then drawn into a syringe and pressure transferred into the catalyst shot tank. This is followed by 3 rinses of toluene, 5 mL each.

Immediately after catalyst addition the run timer begins. These polymerizations are typically conducted for 60 minutes, then the agitator is stopped and the bottom discharge valve opened to empty the reactor contents to the receiving vessel. The polymer solution is poured into evaporation trays and placed in a lab hood where the solvent is evaporated overnight. The trays containing the residual polymer are then transferred to a vacuum oven, where they are heated under reduced pressure atmosphere to remove the remaining solvent and styrene. After the trays cool to ambient temperature, the polymer is weighed for yield/efficiencies calculations.

DSC Measurements: Samples of approximately 8.0 to 10.0 mg size are placed in hermetically sealed DSC pans. The instrument is a TA Instruments, Inc., model 2910 DSC. The samples are scanned from room temperature to 250° C. with a ramp rate of 1 deg/min. (first scan), then cooled from 250° C. to 30° C. at 1 deg/min (2nd scan) using the air cool option, not liquid nitrogen. Finally the sample is heated again to 250° C. at 1 deg/min (3rd scan). The melting peak (if any) is integrated using the software supplied with the DSC instrument. Crystallization, if present, is determined by the existence of an endotherm in the heating scans or an exotherm in the cooling scan.

Tacticity Determination by $^{13}$C NMR Spectroscopy: NMR spectra are collected on a Varian Corporation, Mercury™ Vx 300 instrument using 5 mm probe. Samples are prepared by dissolving approximately 300 mg of polymer in 1 mL of CDCl3. The following acquisition parameters are used: delay time—3 second, acquisition time—1 second, number of transients=10,000-20,000. Line broadening of 1 is used during Fourier transformation of the data. Percent of mm, mr and rr triads are determined by integration of the NMR spectrum in the region 145.8-146.8, 144.9-145.8 and 143.8-144.9 ppm respectively. Results are reported in Table 7.

TABLE 7

| Run | Temp. (° C.) | Toluene (g) | Styrene (g) | Catalyst (μmol) | Time (h) | Yield (g) | Efficiency (g poly/g Zr) | Mw | Mw/Mn | % mm | % mr | % rr | Tg (° C.) | Mp (° C.) |
|---|---|---|---|---|---|---|---|---|---|---|---|---|---|---|
| Ps122 | 100 | 347 | 110 | 1 | 1 | 26.6 | 291,590 | 255,000 | 1.84 | 84.3 | 14.7 | 1.0 | 95.0 | nd* |
| Ps123 | 130 | 347 | 110 | 1 | 1 | 55.2 | 605,104 | 120,000 | 2.02 | 82.0 | 17.7 | 0.3 | 93.0 | nd* |
| Ps124 | 160 | 347 | 110 | 1 | 1 | 65 | 712,532 | 55,000 | 1.98 | 71.5 | 26.4 | 2.1 | 93.4 | nd* |
| Ps126 | 130 | 427 | 25 | 1 | 1 | 9.1 | 99,754 | 64,000 | 1.94 | 81.9 | 18.0 | 0.1 | — | — |
| Ps127 | 130 | 404 | 50 | 1 | 1 | 20.5 | 224,722 | 97,000 | 1.92 | 78.2 | 20.7 | 1.1 | — | — |
| Ps128 | 130 | 356 | 100 | 1 | 1 | 49.1 | 538,236 | 117,000 | 1.82 | 74.8 | 23.1 | 2.1 | — | — |
| Ps129 | 130 | 260 | 200 | 1 | 1 | 79.9 | 875,866 | 117,000 | 1.77 | 75.0 | 23.7 | 1.3 | — | — |
| Ps130 | 100 | 500 | 500 | 1.5 | 3 | 254.6 | 1,860,621 | 217,000 | 2.22 | 82.3 | 17.1 | 0.6 | — | — |

*not detected

What is claimed is:

1. A metal complex characterized by the formula:

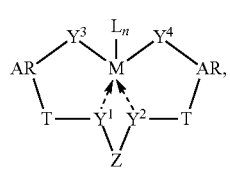
(I)

wherein, $Y^1$, $Y^2$, $Y^3$ and $Y^4$ is each independently selected from the group consisting of oxygen and sulfur, and optional donor bonds between $Y^1$ and M and between $Y^2$ and M are indicated by dashed arrows;

Z is a divalent group having up to 50 atoms, not counting hydrogen atoms;

each AR is a divalent aromatic group of up to 50 atoms, not counting hydrogen atoms;

each T is a group having up to 30 atoms total of the general formula —$(CR^{20}_{2-x''})_{x'}$—, wherein each $R^{20}$ substituent is independently selected from the group consisting of hydrogen, halogen, hydrocarbyl, inertly substituted hydrocarbyl, and groups of the formula: $Q(R^{21})_y$, wherein $R^{21}$ is hydrogen, halogen, hydrocarbyl, or inertly substituted hydrocarbyl, Q is O, P, S, N, Si or B, and y is an integer from 1 to 3 equal to one less than the valence of Q; x' is 1 or 2; and x" is 0 or 1; and optionally two or more $R^{20}$ substituents may be joined into a ring- or multiring-structure having from 3 to 30 atoms, provided that said ring structure is not an aromatic group;

M is a metal selected from the group consisting of Groups 3-6 and Lanthanides of the Periodic Table of the Elements;

n is a number from 1 to 6; and each L is a neutral, monovalent or divalent ligand containing up to 50 atoms not counting hydrogen.

2. The metal complex of claim 1 wherein M is a Group 4 metal and L, independently each occurrence, is hydrocarbyl or halide.

3. The metal complex of claim 1, characterized by the formula:

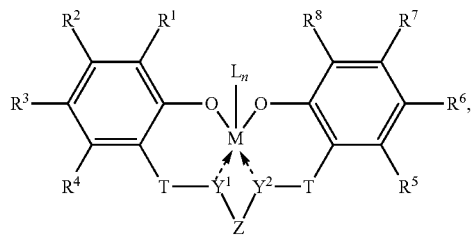

wherein $R^1$-$R^8$ are each independently selected from the group consisting of hydrogen, halogen, hydrocarbyl, substituted hydrocarbyl, heterohydrocarbyl, hydrocarbyloxy, substituted hydrocarbyloxy, silyl, siloxy, boryl, dihydrocarbylphosphino, substituted dihydrocarbylphosphino, dihydrocarbylamino, substituted dihydrocarbylamino, hydrocarbylthio, substituted hydrocarbylthio, and combinations thereof any two or more selected from $R^1$-$R^4$ or $R^5$-$R^8$ may be linked together to form one or more multiple ring structures; and M, L, n, T, Y', $Y^2$ and Z are as previously defined in claim 1.

4. A metal complex according to claim 1 wherein each T is a moiety of the formula: —$CR^{22}_2$—, wherein each $R^{22}$ substituent is hydrogen, halogen, hydrocarbyl, or substituted hydrocarbyl of up to 20 atoms.

5. A metal complex according to claim 1 wherein Z corresponds to the formula: -$(Q'R^{30}_2)_{m'}$—, wherein, Q', independently each occurrence, is selected from the group consisting of carbon and silicon, each $R^{30}$ is selected from the group consisting of hydrogen, halogen, hydrocarbyl, and substituted hydrocarbyl, said group having from 1 to 50 atoms, and optionally two or more $R^{30}$ substituents on the same or different Q' atoms, may be joined into a ring or multiple ring structure, and m' is an integer from 1 to 10.

6. A metal complex according to claim 5 wherein Z is selected from the group consisting of: —$(CH_2)$—, —$(CH_2)_2$—, —$(CH_2)_3$—, —$(CH_2)_4$—, —$(CH(CH_3))$—, —$(CH(CH_3))_2$—, —$(C(CH_3)_2)$—, —$(C(CH_3)_2)_2$—, —$(C(CH_3)_2)_3$—, —$CH_2CH(CH_3)CH_2$—, —$CH_2C(CH_3)_2CH_2$—, —$CH_2CH(C_6H_5)CH_2$—, —$CH(CH_3)CH_2CH(CH_3)$—, —$Si(CH_3)_2$—, —$Si(C_6H_5)_2$—, —$CH(C_2H_5)CH_2CH(C_2H_5)$—, —$CH(CH_3)CH_2CH_2CH(CH_3)$—, —$CH(C_6H_5)CH_2CH(C_6H_5)$—,

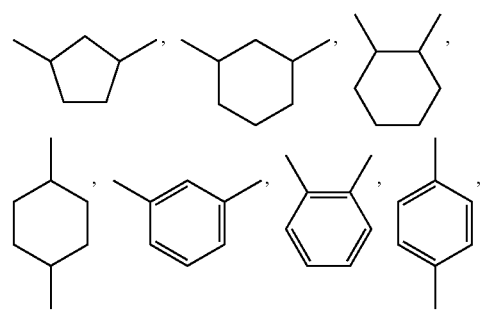

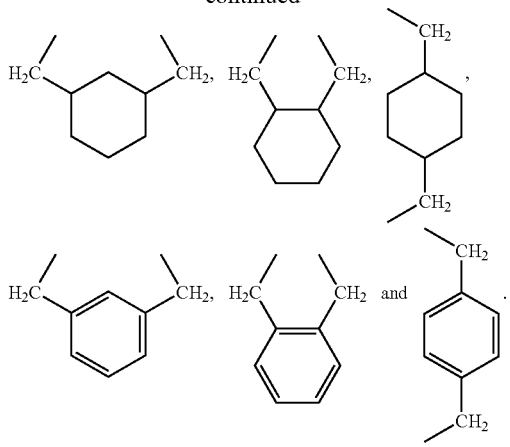

7. A metal complex according to claim 1 wherein each L is a ligand independently selected from the group consisting of hydrogen, halogen, optionally substituted alkyl, heteroalkyl, allyl, diene, alkenyl, heteroalkenyl, alkynyl, heteroalkynyl, aryl, heteroaryl, alkoxy, aryloxy, boryl, silyl, amino, phosphino, ether, thioether, phosphine, amine, carboxylate, alkylthio, arylthio, 1,3-dionate, oxalate, carbonate, nitrate, sulphate, and combinations thereof.

8. A composition comprising the reaction product or mixture resulting from contacting a ligand source characterized by the formula:

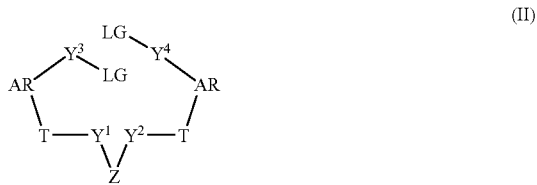

wherein LG is a leaving group having up to 10 atoms;
$Y^1$, $Y^2$, $Y^3$ and $Y^4$ is each independently selected from the group consisting of oxygen, phosphorus and sulfur;
Z is a divalent group having up to 50 atoms, not counting hydrogen atoms;
each AR is a divalent aromatic group of up to 50 atoms, not counting hydrogen atoms;

each T is a group having up to 30 atoms total of the general formula $—(CR^{20}_{2-x''})_{x'}—$, wherein each $R^{20}$ substituent is independently selected from the group consisting of hydrogen, halogen, hydrocarbyl, inertly substituted hydrocarbyl, and groups of the formula: $Q(R^{21})_y$, wherein $R^{21}$ is hydrogen, halogen, hydrocarbyl, or inertly substituted hydrocarbyl, Q is O, P, S, N, Si or B, and y is an integer from 1 to 3 equal to one less than the valence of Q; x' is 1 or 2; and x'' is 0 or 1; and optionally two or more $R^{20}$ substituents may be joined into a ring- or multiring-structure having from 3 to 30 atoms, provided that said ring structure is not an aromatic group;
with a metal compound corresponding to the formula: $M(L)_{n'}$, or a dimeric or higher order derivative thereof, where
M is a Group 3-6 or Lanthanide metal;
each L is a neutral, monovalent or divalent ligand containing up to 50 atoms not counting hydrogen; and
n' is a number from 3 to 8.

9. A method for forming an oligomeric or polymeric product, comprising contacting one or more addition polymerizable monomers with a catalyst comprising a metal complex or composition according to any of claims 1 to 8 and, optionally, an activator.

10. The method of claim 9, wherein the monomer is an ethylenically unsaturated compound containing from 2 to 20 atoms not counting hydrogen.

11. The method of claim 10, wherein the product is a polymer and the monomer is propylene or a vinylidene aromatic monomer.

12. The method of claim 11 wherein the vinylidene aromatic monomer is styrene.

13. The method of claim 11 conducted in a solution polymerization reactor and conducted at a temperature greater than or equal to 100° C., and wherein the resulting polymer has a rr triad content of less than 30 percent and a mm triad content of from 25 to 100 percent.

14. The method of claim 11 wherein the polymer has no appreciable melting point as determined by DSC.

15. The method of any one of claim 12 or 13, wherein the polymer is substantially amorphous due to the presence of stereo- and/or regio-errors in the polymer structure.

16. The method of claim 12, conducted at a temperature of from 110 to 170° C.

* * * * *